United States Patent
Kalla et al.

(10) Patent No.: US 11,052,139 B2
(45) Date of Patent: Jul. 6, 2021

(54) COMPOSITIONS AND METHODS FOR ENHANCING THE STABILITY OF TRANSGENES IN POXVIRUSES

(71) Applicant: Bavarian Nordic A/S, Kvistgaard (DK)

(72) Inventors: Markus Kalla, Penzberg (DE); Ryan Rountree, San Mateo, CA (US); Ulrike Dirmeier, Starnberg (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 16/337,086

(22) PCT Filed: Sep. 28, 2017

(86) PCT No.: PCT/EP2017/074693
§ 371 (c)(1),
(2) Date: Mar. 27, 2019

(87) PCT Pub. No.: WO2018/060368
PCT Pub. Date: Apr. 5, 2018

(65) Prior Publication Data
US 2020/0061174 A1 Feb. 27, 2020

Related U.S. Application Data

(60) Provisional application No. 62/401,035, filed on Sep. 28, 2016.

(51) Int. Cl.
| | | |
|---|---|---|
| A61K 39/00 | (2006.01) | |
| A61K 39/12 | (2006.01) | |
| A61K 48/00 | (2006.01) | |
| A61K 39/285 | (2006.01) | |
| A61K 45/06 | (2006.01) | |
| C07K 14/47 | (2006.01) | |
| C07K 14/705 | (2006.01) | |
| C12N 15/863 | (2006.01) | |

(52) U.S. Cl.
CPC .... *A61K 39/0011* (2013.01); *A61K 39/00117* (2018.08); *A61K 39/001182* (2018.08); *C07K 14/4727* (2013.01); *C07K 14/70525* (2013.01); *C07K 14/70528* (2013.01); *C07K 14/70532* (2013.01); *C12N 15/863* (2013.01); *A61K 2039/5256* (2013.01); *A61K 2039/545* (2013.01); *A61K 2039/6031* (2013.01); *C12N 2710/24143* (2013.01)

(58) Field of Classification Search
CPC ... A61K 2300/00; A61K 35/768; A61P 35/00; C12N 2710/24143; C12N 15/86
See application file for complete search history.

(56) References Cited

FOREIGN PATENT DOCUMENTS

| WO | 2005046614 A2 | | 5/2005 |
|---|---|---|---|
| WO | WO2005/046614 | * | 5/2005 |
| WO | 2005058937 A2 | | 6/2005 |
| WO | WO2005058937 | * | 6/2005 |
| WO | 2013103658 A1 | | 7/2013 |
| WO | WO2013103658 | * | 7/2013 |
| WO | 2015061416 A2 | | 4/2015 |
| WO | WO2015061416 | * | 4/2015 |

OTHER PUBLICATIONS

Madan et al., "Panvac(TM)-VF: poxviral-based vaccine therapy targeting CEA and MUC1 in carcinoma," (2007) Expert Op. Biol. Ther. 7: 543-554.
Wyatt et al., "Elucidating and minimizing the loss by recombinant vaccinia virus of HIV gene expression . . . ," (2009) J. Virol. 83: 7176-84.

* cited by examiner

*Primary Examiner* — Barry A Chestnut

(57) ABSTRACT

Provided herein are recombinant poxviruses that are stable through successive passaging of the recombinant poxviruses. More particularly, the recombinant poxviruses comprise one or more modified nucleic acids encoding MUC1, CEA, and/or TRICOM antigens, wherein the recombinant poxviruses are stable through successive passaging. Also, provided herein are compositions and method related thereto.

13 Claims, 22 Drawing Sheets
Specification includes a Sequence Listing.

Figure 2A

PANVAC - MUC1

MTPGTQSPFFLLLLTVLTVVTGSGHASSTPGGEKETSATQRSSVPSSTEKNAV
SMTSSVLSSHSPGSGSSTTQGQDVTLAPATEPASGSAALWGQDVTSVPVTRPAL

6x VNTR {
GSTAPPAHGVTSAPDTRPAP    VNTR #1
GSTAPPAHGVTSAPDTRPAP    VNTR #2
GSTAPPAHGVTSAPDTRPAP    VNTR #3
GSTAPPAHGVTSAPDTRPAP    VNTR #4
GSTAPPAHGVTSAPDTRPAP    VNTR #5
GSTAPPAHGVTSAPDTRPAP    VNTR #6
}

ASTLVHNGTSARATTTPASKSTPFSIPSHHSDTPTTLASHSTKTDASSTHHSTV
PPLTSSNHSTSPQLSTGVSFFFLSFHISNLQFNSSLEDPSTDYYQELQRDISEM
FLQIYKQGGFLGLSNIKFRPGSVVVQLTLAFREGTINVHDVETQFNQYKTEAAS
RYNLTISDVSVSDVPFPFSAQSGAGVPGWGIALLVLVCVLVALAIVYLIALAVC
QCRRKNYGQLDIFPARDTYHPMSEYPTYHTHGRYVPPSSTDRSPYEKVSAGNGG
SSLSYTNPAVAATSANL-

Figure 2B mBN336/mBN373/mBN420 - MUC1

```
MTPGTQSPFFLLLLTVLTVVTGSGHASSTPGGEKETSATQRSSVPSSTEKNAV
SMTSSVLSSHSPGSGSSTTQGQDVTLAPATEPASGSAALWGQDVTSVPVTRPAL
GYLAPPAHGVTSYLDTRPAP  ← VNTR #1 (PANVAC VNTR # 2)
VSTAPPAHGVTSAPDTRPAP  ← VNTR #2 (PANVAC VNTR # 1)
GSTAPPAHGVTSAPDTRPAP  ← VNTR #3 (PANVAC VNTR # 3)
ASTLVHNGTSARATTTPASKSTPFSIPSHHSDTPTTLASHSTKTDASSTHHSTV
PPLTSSNHSTSPQLSTGVSFFFLSFHISNLQFNSSLEDPSTDYYQELQRDISEM
FLQIYKQGGFLGLSNIKFRPGSVVVQLTLAFREGTINVHDVETQFNQYKTEAAS
RYNLTISDVSVSDVPFPFSAQSGAGVPGWGIALLVLVCVLVYLLAIVYLLIALAVC
QVRRKNYGQLDIFPARDTYHPMSEYPTYHTHGRYVPPSSLFRSPYEKVSAGNGG
SYLSYTNPAVAATSANL-
```

3 x VNTR { (bracketing VNTR #1, #2, #3)

| | | |
|---|---|---|
| PANVAC_CEA | gtcagcgccaggagtctgattcagtgatcctcaagtgctgttacggaccgatgctct | 720 |
| mBN373/420_CEA | gtcagcgccaggagtctgattcagtcgatgatcctcaactgctgcttacggaccgatgctcct | 720 |
| PANVAC_CEA | acaatcagccctctaaacacaagtatagatcaggaaatctgaatctgagctgtcat | 780 |
| mBN373/420_CEA | acaatcagccctctaaacacagtcagatcagagaaatctgaatctgagctgtcat | 780 |
| PANVAC_CEA | gccgctagcaatcccgcccaatacacagcctggtttgtcaatggcacttccaacagtcc | 840 |
| mBN373/420_CEA | gccgctagcaatccgcagtcaatacacagccggttcgtcaatggcacttccaacagtcc | 840 |
| PANVAC_CEA | acccaggaactgttcattccaatattacgtgaacaatagtgatcctacacgtgccaa | 900 |
| mBN373/420_CEA | acccaggaactgttcattccaatattacgtgaacaatagtgatcctacacgtgccaa | 900 |
| PANVAC_CEA | gctcacaatagcgacgaccggactcaacgcaacccgtgacgacgattacgtgtatgag | 960 |
| mBN373/420_CEA | gctcacaatagcgacgaccggactcaacgcaaccgtgacgacgattacgtgtatgag | 960 |
| PANVAC_CEA | ccaccaaaccattcataacaattctaaccagttgaggatgaggagcagtt | 1020 |
| mBN373/420_CEA | ccaccaaaccattcataacaattctaaccagttgaggatgaggagcagtt | 1020 |
| PANVAC_CEA | gcattaacttgtgagcgagattcaaaataccactattatgttgctcaataaccaa | 1080 |
| mBN373/420_CEA | gcattaacttgtgagcgagattcaaaataccactattatgttgctcaataaccaa | 1080 |
| PANVAC_CEA | agttgcggttagccacgcttgcagtgttctaatgatacgcactgcactcctg | 1140 |
| mBN373/420_CEA | agttgcggttagccacgcttgcagtgttctaatgatacgcactgcactcctg | 1140 |
| PANVAC_CEA | tccgttactcgaatgatggagtgtggcattcagaatgaattatccgtc | 1200 |
| mBN373/420_CEA | tccgttactcgcatgatggagtgtggcattcagaatgaattatccgtt | 1200 |
| PANVAC_CEA | gatcactccgaatcactactaccgtccttatgtttgttgtatggccagaccgaccaactatatct | 1260 |
| mBN373/420_CEA | gatcactccgaatcactactaccgtccttatgtttgttgtatggccagaccgaccaactatatct | 1260 |
| PANVAC_CEA | ccatcatacacctactactaccgtccggcgtgaacttgagccttcttgccatgcagcatcg | 1320 |
| mBN373/420_CEA | ccatcatacacctactactaccgtccggcgtgaacttgagccttcttgccatgcagcatcc | 1320 |

Figure 5 (cont.)

```
PANVAC_CEA      actggccgcaataattccatagtcaagagcatcacagtctctgcatctggaacttctcct    2040
mBN373/420_CEA  actggccgcaataattccatagtcaagagcatcacagtctctgcatctggaacttctcct    2040
                ************************************************************

PANVAC_CEA      ggtctctcagctggagccactgtcggcatcatgattggagtgctgttggggttgctctg     2100
mBN373/420_CEA  ggtctctcagctggagccactgtcggcatcatgattggagtgctgttggggttgctctg     2100
                ***********************************************************

PANVAC_CEA      atatag  2106
mBN373/420_CEA  atatag  2106
                ******
```

Figure 8 mBN336 mBN336

Figure 11
mBN373
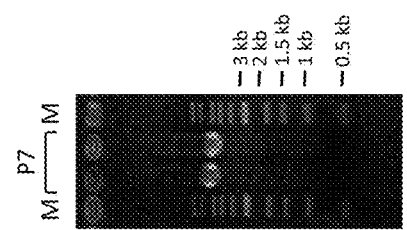
B.
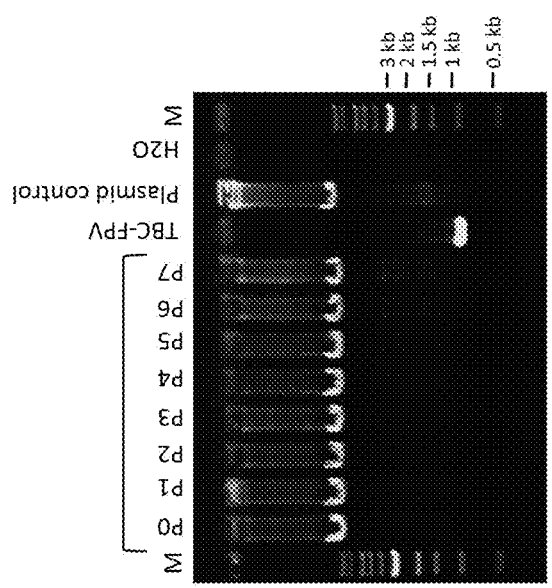
A.

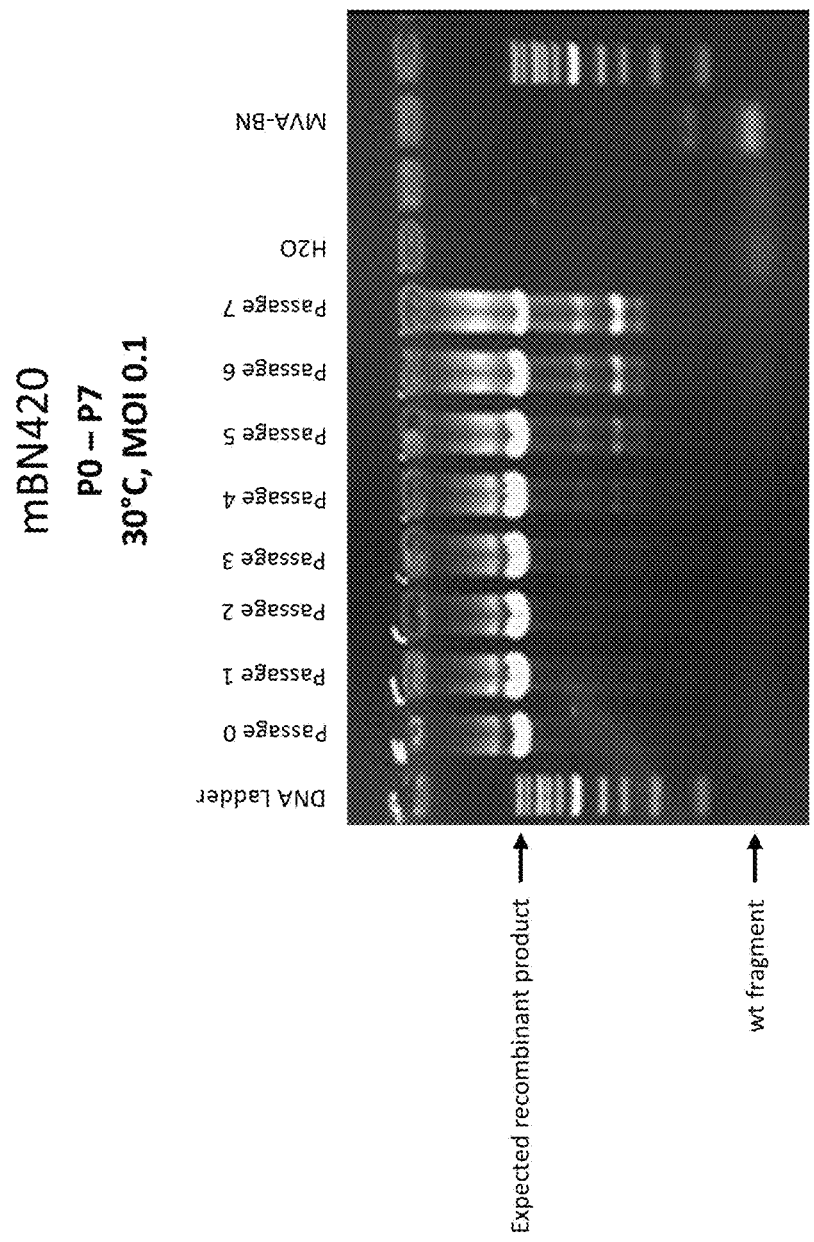

COMPOSITIONS AND METHODS FOR ENHANCING THE STABILITY OF TRANSGENES IN POXVIRUSES

This application is a National Phase application under 35 U.S.C. § 371 of International Application No. PCT/EP2017/074693, filed Sep. 28, 2017, and claims the benefit under 35 U.S.C. § 119(e) of U.S. Provisional Patent Application 62/401,035, filed Sep. 28, 2016, the disclosures of which are incorporated by reference herein in their entirety.

FIELD OF THE INVENTION

The present invention relates to recombinant poxviruses and compositions thereof that comprise a modified Mucin 1, cell surface associated (MUC1) transgene, a human carcinoembryonic antigen (CEA) transgene, and/or one or more costimulatory molecules. In at least one aspect, the modified MUC1, CEA, and/or costimulatory molecule transgenes improve the stability to the poxvirus through successive passaging of the recombinant poxvirus. In additional aspects, the present invention relates to recombinant pox viruses and compositions thereof for use as vaccines and medicinal compositions.

BACKGROUND OF THE INVENTION

Recombinant poxviruses have been used as immunotherapy vaccines against infectious organisms and, more recently, against tumors. Mastrangelo et al. *J Clin Invest.* 2000; 105(8):1031-1034. Two of these poxvirus groups, avipoxvirus and orthopoxvirus, have been shown to be effective at battling tumors and have been involved with potential cancer treatments. Id.

One exemplary avipoxvirus species, fowlpox, has been shown to be a safe vehicle for human administrations as fowlpox virus enters mammalian cells and expresses proteins, but replicates abortively. Skinner et al. *Expert Rev Vaccines.* 2005 Feb. 4(1): 63-76. Additionally, the use of fowlpox virus as a vehicle for expression is being evaluated in numerous clinical trials of vaccines against cancer, malaria, tuberculosis, and AIDS. Id.

Vaccinia, the most well-known of the orthopoxviruses, was used in the world-wide eradication of smallpox and has shown usefulness as a vector and/or vaccine. Recombinant Vaccinia Vector has been engineered to express a wide range of inserted genes, including several tumor associated genes such as p9'7, HER-2/neu, p53 and ETA (Paoletti, et al., 1993).

One poxviral strain that has proven useful as an immunotherapy vaccine against infectious disease and cancer is the Modified Vaccinia Ankara (MVA) virus. MVA was generated by 516 serial passages on chicken embryo fibroblasts of the Ankara strain of vaccinia virus (CVA) (for review see Mayr, A., et al. *Infection* 3, 6-14 (1975)). As a consequence of these long-term passages, the genome of the resulting MVA virus had about 31 kilobases of its genomic sequence deleted and, therefore, was described as highly host cell restricted for replication to avian cells (Meyer, H. et al., *J. Gen. Virol.* 72, 1031-1038 (1991)). It was shown in a variety of animal models that the resulting MVA was significantly avirulent (Mayr, A. & Danner, K., *Dev. Biol. Stand.* 41: 225-34 (1978)).

Strains of MVA having enhanced safety profiles for the development of safer products, such as vaccines or pharmaceuticals, have been described. See International PCT publication WO2002042480 (see also, e.g., U.S. Pat. Nos. 6,761,893 and 6,913,752), all of which are incorporated by reference herein. Such variants are capable of reproductive replication in non-human cells and cell lines, especially in chicken embryo fibroblasts (CEF), but are replication incompetent in human cell lines, in particular including HeLa, HaCat and 143B cell lines. Such strains are also not capable of reproductive replication in vivo, for example, in certain mouse strains, such as the transgenic mouse model AGR 129, which is severely immune-compromised and highly susceptible to a replicating virus. See U.S. Pat. No. 6,761,893. Such MVA variants and its derivatives, including recombinants, referred to as "MVA-BN," have been described. See International PCT publication WO2002042480 (see also, e.g., U.S. Pat. Nos. 6,761,893 and 6,913,752). In the development of cancer immunotherapy vaccines, the tumor antigen MUC1 has been shown to induce and boost a patient's immune response against a variety of cancers when expressed by recombinant poxviruses. See, e.g., Mehebtash et al. *Clin Cancer Res.* 2011 Nov. 15; 17(22):7164-73.

MUC1 (MUC-1, Mucin 1, cell surface associated) (also known as CD227) is a glycoprotein that lines the apical surface of the epithelial cells in the lungs, stomach, intestines, eyes, and several other organs and in a small subset of non-epithelial cells such as hematopoietic cells and activated T cells. Its major function in healthy epithelia is to provide lubrication and a physical barrier against chemical and microbial agents (Hollingsworth and Swanson (January 2004), "Mucins in cancer: protection and control of the cell surface," *Nature Reviews Cancer* 4 (1): 45-60).

MUC1 is anchored to the apical surface by a transmembrane domain (Hattrup and Gendler (2008), "Structure and Function of the Cell Surface (Tethered) Mucins," *Ann. Rev. Physiol.* 70: 431-457). The extracellular domain of MUC1 includes a 20 amino acid variable number tandem repeat (VNTR) domain which is usually heavily glycosylated, with the number of repeats varying from 20 to 120 in different individuals (Brayman et al., (January 2004), "MUC1: a multifunctional cell surface component of reproductive tissue epithelia," *Reprod. Biol. Endocrinol.* 2: 4).

It has been demonstrated that many human carcinomas (such as ovarian, breast, pancreatic, colorectal, and prostate) and hematologic malignancies (multiple myeloma and some B-cell non-Hodgkin's lymphomas) aberrantly overexpress MUC1 (Pecher et al. *Anticancer Res.* 2001 Jul.-Aug. 21:2591-2596). In contrast to its clustered expression in normal tissues, MUC1 is uniformly distributed over the entire surface of tumor cells (Correa et al. *Immunology* January 2003; 108(1): 32-41). Moreover, MUC1 is generally underglycosylated in tumors, exposing novel and potentially antigenic epitopes of the protein core to the immune system (Reis et al. *Int J Cancer.* 1998 Aug. 21; 79(4):402-10).

In view of MUC1 association with human carcinomas, the prior art has attempted to modify MUC1 in order to enhance immunogenicity of the protein. For example, US2006/0147458 (Hamblin et al.) utilized a "codon usage coefficient" in order to design a MUC1 sequence having a reduced homology to native MUC1 as well as having a 7XVNTR segment. US2006/0147458 (Hamblin et al.) created a HSP-70-MUC1 fusion protein in an attempt to enhance immunogenicity. U.S. Pat. No. 5,744,144 (Finn et al.) modified a MUC1 protein by adding two 20 amino acid tandem repeats.

Human carcinoembryonic antigen (CEA) is a 180 kD glycoprotein expressed on the majority of colon, rectal, stomach and pancreatic tumors, some 50% of breast carcinomas, and 70% of lung carcinomas. CEA is also expressed in fetal gut tissue and to a lesser extent on normal colon epithelium. The immunogenicity of CEA has been ambiguous, with several studies-reporting the presence of anti-CEA antibodies in patients, while other studies have not. CEA was first described as a cancer-specific fetal antigen in adenocarcinoma of the human digestive tract in 1965 (Gold and Freeman (1965) *Exp. Med.* 121:439-462). Since that time, CEA has been characterized as a cell surface antigen produced in excess in nearly all solid tumors of the human gastrointestinal tract. The gene for the human CEA protein has been cloned. (Oikawa et al. (1987) *Biochim. Biophys. Res.* 142:511-518; European Application No. EP 0346710).

There is a substantial, unmet medical need for improving cancer treatments. In view of the effectiveness of the MUC1 and CEA antigens in inducing an immune response against cancers, there is a need for improved vaccines able to effectively introduce the antigens to cancer patients.

In addition, there is an increasing need to provide cancer treatments that are able to successfully overcome the hurdles of seeking regulatory approval. In particular, difficulties with large scale production, impurities, and the like can be a significant hurdle in obtaining regulatory approval for treatments and translating those treatments to benefiting patients. At least in one aspect, with the development of the various embodiments of the present invention, difficulties involving large scale production, impurities, and other issues have been successfully overcome.

BRIEF SUMMARY OF THE INVENTION

It was determined in the present invention that various substitutions to MUC1, CEA, and/or TRICOM-encoding nucleic acids in one or more repetitive nucleotide regions enhance the stability of the MUC1, CEA, and/or TRICOM transgenes in recombinant poxviruses.

Accordingly, in one embodiment, the present invention relates to a recombinant poxvirus which is stable through successive passaging of the recombinant poxvirus. The recombinant poxvirus comprises a first nucleic acid encoding a MUC1 peptide having at least two Variable N-Terminal Repeat (VNTR) domains, wherein: a) the arrangement of the at least two VNTR domains are shuffled, and b) the at least two VNTR domains are codon optimized, wherein the recombinant poxvirus is stable through successive passaging.

In one or more preferred embodiments, the recombinant poxvirus comprises a first nucleic acid at least 95% homologous to SEQ ID NO:2 (336 MUC), at least 95% homologous to SEQ ID NO:3 (373 MUC), at least 95% homologous to SEQ ID NO: 4 (399/400 MUC1), or at least 95% homologous to SEQ ID NO: 5 (420 MUC1). In a more preferred embodiment, the recombinant poxvirus comprises a nucleic acid at least 95% homologous to SEQ ID NO: 2 (336 MUC1). In another more preferred embodiment, the recombinant poxvirus comprises a nucleic acid at least 95% homologous to SEQ ID NO:3 (373 MUC).

In yet another preferred embodiment, the recombinant poxviruses further comprises a nucleic acid at least 99% homologous to SEQ ID NOs: 13 or 14 (CEA). In a preferred embodiment, the recombinant poxviruses comprise SEQ ID NOs: 13 or 14.

It is contemplated that the recombinant poxvirus can be any type of poxvirus. In certain embodiments, the poxvirus is an orthopoxvirus or an avipoxvirus. In preferred embodiments, the orthopoxvirus is selected from a vaccinia virus, MVA virus, MVA-BN, and derivatives of MVA-BN. In other more preferred embodiments, the orthopoxvirus is MVA, MVA-BN, or derivatives of MVA-BN. In other preferred embodiments, the avipoxvirus is a fowlpox virus.

In other embodiments, in addition to the MUC1 and/or CEA nucleic acids described herein, the recombinant poxviruses of the present invention include one or more nucleic acids encoding for TRICOM (TRIad of COstimulatory Molecules).

In certain embodiments, the recombinant poxviruses and/or the nucleic acids of the present invention can be used in a heterologous prime-boost dosing regimen. In preferred embodiments, the regimen comprises: a) one or more priming doses of an MVA virus, the MVA virus including one or more of the MUC1, CEA, and/or TRICOM nucleic acids of the present disclosure; and b) one or more boosting doses of a fowlpox virus including one or more of the MUC1, CEA, and/or TRICOM nucleic acids of the present disclosure.

It is contemplated that the recombinant poxviruses, nucleic acids, methods, vaccines, and compositions described herein can be embodied in a kit. Accordingly, in a preferred embodiment, the present invention relates to a composition, vaccine, kit, or a use thereof, comprising: a recombinant orthopoxvirus, such as, but not limited to MVA, the recombinant orthopoxvirus including one or more of the MUC1, CEA, and/or TRICOM nucleic acids of the present disclosure; and a recombinant avipoxvirus, such as but not limited to fowlpox, including one or more of the MUC1, CEA, and/or TRICOM nucleic acids of the present disclosure.

In other embodiments, the present invention relates to one or more methods for generating a recombinant poxvirus encoding for one or more transgenes of the present disclosure that is stable through successive passaging of the recombinant poxvirus.

In one embodiment, there is a method for generating a recombinant poxvirus having a MUC1 transgene that is stable through successive passaging of the recombinant poxvirus, the method comprising: a) providing any one of the nucleic acids or expression cassettes of the present disclosure; and b) inserting the nucleic acid or the expression cassette into a recombinant poxvirus.

In another embodiment, there is a method for generating a recombinant poxvirus that is stable through successive passaging comprising: a) providing a first nucleic acid sequence encoding a MUC1 peptide having at least two Variable N-Terminal Repeat (VNTR) domains, wherein the arrangement of the at least two VNTR domains are shuffled, and the at least two VNTR domains are codon optimized; and b) providing a second nucleic acid encoding a CEA peptide, wherein the second nucleic acid comprises at least one nucleotide substitution in at least one repetitive nucleotide region of the second nucleic acid, wherein the at least one repetitive nucleotide region is defined as a) three or more consecutively repeated G or C nucleotides and/or b) three or more consecutively repeated T nucleotides; wherein the recombinant poxvirus is stable through successive passaging.

Additional objects and advantages of the invention will be set forth in part in the description which follows, and in part will be obvious from the description or may be learned by practice of the invention. The objects and advantages of the invention will be realized and attained by means of the elements and combinations particularly pointed out in the appended claims.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

FIGS. 2A and 2B depicts the amino acid sequences of MUC1 and the shuffling of the VNTR domain repeats according to various embodiments of the invention. FIG. 2A) The MUC1 amino acid as found in PANVAC (SEQ ID NO: 6). Illustrated are the 6 VNTRs found in the PANVAC MUC1. FIG. 2B) The MUC1 amino acid as found in mBN336, mBN373, and mBN420 (SEQ ID NO: 30). Illustrated are the 3VNTRs found in mBN336, mBN373, and mBN420 MUC1. Underlined amino acids represent amino acids modified to form the agonist epitopes of WO 2013/103658.

FIGS. 3A-3C depict pairwise alignments and an exemplary codon optimization of the MUC1 VNTR domain repeats according to various embodiments of the invention. FIG. 3A) Alignment of the PANVAC VNTR #2 (SEQ ID NO: 7) and the mBN336, mBN373, mBN420 VNTR #1 (SEQ ID NO: 8). FIG. 3B) Alignment of the PANVAC VNTR #1 (SEQ ID NO: 9) and the mBN336, mBN373, mBN420 VNTR #2 (SEQ ID NO: 10). FIG. 3C) Alignment of the PANVAC VNTR #3 (SEQ ID NO: 11) and the mBN336, mBN373, mBN420 VNTR #3 (SEQ ID NO: 12). Underlined nucleotides represent nucleotide regions modified to form the agonist epitopes of WO 2013/103658.

FIGS. 4A-4C depict pairwise alignments of the MUC1 coding sequences, as compared to PANVAC, used in the recombinant poxvirus based constructs in accordance with the present invention. FIG. 4A) MUC1 PANVAC (SEQ ID NO:1) versus MUC1 mBN336 (SEQ ID NO:2). FIG. 4B) MUC1 PANVAC (SEQ ID NO:1) versus MUC1 mBN373 (SEQ ID NO:3). FIG. 4C) MUC1 PANVAC (SEQ ID NO:1) versus MUC1 mBN420 (SEQ ID NO:5). Exemplary repetitive regions comprising one or more substitutions are underlined.

FIG. 5 depicts a pairwise alignment of the CEA coding sequence of mBN373 and mBN420 (SEQ ID NO: 14), as compared to CEA of PANVAC (SEQ ID NO: 13), used in the recombinant poxvirus based constructs in accordance with the present invention. Exemplary repetitive regions comprising one or more substitutions are underlined.

FIG. 6 depicts a pairwise alignment of the B7-1 coding sequence of mBN373 and mBN420 (SEQ ID NO: 15), as compared to B7-1 of PANVAC (SEQ ID NO:16), as compared to PANVAC, used in the recombinant poxvirus based constructs in accordance with the present invention. Exemplary repetitive regions are illustrated by the shown substitutions (non*regions of the alignment).

FIG. 7 depicts a pairwise alignment of an ICAM-1 coding sequence of mBN373 and mBN420 (SEQ ID NO: 18), as compared to PANVAC (SEQ ID NO:19), as compared to PANVAC, used in the recombinant poxvirus based constructs in accordance with the present invention. Exemplary repetitive regions are illustrated by the shown substitutions (non*regions of the alignment).

FIG. 8 depicts a pairwise alignment of an LFA-3 coding sequence of mBN373 and mBN420 (SEQ ID NO: 21), as compared to PANVAC (SEQ ID NO: 22), as compared to PANVAC, used in the recombinant poxvirus based constructs in accordance with the present invention. Exemplary repetitive regions are illustrated by the illustrated substitutions (non*regions of the alignment).

FIG. 9A) PCR results for stability of CEA over seven passages representative for passages during and beyond production of Clinical Trial Material (CTM)/GMP material. FIG. 9B) PCR results for stability of MUC1 over seven passages representative for passages during and beyond production of CTM/GMP material. FIG. 9C) PCR results for the stability of the TRICOM over 7 passages representative for passages during and beyond production of CTM/GMP material. The recombination plasmids used for generation of MVA-mBN336B were used as positive controls, MVA-BN was used as negative control (empty vector backbone) and H$_2$O was used as control for the PCR reaction.

FIG. 10A) PCR amplification of Passage 7 samples send for analysis by sequencing. Individual PCR amplifications were performed for each individual transgenes: CEA, MUC1, and TRICOM. FIG. 10B) Electropherograms of the MUC1 nt-sequence depicting the loci containing the detected point mutation leading to a frame shift originating in passage 5.

FIGS. 11A and 11B illustrate experiments analyzing stability of a MUC1 transgene in mBN373. FIG. 11A) PCR analysis of the inserted transgenes for each passage. The recombination plasmid used for generation of FPV-mBN373B was used as positive control, FPV (strain TBC-FPV) was used as negative control. FIG. 11B) PCR analysis of FPV-mBN373B at passage seven resulted in the expected band size of 5566 bp (PCR1) and 5264 bp (PCR2) covering the inserted transgenes and each inserted flanking region. Sequence analysis confirmed genetic stability of the recombinant after 7 passages, being representative for passages during and beyond production of CTM/GMP material.

FIG. 12 is a PCR analysis that analyzes the stability of the MUC1, CEA, and TRICOM transgenes in mBN420. Shown is the result of the PCR amplicon of the used site for integration of all five transgenes within the MVA-BN genome (IGR88/89). Highlighted is the height of the expected PCR fragment and a potential wt-fragment. Several deletion fragments of smaller size can be detected and are enriched during repeated passaging at 30° C. Results are shown for passage 0 to 7 of mBN420.

All Pairwise alignments illustrated in the Figures were conducted using the Clustal Omega sequence Alignment tool, available at the EMBL-EBI website, at www.ebi.ac.uk/Tools/msa/clustalo.

DETAILED DESCRIPTION OF THE INVENTION

It is to be understood that both the foregoing Summary and the following detailed description are exemplary and explanatory only and are not restrictive of the invention, as claimed.

PANVAC employs a heterologous prime-boost strategy using the recombinant poxviruses of vaccinia (PANVAC-V) and fowlpox (PANVAC-F), each expressing the transgenes MUC1, CEA, and TRICOM. PANVAC has been shown to be effective in treating cancer and is currently in clinical trials for various cancers, including colorectal cancer, ovarian cancer, breast cancer, and bladder cancer. MVA-CV301 is another heterologous vaccine combination undergoing clinical trials (see, e.g., Gulley et al., Clin Cancer Res 2008; vol. 14:10, Tsang et al. Clin Cancer Res 2005; vol. 11). MVA-CV301 employs a heterologous prime-boost strategy using MVA and fowlpox, each expressing the transgenes MUC1, CEA, and TRICOM.

While PANVAC and MVA-CV301 are effective in treating cancer, the transgenes of the PANVAC recombinant poxviruses become less stable with successive passaging and production of the viruses. Shown in Tables 1 and 2, after successive passaging of the PANVAC-V and PANVAC-F, the percentage of viruses expressing the MUC1 and CEA steadily decreases.

Figure 1:
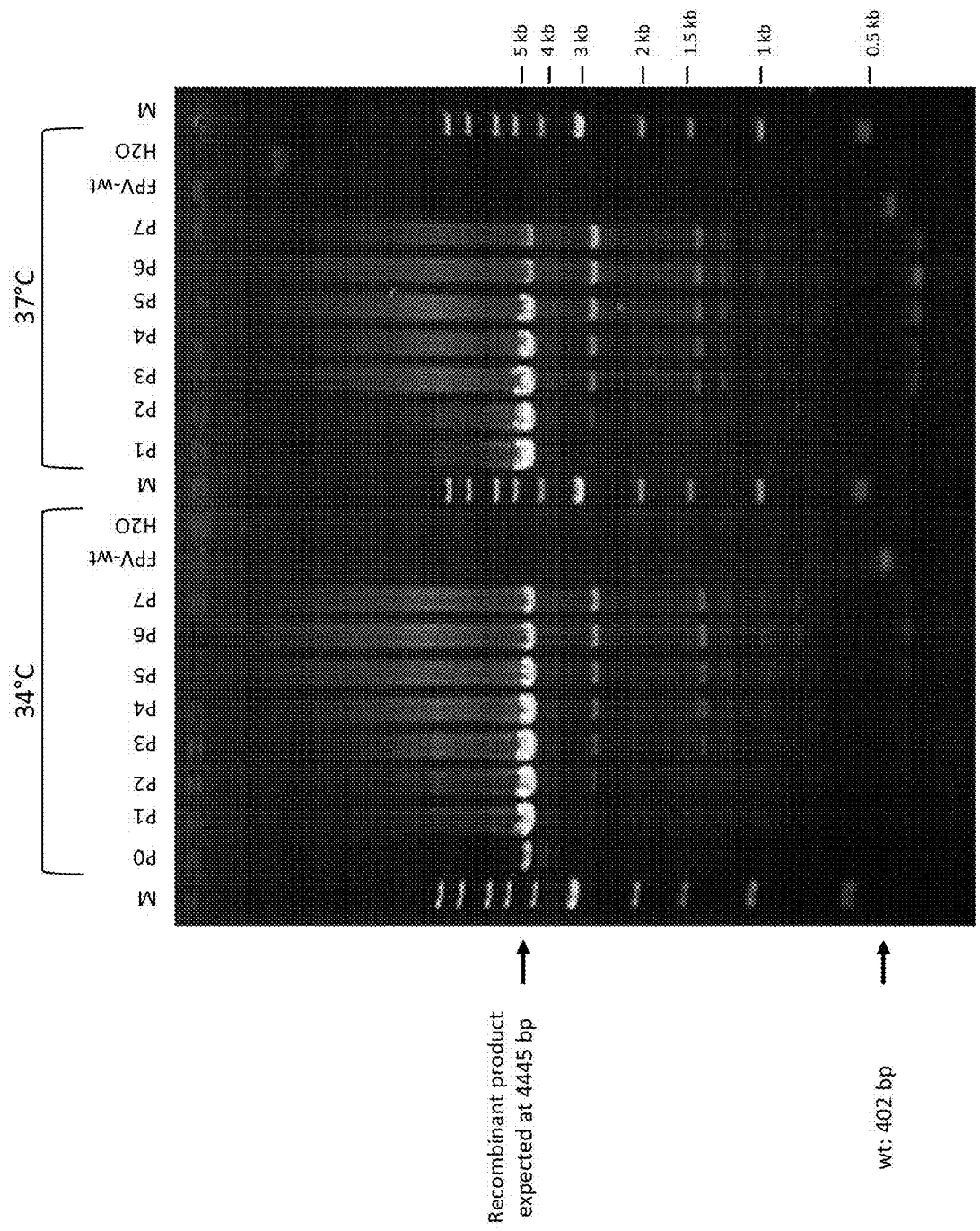
FIG. 1 is a PCR analysis that illustrates the instability of the transgenes of PANVAC (MUC1 and CEA). Shown are the results of the PCR amplicon of the site used for integration of MUC1 and CEA within the TBC-FPV genome (IGR61/62). Highlighted is the height of the expected PCR fragment and a potential wt-fragment. Several deletion fragments of smaller size can be detected and are enriched during repeated passaging at either 34° C. or 37° C. Results are shown for passage 0 to 7 of PANVAC-F.

In at least one aspect, the decrease in expression of MUC1 and/or CEA appears to be a result of an at least partial loss of the MUC1 and/or CEA transgenes. FIG. 1 illustrates the loss of the MUC and CEA transgenic sequence of PANVAC. In FIG. 1, Recombinant PANVAC-F product was expected to be at 4445 bp. However, as illustrated, experiments showed the presence of multiple lesser-sized fragments, which were confirmed to be fragmented sequences of MUC1 and CEA (data not shown). The loss of expression and instability of the MUC1 transgene and of the previous recombinant poxviruses hinder the production and the purity of the CV301 recombinant poxviruses.

Prior to creating the various nucleic acids and recombinant poxviruses of the present invention, in order to stabilize the transgenes, the inventors made multiple attempts to customize and/or modify the recombinant vaccinia, recombinant MVA, and recombinant fowlpox viruses of PANVAC and MVA-CV301. Shown in Tables 3 and 4, modifications to the transgenes and/or the recombinant vaccinia, recombinant MVA, and recombinant fowlpox viruses included: (i) alternating or modifying into which intergenic regions (IGRs) the transgenes were inserted, (ii) optimizing the codons of one or more transgenes, (iii) varying transgene promoters, and (iv) modifying the numbers and arrangements of VNTR regions in the MUC1 transgene. As described in the tables, many of the constructs failed to be stably generated due to either loss-of-function mutations or fragment deletions resulting in loss of transgene expression.

TABLE 1

Percent of Expressing Plaques in PANVAC-V MVB1, MVB2 and Passages

| | | Mean Percentage of Expressing Plaques (%) | | | | |
|---|---|---|---|---|---|---|
| Protein | MVB | MVB | Passage 1* | Passage 2* | Passage 3* | Passage 4* |
| CEA | 1 | 99.5 | 99.8 | 98.3 | 94.7 | 90.0 |
| | 2 | 100.0 | 97.6 | 95.1 | 91.8 | 89.0 |
| MUC1 | 1 | 99.8 | 99.3 | 95.0 | 91.6 | 83.0 |
| | 2 | 99.7 | 98.2 | 95.9 | 86.3 | 73.6 |
| B7.1 | 1 | 99.9 | 99.9 | 99.7 | 99.4 | 97.7 |
| | 2 | 99.9 | 100.0 | 99.9 | 99.8 | 99.1 |
| ICAM-1 | 1 | 99.8 | 99.5 | 98.8 | 98.6 | 97.5 |
| | 2 | 99.6 | 99.4 | 99.1 | 98.2 | 98.2 |
| LFA-3 | 1 | 100.0 | 99.9 | 99.7 | 99.5 | 98.5 |
| | 2 | 100.0 | 99.6 | 99.9 | 99.8 | 99.1 |

*Each number represents the mean values obtained from three independent passage experiments.

TABLE 2

Percent of Expressing Plaques in PANVAC-F MVB1, MVB2 and Passages

| | | Mean Percentage of Expressing Plaques (%) | | | | |
|---|---|---|---|---|---|---|
| Protein | MVB | MVB | Passage 1* | Passage 2* | Passage 3* | Passage 4* |
| CEA | 1 | 99.2 | 99.5 | 96.1 | 80.4 | 54.9 |
| | 2 | 100.0 | 99.4 | 98.8 | 89.8 | 63.9 |
| MUC1 | 1 | 99.7 | 99.3 | 95.3 | 75.7 | 44.3 |
| | 2 | 99.6 | 99.8 | 98.3 | 89.4 | 55.4 |
| B7.1 | 1 | 100.0 | 100.0 | 100.0 | 99.8 | 99.8 |
| | 2 | 99.5 | 99.2 | 99.7 | 100.0 | 99.5 |
| ICAM-1 | 1 | 100.0 | 99.9 | 99.8 | 99.4 | 99.5 |
| | 2 | 99.8 | 99.5 | 99.7 | 100.0 | 99.9 |
| LFA-3 | 1 | 100.0 | 100.0 | 100.0 | 100.0 | 99.9 |
| | 2 | 100.0 | 99.9 | 99.7 | 100.0 | 100.0 |

*Each number represents the mean values obtained from three independent passage experiments.

TABLE 3

| Construct name | Construct Attempts - MVA Virus Construct details | Results |
|---|---|---|
| MVA-mBN247 | MUC/CEA/TRICOM in IGR148/149 Promoters & TGs exactly as in PANVAC-V | Generation failed |
| MVA-mBN269 | CEA only (as in PANVAC-V) in IGR148/149 | Stable |
| MVA-mBN317 | CEA with optimized codon usage in IGR44/45 TRICOM unchanged in IGR148/149 | Loss of CEA during generation of the construct |
| MVA-mBN329 | CEA (as in PANVAC-V) in IGR44/45 TRICOM unchanged in IGR148/149 | Generation successful Stable expression of TGs for 7 passages at 30° C. & 37° C. (FACS by BN-CVD) |
| MVA-mBN332 | MUC1-C3-opt6VNTRs in IGR88/89 CEA (as in PANVAC-V) in IGR44/45 TRICOM (as in PANVAC-V) in IGR148/149 | Generation failed |
| MVA-mBN335 | MUC1-C5-opt6VNTRs-SignMut in IGR88/89 CEA (as in PANVAC-V) in IGR44/45 TRICOM (as in PANVAC-V) in IGR148/149 | Generation failed |

TABLE 4

| Construct name | Construct Attempts - Fowlpox Virus Construct details | Results |
|---|---|---|
| FPV-mBN285 | CEA & TRICOM in BamJ (different to PANVAC-F) Promoters & TGs exactly as in PANVAC-F | Generation failed |
| FPV-mBN318 | FPV-mBN285 + MUC1-C3-opt6VNTRs-SignMut in IGR61/62 | Generation failed |
| FPV-mBN319 | FPV-mBN285 + MUC1-C14-opt3VNTRs-SignMut in IGR61/62 | Generation failed |
| FPV-mBN322 | FPV-mBN285 + MUC1-C5-opt6VNTRs in IGR61/62 | Generation failed |
| FPV-mBN338 | FPV-mBN285 + MUC1-C5-opt6VNTRs-SignMut in IGR61/62 | Generation failed |
| FPV-mBN339 | FPV-mBN285 + MUC1-C13-opt3VNTRs in IGR61/62 | Generation failed |
| FPV-mBN351 | MUC1-C13-opt3VNTRs only in IGR61/62 | Weak MUC-1 Expression |
| FPV-mBN352 | MUC1/CEA/TRICOM in BamJ with FPV-40K promoter for MUC1-C13-opt3VNTRs | Single nucleotide mutations in CEA occurred repeatedly |
| FPV-mBN353 | FPVmBN285 + (FPV-40K promoter)-MUC1-C13-opt3VNTRs reverse orientation to ORFs of IGR61/62 | Immediate loss of MUC1 with MUC1 in |
| FPV-mBN362 | FPV-mBN351 & FPVmBN285 co-infection (PrS)-MUC1-C13-opt3VNTRs in IGR61/62 & TRICOM in BamJ | Single nucleotide mutations in CEA occurred repeatedly |

After these multiple attempts, MVA-mBN336 was constructed. As described herein, MVA-mBN336 is an MVA-CV301 recombinant poxvirus including a modified MUC1, a CEA, and modified TRICOM transgenes. Shown in FIGS. 9 and 10, MVA-mBN336 demonstrated transgene stability as compared to PANVAC (see FIG. 1 and Table 1). Shown in FIG. 10, the MVA-mBN336 showed stability of all of the transgenes (MUC1, CEA, and TRICOM) through Passage 4. Starting at Passage 5, a frameshift mutation was detected within a minor population of the analyzed material. The stability illustrated through passage 4 demonstrates the ability of the MVA-mBN336 to overcome the stability problems associated with PANVAC and other attempts to generate a stable poxvirus including MUC1. The stability of MVA-mBN336 is additionally advantageous, as manufacture and larger scale production of MVA-based vaccines are typically taken from MVAs at passage 3 or passage 4. Thus, because MVA-mBN336 is stable through passage 4, large scale production can begin and significant regulatory hurdles with regard to stability can be overcome.

To address and correct the instability problems, the nucleic acids of the present invention were synthesized and provide for one or more nucleic acids that encode for a MUC1 transgene, CEA transgene, and the TRICOM transgenes. As shown by the present disclosure, the MUC1, CEA, and the TRICOM nucleic acids of the present invention result in an improved genetic stability of the recombinant poxvirus and the transgenes included therein through successive passaging of the recombinant poxviruses.

Thus, in various embodiments, the present invention provides a recombinant poxvirus having one or more novel nucleic acids that encode the MUC1, CEA, and/or TRICOM antigens. As provided in more detail herein, in at least one aspect, when incorporated as part of a recombinant poxvirus, the one or more modified MUC1-, CEA-, and/or TRICOM-encoding nucleic acid sequences improve the stability and presence of transgenes in the recombinant poxvirus.

Definitions

As used herein, the singular forms "a," "an," and "the" include plural references unless the context clearly indicates otherwise. Thus, for example, reference to "a nucleic acid" includes one or more of the nucleic acid and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps. When used herein, the term "comprising" can be substituted with the term "containing" or "including" or sometimes when used herein with the term "having." Any of the aforementioned terms (comprising, containing, including, having), though less preferred, whenever used herein in the context of an aspect or embodiment of the present invention can be substituted with the term "consisting of." When used herein, "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning and therefore satisfy the requirement of the term "and/or" as used herein. Concurrent applicability of more than one of the options is also understood to fall within the meaning and therefore satisfy the requirement of the term "and/or."

"Mutation" is as defined herein any modification to a nucleic acid, such as deletions, additions, insertions, and/or substitutions.

"Costimulatory molecules" as used herein are molecules that, when bound to their ligand, deliver a second signal such that a T cell can become activated. The most well-known costimulatory molecule on the T cell is CD28, which binds to either B7-1 (also called B7.1 or CD80) or B7-2 (also known as CD86). An additional costimulatory molecule is B7-3. Accessory molecules that also provide a second signal for the activation of T cells include intracellular adhesion molecule (ICAM-1 and ICAM-2) and leukocyte function associated antigen (LFA-1, LFA-2 and LFA-3). Integrins and tumor necrosis factor (TNF) superfamily members can also serve as co-stimulatory molecules.

"Genetic stability," "stability," "Stability of expression," "stable through successive passaging," "stability through successive passaging," or "stability of expression through successive passaging" of the recombinant poxviruses when used herein in conjunction with the recombinant poxvirus, MUC1, CEA, TRICOM, and other transgenes is understood to mean that transgenic nucleotide sequences of the recombinant poxvirus remain materially intact and/or materially unchanged through successive passaging of the recombinant poxvirus until at least at Passage 3 or Passage 4. A recombinant poxvirus having stability at least through Passage 3 or Passage 4 is particularly important as the final product generated by large scale manufacture and production of poxviruses are typically Passage 3 or Passage 4. "Materially intact and/or materially unchanged" means the absence of single or fragment mutations (e.g., including substitutions, deletions, etc.) that cause a constant decrease of expression of the transgene as the number of passages increase. For example, as shown in Tables 1 and 2, the expression levels of the various transgenes of PANVAC decreased as the number of passages increased. There is a variety of ways known in the art in which genetic stability or stability of transgenes can be analyzed, including, but not limited to, the assays described in Examples 2 through 4 of the instant application. Additional ways known in the art to measure stability include, but are not limited to, PCR, FACS, measurement of transgene co-expression by FACS, and so forth.

A "host cell" as used herein is a cell that has been introduced with a foreign molecule, virus, or microorganism for the purpose of development and/or production of the foreign molecule, virus, or microorganism. In one non-limiting example, as described herein, a cell of a suitable cell culture such as, e.g., CEF cells, can be infected with a poxvirus or, in other alternative embodiments, with a plasmid vector comprising a foreign or heterologous gene. Thus, the suitable cell cultures serve as a host to a poxvirus and/or foreign or heterologous gene.

"Percent (%) sequence homology or identity" with respect to nucleic acid sequences described herein is defined as the percentage of nucleotides in a candidate sequence that are identical with the nucleotides in the reference sequence (i.e., the nucleic acid sequence from which it is derived), after aligning the sequences and introducing gaps, if necessary, to achieve the maximum percent sequence identity, and not considering any conservative substitutions as part of the sequence identity. Alignment for purposes of determining percent nucleotide sequence identity or homology can be achieved in various ways that are within the skill in the art, for example, using publicly available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

For example, an appropriate alignment for nucleic acid sequences is provided by the local homology algorithm of Smith and Waterman, (1981), Advances in Applied Mathematics 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), Nucl. Acids Res. 14(6):6745-6763.

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the NCBI website, at blast.ncbi.nlm.nih.gov.

The term "prime-boost vaccination" or "prime-boost regimen" refers to a vaccination strategy or regimen using a first priming injection of a vaccine targeting a specific antigen followed at intervals by one or more boosting injections of the same vaccine. Prime-boost vaccination may be homologous or heterologous. A homologous prime-boost vaccination uses a vaccine comprising the same antigen and vector for both the priming injection and the one or more boosting injections. A heterologous prime-boost vaccination uses a vaccine comprising the same antigen for both the priming injection and the one or more boosting injections but different vectors for the priming injection and the one or more boosting injections. For example, a homologous prime-boost vaccination may use a recombinant poxvirus comprising nucleic acids expressing one or more antigens for the priming injection and the same recombinant poxvirus expressing one or more antigens for the one or more boosting injections. In contrast, a heterologous prime-boost vaccination may use a recombinant poxvirus comprising nucleic acids expressing one or more antigens for the priming injection and a different recombinant poxvirus expressing one or more antigens for the one or more boosting injections.

The term "recombinant" means a polynucleotide of semi-synthetic, or synthetic origin which either does not occur in nature or is linked to another polynucleotide in an arrangement not found in nature.

"Successive Passaging" as used herein relates to the production of recombinant viruses through the use of cell passaging. By way of example only, host cells are infected with a virus or recombinant virus in an initial passage. Viruses replicate and are produced in the initial passage. After infection and cultivation of host cells, viruses are harvested from the host cells and collected in a cell/viral suspension. This procedure is typically repeated multiple times in subsequent cell passages, each passage producing and replicating more recombinant viruses.

As used herein, a "transgene" or "heterologous" gene is understood to be a nucleic acid or amino acid sequence which is not present in the wild-type poxviral genome (e.g., vaccinia, fowlpox, or MVA). The skilled person understands that a "transgene" or "heterologous gene," when present in a poxvirus, such as Vaccinia Virus, is to be incorporated into the poxviral genome in such a way that, following administration of the recombinant poxvirus to a host cell, it is expressed as the corresponding heterologous gene product, i.e., as the "heterologous antigen" and\or "heterologous protein." Expression is normally achieved by operatively linking the heterologous gene to regulatory elements that allow expression in the poxvirus-infected cell. Preferably, the regulatory elements include a natural or synthetic poxviral promoter.

"TRICOM." Triad of COstimlatory Molecules (also known as TRICOM) includes B7-1 (also known as B7.1 or CD80), intracellular adhesion molecule-1 (ICAM-1, also known as CD54) and lymphocyte function-associated antigen-3 (LFA-3, also known as CD58), and commonly included in recombinant viral vectors (e.g., poxviral vectors) expressing a specific antigen in order to increase the antigen-specific immune response. The individual components of TRICOM can be under the control of the same or different promoters, and can be provided on the same vector with the specific antigen or on a separate vector. Exemplary vectors are disclosed, for example, in Hodge et al., "A Triad of Costimulatory Molecules Synergize to Amplify T-Cell Activation," Cancer Res. 59:5800-5807 (1999) and U.S. Pat. No. 7,211,432 B2, both of which are incorporated herein by reference.

A "vector" refers to a DNA or RNA plasmid or virus that can comprise a heterologous polynucleotide. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

Novel MUC1 Nucleic Acid Sequences

With the development of the present invention, the inventors determined that over the course of passaging the recombinant poxviruses, in particular the orthopoxviruses (e.g., vaccinia virus, MVA, MVA-BN) and the avipoxviruses (e.g., fowlpox virus), one or more of the regions of the nucleic acids encoding for MUC1, CEA, and/or TRICOM became mutated (e.g., deleted, substituted, etc.), thereby contributing to the instability of the recombinant poxvirus and transgenes therein.

Modifications to the VNTR Regions

As noted previously, the VNTR region is an extracellular domain of MUC1 that includes a 20-amino-acid variable number tandem repeat (VNTR) domain with the number of repeats varying from 20 to 120 in different individuals. See, Brayman et al. While the amino acid sequence of the VNTR domains typically are identical (see, e.g., FIG. 2A), the nucleotide sequence of the VNTRs can vary. Shown in FIG. 2A, as part of PANVAC, MUC1 was synthesized to have 6 VNTRs.

In one aspect, over the course of the development of the present invention, it was determined that one or more modifications to the nucleic acids encoding the MUC1 VNTR region improved the stability of the MUC1 transgene in a recombinant poxvirus. More particularly, the inventors determined that shuffling the nucleic acids encoding the VNTRs further enhanced the stability of the MUC1 transgene as compared to PANVAC MUC1. As used herein "shuffling" the VNTRs is defined as rearranging the order of the nucleic acids encoding the VNTR domain repeats. Illustrated in FIGS. 2A and 2B is a non-limiting example of shuffling the VNTRs. In FIG. 2A, the order of the PANVAC VNTR domains is shown as VNTR #s 1-6. Looking at FIG. 2B, the nucleic acid encoding VNTR #1 of mBN336, mBN373, mBN420 corresponds with what is VNTR #2 in PANVAC. VNTR #2 of mBN336, mBN373, mBN420 corresponds with what is VNTR #1 in PANVAC. Thus, in synthesizing the MUC1 of mBN336, mBN373, and mBN420, the order of PANVAC VNTRs #1 and 2 were shuffled.

It is understood by the present invention that the VNTR domains shown in FIGS. 2A and 2B are merely representative of the MUC1 VNTR domains and that the numbers of VNTR domains and arrangements in which the VNTRs are shuffled can vary.

In addition to shuffling the VNTRs, it was determined that optimizing the codons of the VNTR domains further enhanced the stability of the MUC1 transgene. As used herein, "optimizing the codons" of the VNTRs is defined as substituting one or more nucleotides of the VNTRs in order to minimize the chance of mutations and/or deletions to the nucleotide sequences of the VNTRs due to the homology of the repetitive nucleotide sequences.

In a more specific embodiment, depicted in the alignments of FIGS. 3A-3B, one or more of the nucleic acids of the present invention include various substitutions in the VNTR domains. Shown in FIG. 3A, VNTR1 of mBN373 and mBN420 (hereinafter mBN373/420) comprises one or more nucleotide sequences encoding an agonist epitope from WO 2013/103658 (region indicated by underlining) in addition to the illustrated codon optimization substitutions. Shown in FIGS. 3B and 3C, VNTRs 2 and 3 of mBN373/420 modification comprise the illustrated codon optimization substitutions.

It is understood by the present invention that the illustrated codon optimization modifications to VNTR domains shown in FIGS. 3A-3C are merely representative of the MUC1 VNTR domain codon optimizations. By way of example only, it is contemplated by the present invention that alternative nucleotides may be substituted at the particular points of modification in the VNTR domains. It is additionally contemplated that the particular points of the modification in the VNTR domains may vary such that the modification is a silent modification. A silent modification, as used herein, means that the modification does not affect the amino acid sequence of the MUC1 antigen.

Thus, in one embodiment, the MUC1 nucleic acids of the present invention comprise one or more VNTR domain regions that are 1) shuffled and 2) codon optimized.

Modifications to Non-VNTR Regions of MUC1

In another aspect of the present invention, one more modifications were made to those regions outside of the VNTR domains. In a more specific aspect, over the course of the development of the present invention, it was determined that one or more modifications in those nucleotide regions outside of the MUC1 VNTR region (non-VNTR regions) improved the stability of the MUC1 transgene. A representative sample of those regions (underlined nucleotides) is illustrated below. The VNTR region is shaded gray.

[SEQ ID NO: 1]

```
ATGACACCGG GCACCCAGTC TCCTTTCTTC CTGCTGCTGC TCCTCACAGT GCTTACAGTT   60

GTTACGGGTT CTGGTCATGC AAGCTCTACC CCAGGTGGAG AAAAGGAGAC TTCGGCTACC  120

CAGAGAAGTT CAGTGCCCAG CTCTACTGAG AAGAATGCTG TGAGTATGAC AAGCTCCGTA  180

CTCTCCAGCC ACAGCCCCGG TTCAGGCTCC TCCACCACTC AGGGACAGGA TGTCACTCTG  240

GCCCCGGCCA CGGAACCAGC TTCAGGTTCA GCTGCCTTGT GGGGACAGGA TGTCACCTCG  300

GTACCAGTTA CTAGACCAGC TTTAGGTAGC ACAGCACCTC CTGCTCATGG AGTAACTAGT  360

GCTCCTGATC CTCGTCCAGC TCCTGGCAGT ACTGCACCAC CGGCACATGG CGTAACATCA  420

GCACCTGATA CAAGACCTGC ACCTGGATCT ACAGCGCCGC CTGCGCACGG AGTGACATCG  480

GCGCCCGATA CGCGCCCCGC TCCCGGTAGC ACCGCACCGC CCGCCCACGG TGTTACAAGT  540

GCACCCGATA CCCGGCCGGC ACCCGGAAGT ACCGCTCCAC CTGCACACGG GGTCACAAGC  600

GCGCCAGACA CTCGACCTGC GCCAGGGTCG ACTGCCCCTC CGGCGCATGG TGTGACCTCA  660

GCTCCTGACA CAAGGCCAGC CCCAGCTAGC ACTCTGGTGC ACAACGGCAC CTCTGCCAGG  720

GCTACCACAA CCCCAGCCAG CAAGAGCACT CCATTCTCAA TTCCCAGCCA CCACTCTGAT  780

ACTCCTACCA CCCCTTGCCAG CCATAGCACC AAGACTGATG CCAGTAGCAE TCACCATAGC  840

ACGGTACCTC CTCTCACCTC CTCCAATCAC AGCACTTCTC CCCAGTTGTC TACTGGGGTC  900

TCTTTCTTTT TCCTGTCTTT TCACATTTCA AACCTCCAGT TTAATTCCTC TCTGGAAGAT  960

CCCAGCACCG ACTACTACCA AGAGCTGCAG AGAGACATTT CTGAAATGTT TTTGCAGATT 1020

TATAAACAAG GGGGTTTTCT GGGCCTCTCC AATATTAAGT TCAGGCCAGG ATCTGTGGTG 1080

GTACAATTGA CTCTGGCCTT CCGAGAAGGT ACCATCAATG TCCACGACGT GGAGACACAG 1140
```

-continued

```
TTCAATCAGT ATAAAACGGA AGCAGCCTCT CGATATAACC TGACGATCTC AGACGTCAGC 1200

GTGAGTGATG TGCCATTTCC TTTCTCTGCC CAGTCTGGGG CTGGGGTGCC AGGCTGGGGC 1260

ATCGCGCTGC TGGTGCTGGT CTGTGTTCTG GTTGCGCTGG CCATTGTCTA TCTCATTGCC 1320

TTGGCTGTCT GTCAGTGCCG CCGAAAGAAC TACGGGCAGC TGGACATCTT TCCAGCCCGG 1380

GATACCTACC ATCCTATGAG CGAGTACCCC ACCTACCACA CCCATGGGCG CTATGTGCCC 1440

CCTAGCAGTA CCGATCGTAG CCCCTATGAG AAGGTTTCTG CAGGTAATGG TGGCAGCAGC 1500

CTCTCTTACA CAAACCCAGC AGTGGCAGCC ACTTCTGCCA ACTTGTAG               1548
```

To generate a recombinant poxvirus which is stable through successive passaging of the virus, the one or more nucleic acids of the present invention were synthesized. More particularly, illustrated in FIGS. 2A through 2B, one or more substitutions were made to one or more of the underlined areas outside of the VNTR regions of the PANVAC MUC1 (SEQ ID NO:1), as shown.

Thus, in one embodiment of the invention, there is a novel MUC1 nucleic acid that comprises a substitution to at least one of the repetitive nucleotide regions outside of the VNTR regions of the MUC1 nucleic acid. In at least one aspect, one or more of the repetitive regions are defined as: (i) three or more consecutively repeated nucleotides; (ii) three or more consecutive G or C nucleotides; and/or (iii) three or more consecutive T or C nucleotides. In more specific aspects, one or more of repetitive nucleotide regions is further defined as (i) four or more consecutively repeated nucleotides, (ii) four or more consecutive G or C nucleotides, and/or (iii) four or more consecutive T or C nucleotides. In certain other more specific aspects, the consecutively repeated nucleotides are defined as (i) consecutive G nucleotides, (ii) consecutive C nucleotides, and/or (iii) consecutive T nucleotides.

As shown by FIGS. 2A through 2B, the novel MUC1 nucleic acid can comprise a substitution in at least 2, 3, 4, or 5 repetitive nucleotide regions outside of the VNTR regions of the MUC1 nucleic acid. In further aspects, the novel MUC1 nucleic acid can comprise a substitution in at least 10, 15, 20, or 25 repetitive nucleotide regions outside of the VNTR regions.

In still additional aspects, the novel MUC1 nucleic acid can comprise at least one substitution in those regions outside of the VNTR regions that are more prone to mutate over successive passaging of the recombinant poxvirus. In an exemplary aspect, the novel MUC1 nucleic acid can comprise at least one substitution in one or more of those MUC1 nucleotide repetitive regions outside of the VNTR regions selected from the nucleotide regions and/or combinations thereof of PANVAC MUC1 (SEQ ID NO:1) shown in Table 5.

TABLE 5

| 7-16 | 19-32 | 40-45 | 65-68 | 122-128 | 136-138 |
|---|---|---|---|---|---|
| 194-200 | 207-213 | 222-224 | 240-253 | 296-299 | 705-714 |
| 731-734 | 761-765 | 770-773 | 791-795 | 847-864 | 880-883 |
| 895-922 | 933-953 | 1004-1006 | 1009-1113 | 1030-1050 | 1075-1081 |
| 1085-1090 | 1097-1102 | 1153-1156 | 1166-1171 | 1201-1212 | 1237-1246 |
| 1264-1280 | 1294-1300 | 1328-1332 | 1335-1346 | 1353-1357 | 1375-1381 |
| 1407-1410 | 1418-1423 | 1426-1431 | 1437-1442 | 1449-1454 | 1459-1464 |
| 1471-1479 | 1494-1500 | | | | |

More preferably, the novel MUC1 nucleic acid can comprise at least one substitution in those MUC1 nucleotide repetitive regions outside of the VNTR regions selected from nucleotides regions and/or combinations thereof of PANVAC MUC1 (SEQ ID NO:1) shown in Table 6.

TABLE 6

| 7-16 | 19-32 | 40-45 | 65-68 | 122-128 | 136-138 |
|---|---|---|---|---|---|
| 194-200 | 207-213 | 222-224 | 240-253 | 296-299 | 705-708 |
| 710-714 | 731-734 | 761-765 | 770-773 | 791-795 | 847-855 |
| 857-864 | 880-883 | 895-898 | 899-914 | 916-922 | 933-937 |
| 940-943 | 945-953 | 1004-1006 | 1009-1113 | 1030-1050 | 1075-1081 |
| 1085-1090 | 1097-1102 | 1153-1156 | 1166-1171 | 1201-1212 | 1237-1240 |
| 1243-1246 | 1264-1280 | 1294-1300 | 1328-1332 | 1335-1337 | 1338-1343 |
| 1344-1346 | 1353-1357 | 1375-1381 | 1407-1410 | 1418-1423 | 1426-1431 |
| 1437-1442 | 1449-1454 | 1459-1464 | 1471-1479 | 1494-1500 | |

It is understood by the present invention that the nucleotide positions listed in Tables 5 and 6 are merely representative of the MUC1 nucleic acid repetitive regions found in the non-VNTR regions of MUC1. Thus, while a repetitive region described herein has a specified nucleotide position in SEQ ID NO:1 (e.g., 240-253), that particular region may correspond to another nucleotide position in another MUC1 nucleic acid.

In additional embodiments, the modifications to the repetitive regions outside of the VNTRs and/or the modifications in the VNTR regions is a silent modification, meaning that the modification does not affect the amino acid sequence of the MUC1 antigen. In at least one aspect, enhancing the stability of the MUC1 transgene by modifying one or more repetitive regions was challenging in that only certain nucleotides and/or repetitive regions could be modified without affecting the amino acid sequence of the MUC1.

In view of the foregoing, in one or more embodiments, the present invention includes one or more MUC1 nucleic acids comprising 1) one or more modifications to the VNTR domain repeats selected from a) shuffling and b) codon optimization; and 2) one or more modifications to repetitive regions outside of the VNTRs.

In another aspect, the MUC1 nucleic acids of the present invention can include one or more modifications configured to enhance the immunogenicity of the MUC1 transgene in a subject. In one non-limiting example, the MUC1 nucleic acids can be modified to include one or more of the agonist epitopes described in WO 2013/103658, which is incorporated by reference herein. In a more specific embodiment, the MUC1 nucleic acids of the present invention include agonist epitopes selected from the group consisting of: YLAPPAHGV [SEQ ID NO: 24], YLDTRPAPV [SEQ ID NO: 25], YLAIVYLIAL [SEQ ID NO: 26], YLIALAVCQV [SEQ ID NO: 27], YLSYTNPAV [SEQ ID NO: 28], and S LFRSPYEK [SEQ ID NO: 29] (underlined portions are substituted amino acids).

In preferred embodiments, the MUC1 nucleic acid comprises a nucleotide sequence at least 95% homologous to SEQ ID NO: 2 (336 MUC), SEQ ID NO: 3 (373 MUC), SEQ ID NO: 4 (399/400 MUC1), or SEQ ID NO: 5 (420 MUC1). In still additional preferred embodiments, the MUC1 nucleic acid comprises a nucleotide sequence at least 96%, 97%, or 98% homologous to SEQ ID NO: 2 (336 MUC), SEQ ID NO:3 (373 MUC), SEQ ID NO: 4 (399/400 MUC1), or SEQ ID NO: 5 (420 MUC1). In a more preferred embodiment, the MUC1 nucleic acid comprises a nucleotide sequence selected from SEQ ID NO: 2 (336 MUC), SEQ ID NO:3 (373 MUC), SEQ ID NO: 4 (399/400 MUC1), or SEQ ID NO: 5 (420 MUC1).

In still other preferred embodiments, the MUC1 nucleic acid comprises a nucleotide sequence at least 95% homologous to SEQ ID NO: 31, SEQ ID NO: 32, SEQ ID NO: 33, or SEQ ID NO: 34. In still additional preferred embodiments, the MUC1 nucleic acid comprises a nucleotide sequence at least 96%, 97%, or 98% homologous to SEQ ID NO: 31, SEQ ID NO: 32, SEQ ID NO: 33, or SEQ ID NO: 34. In a more preferred embodiment, the MUC1 nucleic acid comprises a nucleotide sequence selected from SEQ ID NO: 31, SEQ ID NO: 32, SEQ ID NO: 33, or SEQ ID NO: 34.

Novel CEA Nucleic Acid Sequences

Figure 5:
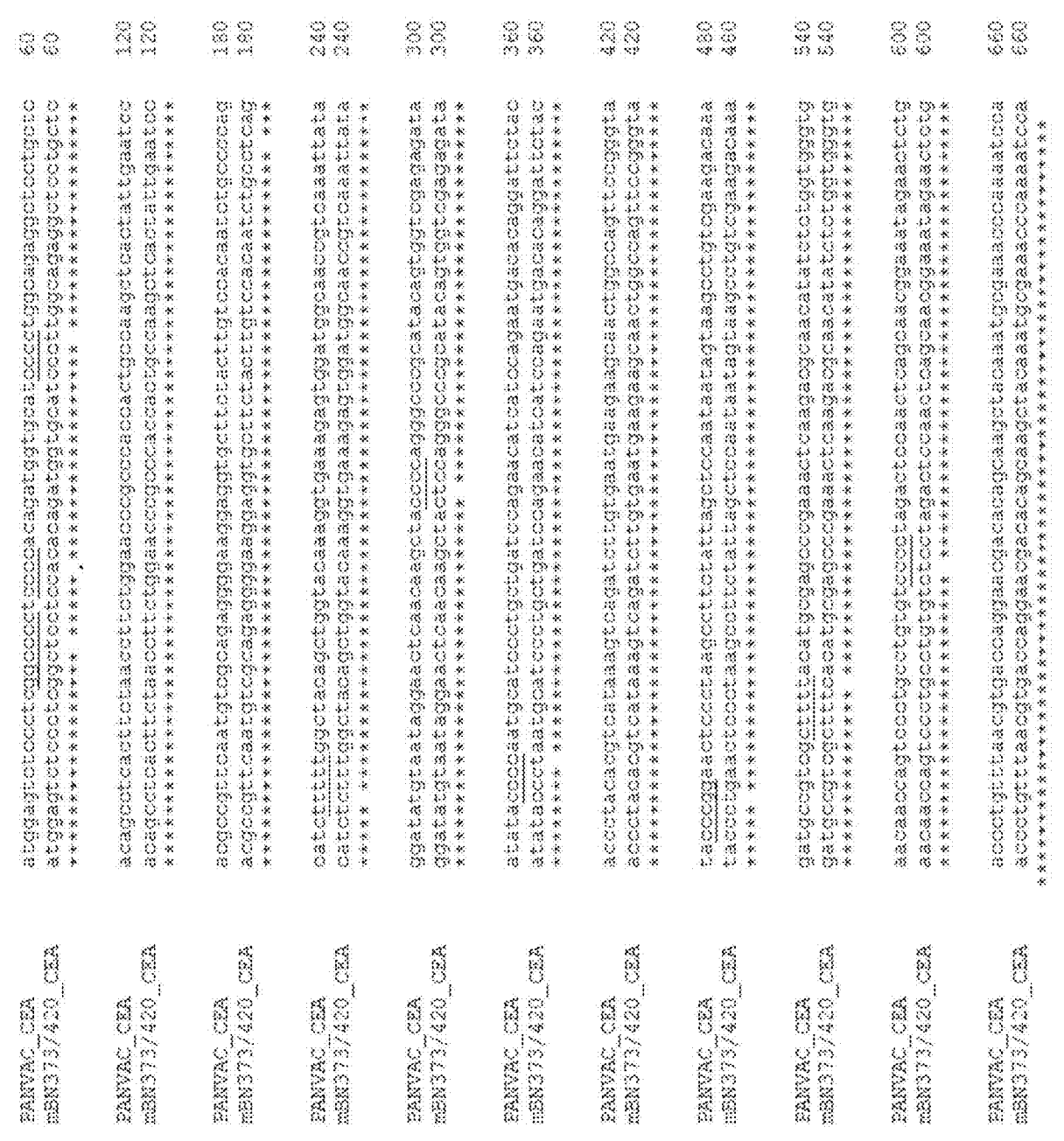
Figure 5:
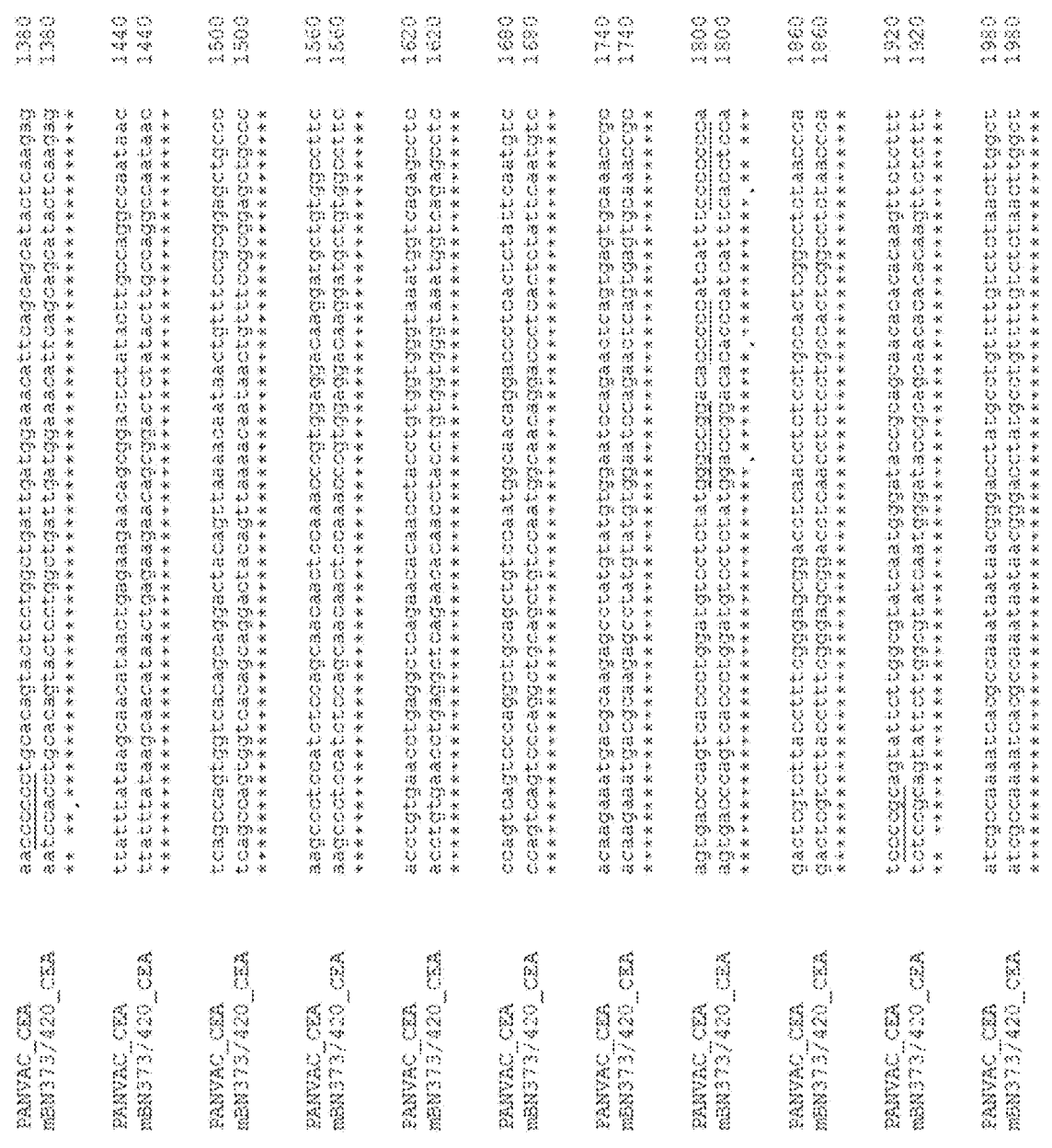

In another aspect of the present invention, it was determined that one or more modifications in the repetitive regions of the CEA nucleic acids improved the stability of the CEA transgene. A representative sample of those regions is illustrated in the pairwise alignment of FIG. 5. Those exemplary repetitive regions are illustrated by the shown substitutions (non*regions of the alignment).

In at least one aspect, the substitution further enhanced the stability of a recombinant poxvirus. This is demonstrated at least in part by the stability data for mBN336 shown in FIGS. 9 and 10. As previously noted, mBN336 includes MUC1, CEA, and TRICOM. While mBN336 includes a modified MUC1 nucleic acid, mBN336 does not include any additional modifications to CEA, and include only intermediate modifications to the TRICOM costimulatory molecules. Thus, while the modifications to MUC1 disclosed herein improved the stability of a recombinant poxvirus, instability starting at Passage 5 remained. Once the modified CEA was included as part of the fowlpox virus in mBN373, stability of the transgene and the fowlpox virus was demonstrated past Passage 5 and into Passage 7. (see, e.g., FIG. 11).

Accordingly, in various embodiments, the present invention includes a nucleic acid encoding a CEA peptide (CEA nucleic acid) comprising at least one nucleotide substitution in at least one repetitive nucleotide region of the CEA nucleic acid, wherein the at least one repetitive nucleotide region is defined as a) three more consecutively repeated G or C nucleotides and/or b) three or more consecutively repeated T nucleotides. In additional embodiments, the repetitive nucleotide regions are further defined as a) three or more consecutively repeated G nucleotides and/or b) three or more consecutively repeated C nucleotides.

In preferred embodiments, the repetitive nucleotide regions of the CEA nucleic acid are defined as (i) four or more consecutively repeated nucleotides, (ii) four or more consecutive G or C nucleotides, and/or (iii) four or more consecutive T nucleotides. In additional preferred embodiments, the repetitive nucleotide region is further defined as (i) four or more consecutive G nucleotides, (ii) four or more consecutive C nucleotides, and/or (iii) four or more consecutive T nucleotides.

In one or more embodiments, the CEA nucleic acid includes at least one substitution to at least 2, 3, 4, 5, or 10 of the repetitive nucleotide regions of the second nucleic acid. In a preferred embodiment, the CEA nucleic acid comprises at least one nucleotide substitution in at least 10, at least 12, at least 15, and/or at least 19 repetitive nucleotide regions. In a more preferred embodiment, the CEA nucleic acid comprises at least one nucleotide substitution in 19 regions of the second nucleic acid.

In more preferred embodiments, the CEA nucleic acid comprises SEQ ID NO: 14 (mBN373/420 CEA).

Novel TRICOM Nucleic Acid Sequences

Figure 6:
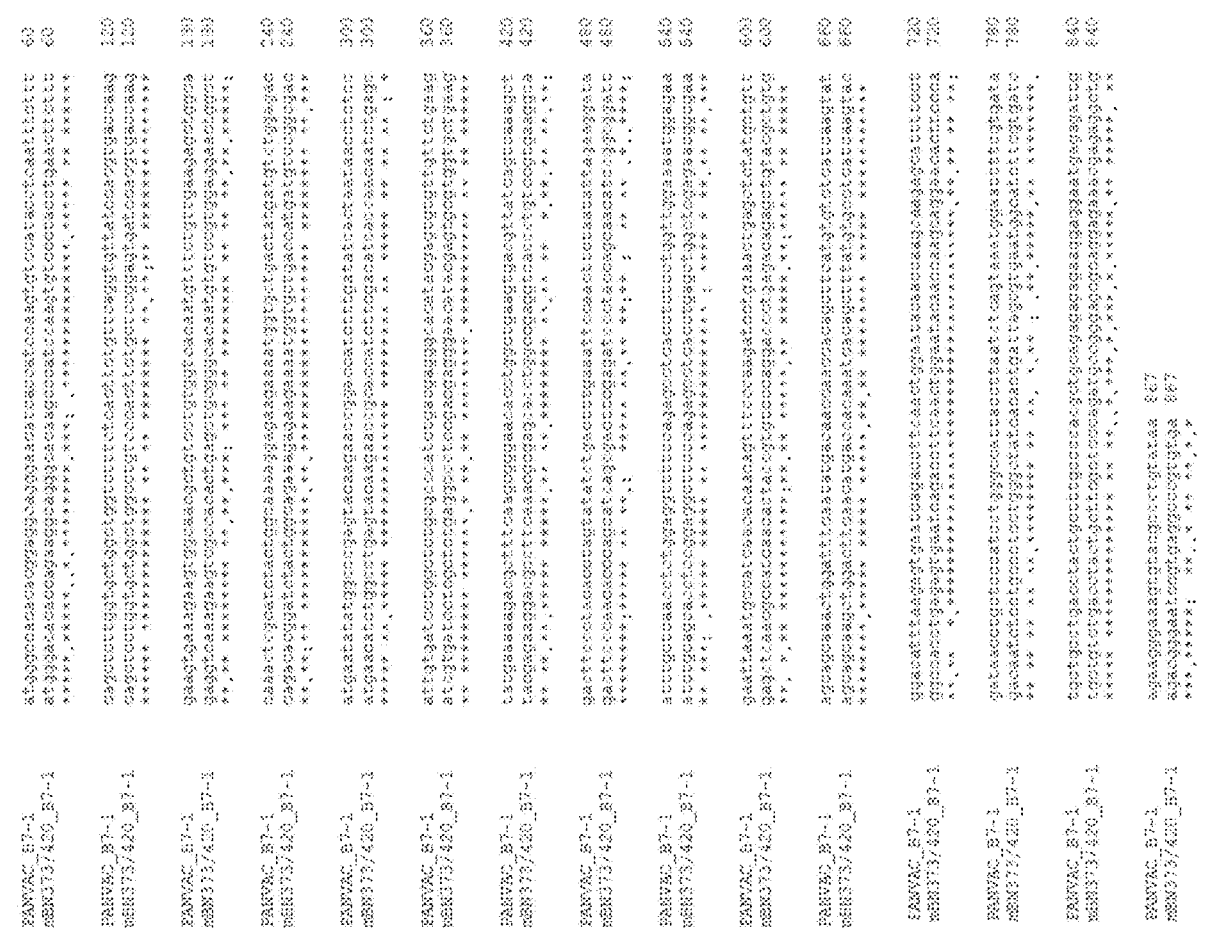
Figure 8:
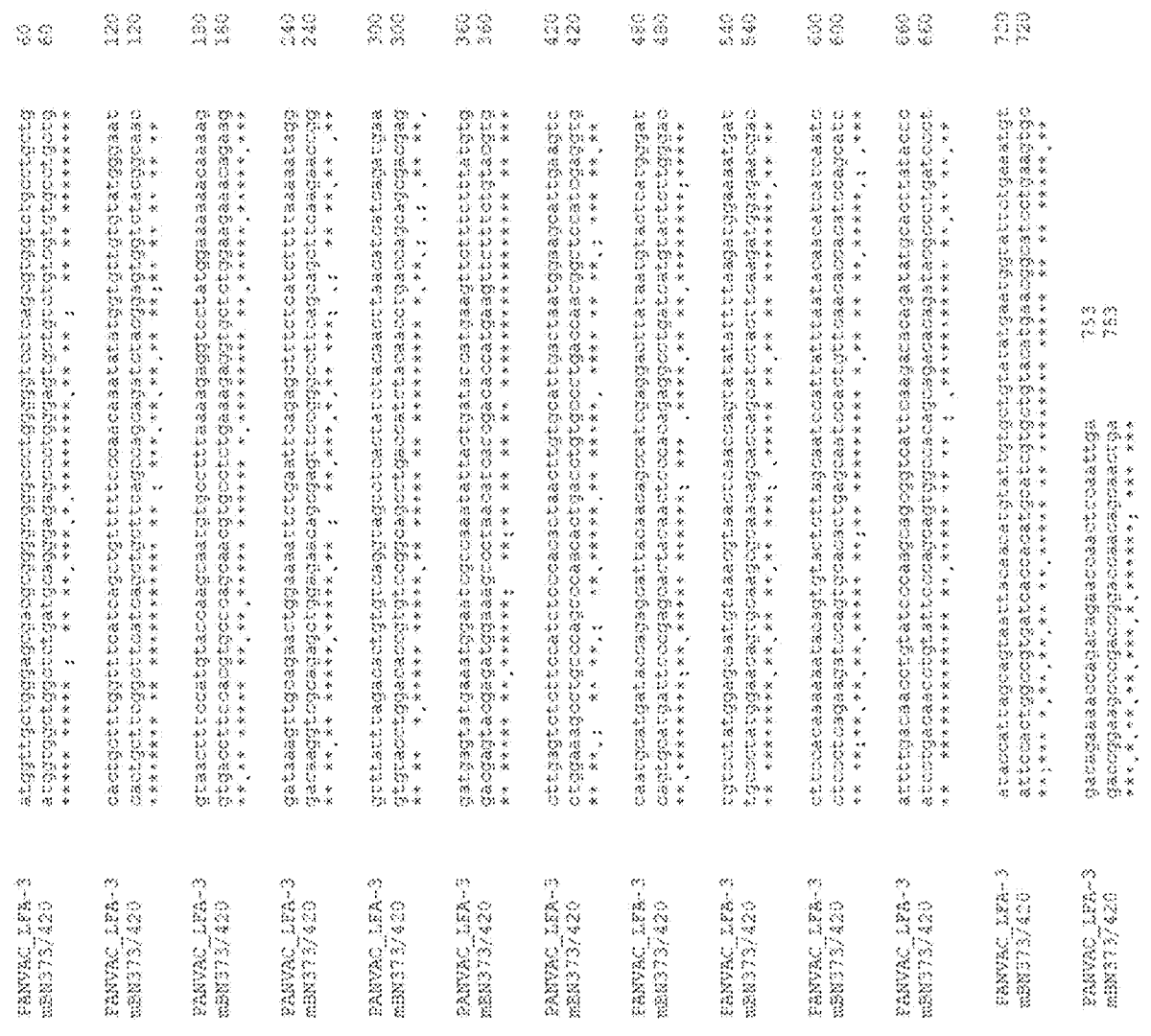

In another aspect of the present invention, one or more modifications were made to one or more nucleic acids encoding the TRICOM costimulatory molecules. In a more specific aspect, over the course of the development of the present invention, it was determined that one or more modifications in the repetitive regions of the TRICOM nucleic acids improved the stability of the TRICOM transgenes. A representative sample of those regions is illustrated in the pairwise alignment of FIGS. 6-8. Those exemplary repetitive regions are illustrated by the shown substitutions (non*regions of the alignment).

In at least one aspect, the one or more substitutions further enhanced the stability of a recombinant poxvirus. This is demonstrated at least in part by the stability data for mBN336 shown in FIGS. 9 and 10. As previously noted, mBN336 includes a modified MUC1. mBN336, however, does not include any additional modifications to CEA, and includes only intermediate modifications to the TRICOM costimulatory molecules. Thus, while the modifications to MUC1 disclosed herein improved the stability of mBN336, instability past Passage 5 remained. Once the modified transgenes were included as part of the fowlpox virus, stability of the transgene and poxvirus was demonstrated past Passage 5 and into Passage 7 (see, e.g., FIG. 11).

In one embodiment, the novel TRICOM costimulatory molecules comprise a nucleotide sequence at least 80% homologous to SEQ ID NO: 15 or 17 (for B7-1), a nucleotide sequence at least 80% homologous to SEQ ID NO: 18 or 20 (for ICAM-1), and a nucleotide sequence at least 80% homologous to SEQ ID NO: 21 or 23 (for LFA-3). In still additional preferred embodiments, the TRICOM nucleic acids comprises a nucleotide sequence at least 85%, 90%, or 95% homologous to SEQ ID NO:15 or 17 (for B7-1), SEQ ID NO: 18 or 20 (for ICAM-1), and/or SEQ ID NO: 21 or 23 (for LFA-3). In still more preferred embodiments, the TRICOM nucleic acids comprises a nucleotide sequence at least 85%, 90%, or 95% homologous to SEQ ID NO:17 (for B7-1), SEQ ID NO: 20 (for ICAM-1), and/or SEQ ID NO: 23 (for LFA-3).

In another embodiment, the TRICOM costimulatory molecules comprise SEQ ID NO: 15 or 17 (for B7-1), SEQ ID NO: 18 or 20 (for ICAM-1), and/or SEQ ID NO: 21 or 23 (for LFA-3).

In yet another embodiment, the TRICOM costimulatory molecules comprise SEQ ID NO: 17 (for B7-1), SEQ ID NO: 20 (for ICAM-1), and/or SEQ ID NO: 23 (for LFA-3).

In one preferred embodiment, the novel TRICOM costimulatory molecules comprise a nucleotide sequence at least 80% homologous to SEQ ID NO: 15 (for B7-1), a nucleotide sequence at least 80% homologous to SEQ ID NO: 18 (for ICAM-1), and a nucleotide sequence at least 80% homologous to SEQ ID NO: 21 (for LFA-3). In still additional preferred embodiments, the TRICOM nucleic acids comprises a nucleotide sequence at least 85%, 90%, or 95% homologous to SEQ ID NO:15 (for B7-1), SEQ ID NO: 18 (for ICAM-1), and/or SEQ ID NO: 21 (for LFA-3).

In another preferred embodiment, the novel TRICOM costimulatory molecules comprise a nucleotide sequence at least 80%, 90%, or 95% homologous to SEQ ID NO: 17 (for B7-1), a nucleotide sequence at least 80%, 90%, or 95% homologous to SEQ ID NO: 20 (for ICAM-1), and a nucleotide sequence at least 80%, 90%, or 95% homologous to SEQ ID NO: 23 (for LFA-3).

In another embodiment, the TRICOM costimulatory molecules comprise SEQ ID NO: 15 (for B7-1), SEQ ID NO: 18 (for ICAM-1), and/or SEQ ID NO: 21 (for LFA-3).

In another embodiment, the TRICOM costimulatory molecules comprise SEQ ID NO: 17 (for B7-1), SEQ ID NO: 20 (for ICAM-1), and/or SEQ ID NO: 23 (for LFA-3).

It is contemplated that the present disclosure embodies those nucleic acid sequences that are complementary to the novel nucleic acid sequences provided herein.

Recombinant Poxviruses

In one or more embodiments, the invention includes a recombinant poxvirus comprising one or more of the MUC1 nucleic acids described herein. In more preferred embodiments, the recombinant poxvirus comprises a MUC1 nucleic acid sequence and a CEA nucleic acid sequence described herein.

In preferred embodiments, the MUC1 nucleic acid comprises a nucleotide sequence at least 95% homologous to SEQ ID NO:2, SEQ ID NO: 3 (373 MUC), SEQ ID NO: 5 (420 MUC1), or SEQ ID NO: 4 (399/400 MUC1), and a CEA nucleic acid sequence comprising SEQ ID NO: 13 or 14.

In still additional embodiments, the recombinant poxviruses of the present disclosure include one or more costimulatory molecules, such as but not limited to, those described herein. In one preferred embodiment, the costimulatory molecules include TRICOM (B7-1, ICAM-1, and LFA-3). In a more preferred embodiment, the B7-1 costimulatory molecules are selected from a nucleic acid sequence comprising SEQ ID NO:15, SEQ ID NO:16, and SEQ ID NO:17. In a more preferred embodiment, the ICAM-1 costimulatory molecule is selected from a nucleic acid sequence comprising SEQ ID NO:18, SEQ ID NO:19, and SEQ ID NO:20. In a more preferred embodiment, the LFA-3 costimulatory molecule is selected from a nucleic acid sequence comprising SEQ ID NO:21, SEQ ID NO:22, and SEQ ID NO:23. In a more preferred embodiment, the B7-1, ICAM-1, and LFA-3 are selected from a nucleic acid sequence comprising SEQ ID NO:15, SEQ ID NO:18, and SEQ ID NO: 21, respectively. In another more preferred embodiment, the B7-1, ICAM-1, and LFA-3 are selected from a nucleic acid sequence comprising SEQ ID NO: 17, SEQ ID NO: 20, and SEQ ID NO: 23, respectively.

In the various embodiments of the present disclosure, the recombinant poxvirus is preferably an orthopoxvirus such as, but not limited to, a vaccinia virus, a Modified Vaccinia Ankara (MVA) virus, MVA-BN, or derivatives of MVA-BN.

Examples of vaccinia virus strains are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, Elstree, Ikeda and WR. A preferred vaccinia virus (VV) strain is the Wyeth (DRYVAX) strain (U.S. Pat. No. 7,410,644).

Another preferred VV strain is a modified vaccinia virus Ankara (MVA) (Sutter, G. et al. (1994), *Vaccine* 12: 1032-40). Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, with the deposition number ECACC 94012707 on Jan. 27, 1994; and MVA 575, deposited under ECACC 00120707 on Dec. 7, 2000; MVA-BN, deposited on Aug. 30, 2000 at the European Collection of Cell Cultures (ECACC) under number V00083008; and derivatives of MVA-BN, are additional exemplary strains.

"Derivatives" of MVA-BN refer to viruses exhibiting essentially the same replication characteristics as MVA-BN, as described herein, but exhibiting differences in one or more parts of their genomes. MVA-BN, as well as derivatives thereof, are replication incompetent, meaning a failure to reproductively replicate in vivo and in vitro. More specifically in vitro, MVA-BN or derivatives thereof have been described as being capable of reproductive replication in chicken embryo fibroblasts (CEF), but not capable of reproductive replication in the human keratinocyte cell line HaCat (Boukamp et al (1988), *J. Cell Biol.* 106: 761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, MVA-BN or derivatives thereof have a virus amplification ratio at least two fold less, more preferably three-fold less than MVA-575 in Hela cells and HaCaT cell lines. Tests and assay for these properties of MVA-BN and derivatives thereof are described in WO 02/42480 (U.S. Patent Publication No. 2003/0206926, issued as U.S. Pat. No. 6,913,752) and WO 03/048184 (U.S. Patent Publication No. 2006/0159699, issued as U.S. Pat. No. 7,759,116).

The term "not capable of reproductive replication" or "no capability of reproductive replication" in human cell lines in vitro as described in the previous paragraphs is, for example, described in WO 02/42480, which also teaches how to obtain MVA having the desired properties as mentioned above. The term applies to a virus that has a virus amplification ratio in vitro at 4 days after infection of less than 1 using the assays described in WO 02/42480 or in U.S. Pat. No. 6,761,893.

The term "failure to reproductively replicate" refers to a virus that has a virus amplification ratio in human cell lines in vitro as described in the previous paragraphs at 4 days after infection of less than 1. Assays described in WO 02/42480 or in U.S. Pat. No. 6,761,893 are applicable for the determination of the virus amplification ratio.

The amplification or replication of a virus in human cell lines in vitro as described in the previous paragraphs is normally expressed as the ratio of virus produced from an infected cell (output) to the amount originally used to infect the cell in the first place (input) referred to as the "amplification ratio." An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

In another embodiment, the recombinant poxvirus including the MUC1 and/or other nucleic acids disclosed herein is an avipoxvirus such as, but not limited to, a fowlpox virus.

The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

Examples of a fowlpox virus are strains FP-1, FP-5, TROVAC (U.S. Pat. No. 5,766,598), PDXVAC-TC (U.S. Pat. No. 7,410,644), and TBC-FPV (Therion Biologics-FPV). FP-1 is a Duvette strain modified to be used as a vaccine in one-day-old chickens. The strain is a commercial fowlpox virus vaccine strain designated O DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., USA, United States Veterinary License No. 165, serial No. 30321.

In certain preferred embodiments, there is a recombinant orthopoxvirus, such as Vaccinia, MVA, MVA-BN, or derivatives of MVA-BN comprising a MUC1 nucleic acid sequence selected from SEQ ID NO: 5 (420 MUC1), SEQ ID NO: 4 (399/400 MUC1), SEQ ID NO:3 (373 MUC1), OR SEQ ID NO:2 (336 MUC1). In certain more preferred embodiments, the recombinant orthopoxvirus is an MVA virus comprising a MUC1 nucleic acid sequence selected from SEQ ID NO: 2 (420 MUC1), a CEA nucleic acid selected from SEQ ID NO: 13 or 14, and TRICOM. In a most preferred embodiment, there is a recombinant MVA comprising a MUC1 nucleic acid sequence comprising SEQ ID NO: 2 (336 MUC1), a CEA nucleic acid comprising SEQ ID NO: 13, and TRICOM. In another most preferred the TRICOM includes one or more nucleic acids comprising SEQ ID NO: 17, (B7-1), SEQ I NO: 20 (ICAM-1), and SEQ ID NO: 23 (LFA-3).

In certain other preferred embodiments, there is a recombinant avipoxvirus, such as a fowlpox virus, comprising a MUC1 nucleic acid sequence comprising SEQ ID NO:3 (373 MUC1). In certain more preferred embodiments, the recombinant avipoxvirus is a fowlpox virus comprising a MUC1 nucleic acid comprising SEQ ID NO: 3 (373), a CEA nucleic acid selected from SEQ ID NO: 13 or 14, and TRICOM. In a most preferred embodiment, there is a recombinant fowlpox virus comprising a MUC1 nucleic acid sequence comprising SEQ ID NO: 3 (373 MUC1), a CEA nucleic acid comprising SEQ ID NO: 14, and TRICOM. In another most preferred the TRICOM includes one or more nucleic acids comprising SEQ ID NO: 15 (B7-1), SEQ I NO: 18 (ICAM-1), and SEQ ID NO: 21(LFA-3).

Expression Cassettes/Control Sequences

In various aspects, the one or more nucleic acids described herein are embodied in in one or more expression cassettes in which the one or more nucleic acids are operatively linked to expression control sequences. "Operably linked" means that the components described are in relationship permitting them to function in their intended manner, e.g., a promoter to transcribe the nucleic acid to be expressed. An expression control sequence operatively linked to a coding sequence is joined such that expression of the coding sequence is achieved under conditions compatible with the expression control sequences. The expression control sequences include, but are not limited to, appropriate promoters, enhancers, transcription terminators, a start codon at the beginning a protein-encoding open reading frame, splicing signals for introns, and in-frame stop codons. Suitable promoters include, but are not limited to, the SV40 early promoter, an RSV promoter, the retrovirus LTR, the adenovirus major late promoter, the human CMV immediate early I promoter, and various poxvirus promoters including, but not limited to the following vaccinia virus or MVA-derived and FPV-derived promoters: the 30K promoter, the 13 promoter, the PrS promoter, the PrS5E promoter, the Pr7.5K, the Pr13.5 long promoter, the 40K promoter, the MVA-40K promoter, the FPV 40K promoter, 30 k promoter, the PrSynIIm promoter, and the PrLE1 promoter. Additional promoters are further described in WO 2010/060632, WO 2010/102822, WO 2013/189611 and WO 2014/063832 which are incorporated fully by reference herein.

Additional expression control sequences include, but are not limited to, leader sequences, termination codons, polyadenylation signals and any other sequences necessary for the appropriate transcription and subsequent translation of the nucleic acid sequence encoding the desired recombinant protein (e.g., MUC1, CEA, and/or TRICOM) in the desired host system. The poxvirus vector may also contain additional elements necessary for the transfer and subsequent replication of the expression vector containing the nucleic acid sequence in the desired host system. It will further be understood by one skilled in the art that such vectors are easily constructed using conventional methods (Ausubel et al., (1987) in "Current Protocols in Molecular Biology," John Wiley and Sons, New York, N.Y.) and are commercially available. In certain embodiments, the recombinant orthopoxvirus and/or avipoxvirus of the present disclosure comprises one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6 (Suppl 1):561-6; Cao et al., 1998, *Stem Cells* 16 (Suppl 1):251-60; Kuiper et al., 2000, *Adv. Exp. Med. Biol.* 465:381-90). These molecules can be administered systemically (or locally) to the host. In several examples, IL-2, RANTES, GM-CSF, TNF-α, IFN-γ, G-CSF, LFA-3, CD72, B7-1, B7-2, OX-40L, 41 BBL and ICAM-1 are administered.

Generation of Recombinant Poxviruses Comprising Transgenes

The recombinant poxviruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR, and PCR amplification techniques are described in *Molecular Cloning, A Laboratory Manual* (2nd Ed.) (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of MVA are described in *Molecular Virology: A Practical Approach* (A. J. Davison & R. M. Elliott (Eds.), The Practical Approach Series, IRL Press at Oxford University Press, Oxford, UK (1993) (see, e.g., Chapter 9: Expression of genes by Vaccinia virus vectors)) and *Current Protocols in Molecular Biology* (John Wiley & Son, Inc. (1998) (see, e.g., Chapter 16, Section IV: Expression of proteins in mammalian cells using vaccinia viral vector)).

For the generation of the various recombinant poxviruses disclosed herein, different methods may be applicable. The DNA sequence to be inserted into the virus can be placed into an *E. coli* plasmid construct into which DNA homologous to a section of DNA of the poxvirus has been inserted.

Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxviral DNA containing a non-essential locus. The resulting plasmid construct can be amplified by propagation within E. coli bacteria and isolated. The isolated plasmid containing the DNA gene sequence to be inserted can be transfected into a cell culture, e.g., of chicken embryo fibroblasts (CEFs), at the same time the culture is infected with poxvirus. Recombination between homologous poxviral DNA in the plasmid and the viral genome, respectively, can generate a poxvirus modified by the presence of foreign DNA sequences.

According to a preferred embodiment, a cell of a suitable cell culture such as, e.g., CEF cells, can be infected with a poxvirus. The infected cell can be, subsequently, transfected with a first plasmid comprising a foreign or heterologous gene or genes, such as one or more of the MUC1, CEA, and/or TRICOM nucleic acids provided in the present disclosure; preferably under the transcriptional control of a poxvirus expression control element. As explained above, the plasmid also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, another cell can be infected with the recombinant poxvirus obtained as described above and transfected with a second vector comprising a second foreign or heterologous gene or genes. If this gene or genes is/are introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in E. coli or another bacterial species between a poxvirus genome cloned as a bacterial artificial chromosome (BAC) and a linear foreign sequence flanked with DNA sequences homologous to sequences flanking the desired site of integration in the vaccinia virus genome.

The one or more nucleic acids of the present disclosure may be inserted into any suitable part of the poxvirus. In a preferred aspect, the poxvirus used for the present invention include MVA and/or fowlpox virus. Suitable parts of the MVA and fowlpox virus are non-essential parts of the MVA and the fowlpox genomes.

For MVA, non-essential parts of the MVA genome may be intergenic regions or the known deletion sites 1-6 of the MVA genome. Alternatively or additionally, non-essential parts of the recombinant MVA can be a coding region of the MVA genome which is non-essential for viral growth. However, the insertion sites are not restricted to these preferred insertion sites in the MVA genome, since it is within the scope of the present invention that the nucleic acids of the present invention (e.g., MUC1, CEA, and TRICOM) and any accompanying promoters as described herein may be inserted anywhere in the viral genome as long as it is possible to obtain recombinants that can be amplified and propagated in at least one cell culture system, such as Chicken Embryo Fibroblasts (CEF cells).

Preferably, the nucleic acids of the present invention may be inserted into one or more intergenic regions (IGR) of the MVA and/or fowlpox virus. The term "intergenic region" refers preferably to those parts of the viral genome located between two adjacent open reading frames (ORF) of the MVA and/or fowlpox virus genome, preferably between two essential ORFs of the MVA and/or fowlpox virus genome. For MVA, in certain embodiments, the IGR is selected from IGR 07/08, IGR 44/45, IGR 64/65, IGR 88/89, IGR 136/137, and IGR 148/149. For fowlpox virus, the IGR is selected from the BamH1 ("J") site.

For MVA virus, the nucleotide sequences may, additionally or alternatively, be inserted into one or more of the known deletion sites, i.e., deletion sites I, II, III, IV, V, or VI of the MVA genome. The term "known deletion site" refers to those parts of the MVA genome that were deleted through continuous passaging on CEF cells characterized at 20 passage 516 with respect to the genome of the parental virus from which the MVA is derived from, in particular the parental chorioallantois vaccinia virus Ankara (CVA) e.g., as described in Meisinger-Henschel et al. (2007), *Journal of General Virology* 88: 3249-3259.

Vaccines

In certain embodiments, the recombinant poxviruses of the present disclosure can be formulated as part of a vaccine. For the preparation of vaccines, the poxvirus can be converted into a physiologically acceptable form. In certain embodiments, such preparation is based on experience in the preparation of poxvirus vaccines used for vaccination against smallpox, as described, for example, in Stickl, H. et al., *Dtsch. med. Wschr.* 99, 2386-2392 (1974).

An exemplary preparation follows. Purified virus is stored at −80° C. with a titer of $5 \times 10^8$ TCID$_{50}$/ml formulated in 10 mM Tris, 140 mM NaCl, pH 7.4. For the preparation of vaccine shots, e.g., $10^2$-$10^8$ particles of the virus can be lyophilized in phosphate-buffered saline (PBS) in the presence of 2% peptone and 1% human albumin in an ampoule, preferably a glass ampoule. Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C.

In various embodiments involving vaccination or therapy, the lyophilisate is dissolved in 0.1 to 0.5 ml of an aqueous solution, preferably physiological saline or Tris buffer, and administered either systemically or locally, i.e., by parenteral, subcutaneous, intravenous, intramuscular, intranasal, intradermal, or any other path of administration known to a skilled practitioner. Optimization of the mode of administration, dose, and number of administrations is within the skill and knowledge of one skilled in the art.

In certain embodiments, attenuated vaccinia virus strains are useful to induce immune responses in immune-compromised animals, e.g., monkeys (CD4<400/µl of blood) infected with SIV, or immune-compromised humans. The term "immune-compromised" describes the status of the immune system of an individual that exhibits only incomplete immune responses or has a reduced efficiency in the defense against infectious agents.

Kits, Compositions, and Methods of Use

In one various embodiments, the invention encompasses kits and/or compositions comprising a recombinant poxvirus that includes the nucleic acids described herein. Preferably, the composition is a pharmaceutical or immunogenic composition.

In one embodiment, there is a kit and/or composition comprising a combination of two or more recombinant poxviruses each recombinant poxvirus including the MUC1, CEA, and/or TRICOM nucleic acids of the present disclosure. The combination comprises a) an orthopoxvirus, such as vaccinia, MVA, MVA-BN, or derivatives of MVA-BN including the MUC1, CEA, and/or TRICOM nucleic acids of the present disclosure and b) an avipoxvirus, such as fowlpox, including the MUC1, CEA, and/or TRICOM nucleic acids of the present disclosure. It is contemplated that the orthopoxvirus and fowlpox virus combination can be administered as a homologous or heterologous prime-boost regimen.

In another embodiment, the kit and/or composition including the combination of two or more recombinant poxviruses comprises a) an MVA virus include the MUC1, CEA, and/or TRICOM nucleic acids of the present disclosure and b) an avipoxvirus, such as fowlpox, including the MUC1, CEA, and/or TRICOM nucleic acids of the present disclosure. It is contemplated that the MVA virus and fowlpox virus combination can be administered as a homologous or heterologous prime-boost regimen.

In additional embodiment, each of the one or more recombinant poxviruses further comprise one or more of the costimulatory molecules of the present disclosure. In a preferred embodiment, one or more costimulatory molecules are one or more of the TRICOM molecules of the present disclosure.

It is contemplated that the kit and/or composition can comprise one or multiple containers or vials of the recombinant poxviruses of the present disclosure, together with instructions for the administration of the recombinant poxviruses.

The kits and/or compositions provided herein may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of compositions (e.g., pharmaceutical and/or immunogenic compositions), the recombinant poxviruses provided herein can be converted into a physiologically acceptable form. This can be done based on experience in the preparation of poxvirus vaccines used for vaccination against smallpox as described by H. Stickl et al., Dtsch. med. Wschr. 99:2386-2392 (1974).

For example, purified viruses can be stored at −80° C. with a titer of $5\times10^8$ $TCID_{50}$/ml formulated in about 10 mM Tris, 140 mM NaCl pH 7.4. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. A typical virus containing formulation suitable for freeze-drying comprises 10 mM Tris-buffer, 140 mM NaCl, 18.9 g/l Dextran (MW 36,000-40,000), 45 g/l Sucrose, 0.108 g/l L-glutamic acid mono potassium salt monohydrate pH 7.4. The glass ampoule is then sealed and can be stored between 4° C. and room temperature for several months. However, as long as no need exists, the ampoule is stored preferably at temperatures at or below −20° C.

For vaccination or therapy, the lyophilisate can be dissolved in an aqueous solution (e.g., 0.1 to 0.5 ml), preferably water for injection, physiological saline or Tris buffer, and administered either systemically or locally, i.e., parenteral, subcutaneous, intravenous, intramuscular, intranasal, or any other path of administration known to the skilled practitioner. The mode of administration, the dose and the number of administrations can be optimized by those skilled in the art in a known manner.

In various other embodiments, there are one or more methods related to generating and/or improving the stability of the recombinant poxvirus and/or the transgenes therein throughout successive passaging of the recombinant poxvirus. In a more specific embodiment, the recombinant poxvirus is stable through at least 3 or 4 passages.

Having a stable recombinant poxvirus throughout multiple passages is particularly important for many reasons, some of which include large scale production of the recombinant virus and its use as a medicament, as well as governmental policies for vaccine stability through multiple passages. For recombinant poxviruses of the present invention, generating a stable recombinant poxvirus through at least 3 or 4 passages is important as PANVAC-V and PANVAC-F began to demonstrate instability and/or loss of transgene viability around passage 1 (See, e.g., Tables 1 and 2; and FIGS. 1A and 1B).

In one embodiment there is a method for generating a poxvirus having a MUC1 transgene that is stable through successive passaging of the recombinant poxvirus, the method comprising: a) providing any one of the nucleic acids or expression cassettes of the present disclosure; and b) inserting the nucleic acid or the expression cassette into a recombinant poxvirus, wherein the recombinant poxvirus is stable through successive passaging.

Exemplary Methods According to the Present Disclosure 1. In another embodiment, there is a method for generating a recombinant poxvirus that is stable through successive passaging of the recombinant poxvirus, the method comprising:
   a) providing a first nucleic acid encoding a MUC1 peptide having at least two Variable N-Terminal Repeat (VNTR) domains, wherein a) the arrangement of the at least two VNTR domains are shuffled, and b) the at least two VNTR domains are codon optimized, wherein the recombinant poxvirus is stable through successive passaging of the recombinant poxvirus.

2. In another embodiment, there is a method for generating a stable recombinant poxvirus that is stable through successive passaging of the recombinant poxvirus, the method comprising: providing a first nucleic acid encoding a MUC1 protein, the MUC1 protein comprising at least two VNTR domains; shuffling or rearranging the order of the at least two VNTR domain repeats; optimizing the codons of the at least two VNTR domain repeats; inserting the first nucleic acid sequence into the poxvirus to generate a recombinant poxvirus that is stable successive passaging of the recombinant poxvirus.

3. The methods of any one of 1 and 2 wherein the first nucleic acid is at least 95% homologous to SEQ ID NO:2, 95% homologous to SEQ ID NO: 4, 95% homologous to SEQ ID NO: 3, or 95% homologous to SEQ ID NO: 5.

4. The method of any one of 1 to 3, wherein the nucleic acid is at least 95% homologous to SEQ ID NO: 2.

5. The method of any one of 1 to 4, wherein the nucleic acid is at least 95% homologous to SEQ ID NO: 3.

6. The method of any one of 1 to 5, wherein the nucleic acid comprises SEQ ID NO: 2.

7. The method of any one of 1 to 6, wherein the nucleic acid comprises SEQ ID NO: 5.

8. The method of any one of 1 to 7, wherein the method further comprises substituting at least one nucleotide in a repetitive nucleotide region of a second nucleic acid encoding a CEA peptide, wherein the repetitive nucleotide region is defined as: (i) three or more consecutively repeated nucleotides, (ii) three or more consecutive G or C nucleotides, and/or (iii) three or more consecutive T or C nucleotides; and inserting the second nucleic acid in the recombinant poxvirus.

9. The method of 8, wherein the repetitive region of the second nucleic acid is further defined as (i) three or more consecutive G nucleotides, (ii) three or more consecutive C nucleotides, and/or (iii) three or more consecutive T nucleotides.

10. The method of any one of 8 and 9, wherein the repetitive nucleotide region of the second nucleic acid is further defined as (i) four or more consecutively repeated nucleotides, (ii) four or more consecutive G or C nucleotides, and/or (iii) four or more consecutive T or C nucleotides.

11. In one aspect of the methods of 1-10, the CEA nucleotide region is further defined as (i) four or more consecutively repeated nucleotides, (ii) four or more consecutive G or C nucleotides, and/or (iii) four or more consecutive T or C nucleotides.

12. In one aspect of the methods of 1-11, the CEA repetitive region is further defined as (i) four or more consecutive G nucleotides, (ii) four or more consecutive C nucleotides, and/or (iii) four or more consecutive T nucleotides.

13. In one aspect of the methods of 1-12, the substitution is to at least 2, 3, 4, 5, or 10 repetitive nucleotide regions of the CEA nucleic acid.

14. In one aspect of the methods of 1-13, the CEA nucleic acid comprises SEQ ID NO: 14.

15. In one aspect of the methods of 1-14, the method further comprises substituting at least one nucleotide in a repetitive nucleotide region of a nucleic acid encoding a costimulatory molecule selected from B7-1, ICAM-1, and/or LFA-3, CEA, wherein the repetitive nucleotide region is defined as: (i) three or more consecutively repeated nucleotides, (ii) three or more consecutive G or C nucleotides, and/or (iii) three or more consecutive T or C nucleotides; and inserting the nucleic acid encoding a costimulatory molecule in the recombinant poxvirus.

16. In one aspect of the methods of 1-15, the costimulatory molecule repetitive region is further defined as (i) three or more consecutive G nucleotides, (ii) three or more consecutive C nucleotides, and/or (iii) three or more consecutive T nucleotides.

17. In one aspect of the methods of 1-16, the costimulatory molecule repetitive nucleotide region is further defined as (i) four or more consecutively repeated nucleotides, (ii) four or more consecutive G or C nucleotides, and/or (iii) four or more consecutive T or C nucleotides.

18. In one aspect of the methods of 1-17, the costimulatory molecule repetitive region is further defined as (i) four or more consecutive G nucleotides, (ii) four or more consecutive C nucleotides, and/or (iii) four or more consecutive T nucleotides.

19. In one aspect of the methods of 1-18, the substitution is to at least 2, 3, 4, 5, or 10 repetitive nucleotide regions of the costimulatory molecule nucleic acid.

20. In one aspect of the methods of 1-19, the nucleic acid encoding the costimulatory molecule is selected from B7-1 (SEQ ID NOs: 15-17); ICAM-1 (SEQ ID NOs: 18-20) and LFA-3 (SEQ ID NOs: 21-23).

21. In one aspect of the methods of 1-20, the nucleic acid encoding the costimulatory molecule is at least 80%, 85%, 90%, or 95% homologous to at least one of B7-1 (SEQ ID NO: 15; ICAM-1 (SEQ ID NO: 18) and LFA-3 (SEQ ID NO: 21).

22. In one aspect of the methods of 1-21, the nucleic acid encoding the costimulatory molecule is at least 80%, 85%, 90%, or 95% homologous to at least one of B7-1 (SEQ ID NO: 17; ICAM-1 (SEQ ID NO: 20) and LFA-3 (SEQ ID NO: 23).

23. In one aspect of the methods of 1-22, the nucleic acid encoding the costimulatory molecule comprises at least one of B7-1 (SEQ ID NO: 17; ICAM-1 (SEQ ID NO: 20) and LFA-3 (SEQ ID NO: 23).

24. In one aspect of the methods of 1-23, the nucleic acid encoding the costimulatory molecule is comprises: B7-1 (SEQ ID NO: 15; ICAM-1 (SEQ ID NO: 18) and LFA-3 (SEQ ID NO: 21).

25. In one aspect of the methods of 1-24, the first nucleic acid encoding the MUC1 is selected from SEQ ID NOs: 31, 32, 33, and 34.

26. As provided for by the present disclosure, the recombinant poxvirus of the methods of 1-26, can be selected from an orthopoxvirus or an avipoxvirus. In preferred embodiments, the orthopoxvirus is selected from a vaccinia virus, MVA, MVA-BN, and derivatives of MVA-BN. In a more preferred embodiment, the orthopoxvirus is either MVA, MVA-BN, or a derivative or MVA-BN. In still another more preferred embodiment, the avipoxvirus is a fowlpox virus.

In other embodiments, there is a use of a) a nucleic acid, b) an expression cassettes, c) a composition, d) a host cell, or e) a vector according to the present disclosure in a method for generating a recombinant poxvirus that is stable through successive passaging of the poxvirus.

In still other embodiments, there is a use of a) a recombinant poxvirus, b) a nucleic acid, c) an expression cassette, d) a composition, d) a host cell, or e) a vector according to the present disclosure in the preparation of a medicament preferably a vaccine.

In still further embodiments, there is a recombinant poxvirus, b) a nucleic acid, b) an expression cassette, c) a composition, d) a host cell, or e) a vector according to the present disclosure for use as a medicament preferably a vaccine.

In yet additional embodiments, there is a recombinant poxvirus, b) a nucleic acid, b) an expression cassette, c) a composition, d) a host cell, or e) a vector according to the present disclosure for use in a method for introducing a coding sequence into a target cell.

EXAMPLES

The following examples illustrate the invention but, of course should not be construed as in any way limiting the scope of the claims.

Example 1: Construction of Recombinant Poxviruses

Generation of the poxviruses encoding MUC1(e.g., mBN399, mBN400, mBN336, mBN373, and mBN420) was done by insertion of the indicated MUC1 and CEA nucleic acid sequences with their promoters via simultaneous infection and transfection of CEF cultures, followed by allowed homologous recombination between the viral genome and the recombination plasmid pBN146. Insert-carrying virus was isolated, characterized, and virus stocks were prepared.

For construction of mBN398 and mBN400, an MVA recombination plasmid containing homologous sequences which are also present in Vaccinia Virus at the IGR88/89 were used). The MUC1 and CEA nucleotide sequence was inserted between the Vaccinia Virus sequences at IGR 88/89 to allow for recombination into the Vaccinia viral genome. Thus, a plasmid was constructed that contained the MUC1 and CEA nucleotide sequence downstream of a poxvirus promoter. For mBN 398 and mBN400 SEQ ID NO:1 (MUC1) and SEQ ID NO: 13 (CEA) were used. Promoters for MUC1 and CEA in mBN398 were PrS promoter (MUC1) and the 40 k-MVA1 promoter (CEA), respectively. Promoters for MUC1 and CEA in mBN400 were Pr13.5 long (MUC1) and the PrS5E promoter (CEA), respectively. Costimulatory molecules of TRICOM were included as part of mBN398 and mBN400. These sequences included: B7-1, ICAM-1, and LFA-3 and comprise SEQ ID NOs: 16, 19, and 21, respectively.

For construction of mBN336, three recombination plasmids were used for the three transgenes pBN374 (for TRICOM), pBN515 (for CEA SEQ ID NO: 13), pBN525 (for MUC1 SEQ ID NO: 2), insert sequences which are also present in MVA (IGR88/89(MUC1), IGR 44/45 (CEA), IGR 148/149 (TRICOM). The MUC1 and CEA nucleotide sequence was inserted between the MVA virus sequences to allow for recombination into the MVA viral genome. Thus, a plasmid was constructed that contained the MUC1 and CEA nucleotide sequence downstream of a poxvirus promoter. For mBN336, SEQ ID NO: 2 (MUC1) and SEQ ID NO: 13 (CEA) were used. Promoters were PrS promoter (for MUC1) and the 40 k promoter (for CEA). Costimulatory molecules of TRICOM were included as part of mBN336. These sequences included: B7-1, ICAM-1, and LFA-3 and comprise SEQ ID NOs: 17, 20, and 23, respectively. pBN632 contains sequences which are also present in MVA (within IGR 88/89). The MUC1 and CEA nucleotide sequence was inserted between the MVA virus sequences to allow for recombination into the MVA viral genome. Thus, a plasmid was constructed that contained the MUC1 and CEA nucleotide sequence downstream of a poxvirus promoter. For mBN420, SEQ ID NO: 5 (MUC1) and SEQ ID NO: 14 (CEA) were used. Promoters for MUC1 and CEA were Pr13.5 promoter (see US patent publication 2015/0299267) (MUC1) and the 40 k MVA1 promoter (CEA), respectively. Costimulatory molecules of TRICOM were included as part of mBN420 and integrated within IGR 88/89. These sequences included: B7-1, ICAM-1, and LFA-3 and comprise SEQ ID NOs: 15, 18, and 21, respectively.

For construction of mBN373, recombination plasmid pBN563 contains sequences which are also present in fowlpox virus. The MUC1 and CEA nucleotide sequence was inserted between the fowlpox virus sequences in the BamH1 region to allow for recombination into the fowlpox viral genome. Thus, a plasmid was constructed that contained the MUC1 and CEA nucleotide sequence downstream of a poxvirus promoter. For mBN373, SEQ ID NO: 3 (MUC1) and SEQ ID NO: 14 (CEA) were used. Promoters for MUC1 and CEA were 40K FPV-1 PrS promoter (MUC1) and the 40 k-MVA1 promoter (CEA), respectively. Costimulatory molecules of TRICOM were included as part of mBN373. These sequences included: B7-1, ICAM-1, and LFA-3 and comprise SEQ ID NOs: 15, 18, and 21, respectively.

The above recombination plasmids also contained a selection cassette comprising a synthetic vaccinia virus promoter (Ps), a drug resistance gene GPT, an internal ribosomal entry site (IRES), and the enhanced green fluorescent protein (EGFP), and the drug resistance gene guanine-xanthine phosphoribosyltransferase (Ecogpt) in combination with the Monomeric Red Fluorescent Protein. All selection genes (GFP, NPTII, and mRFP1) were encoded by a single bicistronic transcript.

CEF cultures were inoculated with Vaccinia virus for mBN399/400, MVA-BN for mBN336, mBN420, or FPV for mBN373 and each CEF culture was also transfected with plasmid DNA. In turn, samples from these cell cultures were inoculated into CEF cultures in medium containing selection drugs, and EGFP-expressing viral clones were isolated by plaque purification. Virus stocks which grew in the presence of the selection drugs and expressed EGFP were designated one of the following: mBN399, mBN400 (Vaccinia viruses), mBN336, mBN420 (MVA virus), and mBN373 (fowlpox). Generation of the recombinant viruses and preparation of the virus stock involved between 5-12 sequential passages, including one (1) to five (5) plaque purifications.

The recombinant poxviruses were passaged in CEF cell cultures in the absence of selection drugs. The absence of selection drugs allowed loss of the region encoding the selection genes, gpt and EGFP and the associated promoter (the selection cassette) from the inserted sequence. Recombination resulting in loss of the selection cassette is mediated by the F1 I4L region and a subsection of that region, the F1 repeat (F1 rpt), which flank the selection cassette in plasmid of each construct. These duplicated sequences were included to mediate recombination that results in loss of the selection cassette, leaving only the MUC1 and CEA sequences inserted in the described intergenic regions of the constructs described herein.

Plaque-purified virus lacking the selection cassette was prepared. Such preparation involved fifteen (15) passages including five (5) plaque purifications.

The presence of the MUC1 and CEA sequence and absence of parental MVA-BN virus in mBN336, mBN420, and mBN373 stocks was confirmed by PCR analysis, and nested PCR was used to verify the absence of the selection cassette (the gpt and EGFP genes/NPTII and mRFP1).

Expression of the MUC1 and CEA proteins was demonstrated in cells inoculated with MVA-BN-MUC1-CEA-TRICOM in vitro.

Example 2: PCR Analysis of MVA-mBN336 Passages 1-7

Genetic stability of MVA-mBN336B was evaluated by cultivation for seven passages. MVA-mBN336B encodes 5 human transgenes, with human Mucin 1 (MUC-1) and human Carcinoembryonic Antigen (CEA) being the target antigens of this vaccine candidate, and 3 genes encoding human immune costimulatory molecules (designated TRIad of COstimulatory Molecules, or TRICOM) as support for induction of a robust and directed immune response: leukocyte function-associated antigen-3 (LFA-3), intracellular adhesion molecule 1 (ICAM-1), and B7-1. The transgenes were inserted into three intergenic regions (IGR) of MVA-BN®: IGR 44/45 containing CEA, IGR 88/89 containing hMUC1, and IGR 148/149 containing the TRICOM genes. Transgene expression is driven by the poxvirus promoters 40 k-MVA1, 30 k, I3L and PrS.

Primary chicken embryo fibroblast (CEF) cells were prepared, seeded in roller bottles (RB) ($7 \times 10^7$ cells) in VP-SFM medium and incubated for 4 days at 37° C. VP-SFM medium was replace by 100 ml RPMI medium and the cells were infected with a MOI of approximately 0.3-00.1 referring to a cell number of $1 \times 10^8$ cells/RB and cultivated for 3 days at 30° C. After incubation, virus samples were harvested by freezing the RB at −20° C. for at least 16 h, followed by thawing of the RB to collect the cell virus suspension. The exact volume of the cell suspension was determined, virus samples were sonicated and subsequently aliquoted and stored at −80° C. This procedure was repeated six times resulting in seven passages.

PCR analysis of the inserted transgenes was performed for each passage after cultivation at 30° C. FIG. 9A shows the PCR results for stability of CEA over seven passages. FIG. 9B shows the PCR results for stability of MUC1 over seven passages. FIG. 9C shows the PCR results for the stability of the TRICOM over 7 passages. The recombination plasmids used for generation of MVA-mBN336B were used as positive controls, MVA-BN® was used as negative control (empty vector backbone) and H$_2$O was used as control for the PCR reaction.

FIGS. 10A and 10B illustrates an analysis of Passage 7 sample. FIG. 10A is a PCR amplification of Passage 7 samples send for analysis by sequencing. Individual PCR amplifications were performed for each individual transgenes: CEA, MUC1, and TRICOM. B) Electropherograms of the MUC1 nt-sequence depicting the loci containing the detected point mutation leading to a frame shift. The point mutation was detected in Passage 5 for the first time PCR amplification and in electropherograms of the MUC1 nt-sequence depicting the loci containing the detected point mutation leading to a frame shift. The point mutation was detected in passage 5 for the first time in an electropherogram analyzing mutations occurring in passages 5, 6, and 7.

Figure 3:
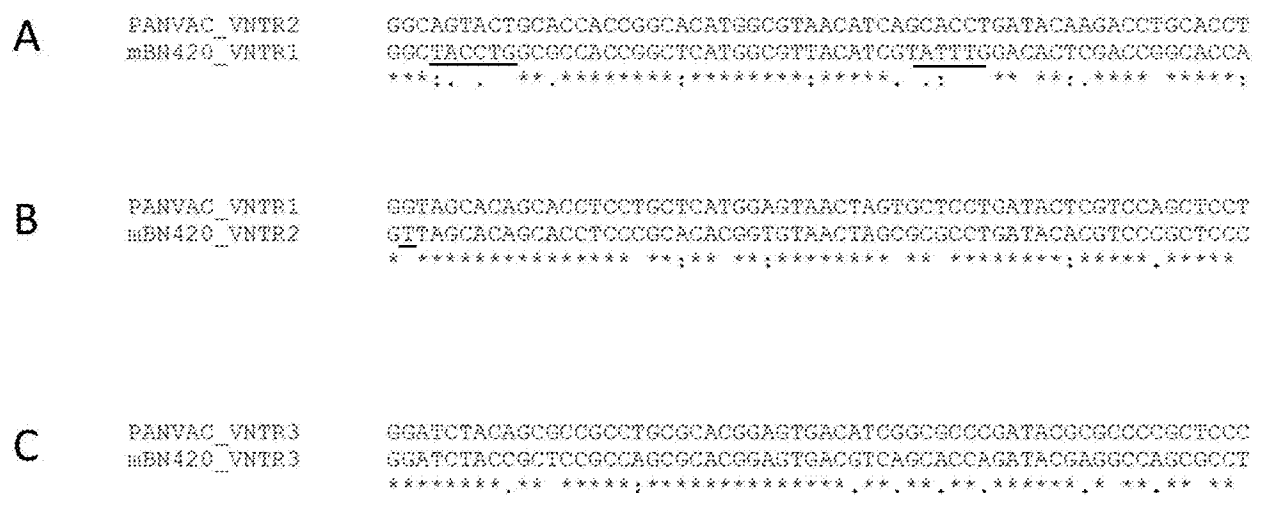
Figure 4A:
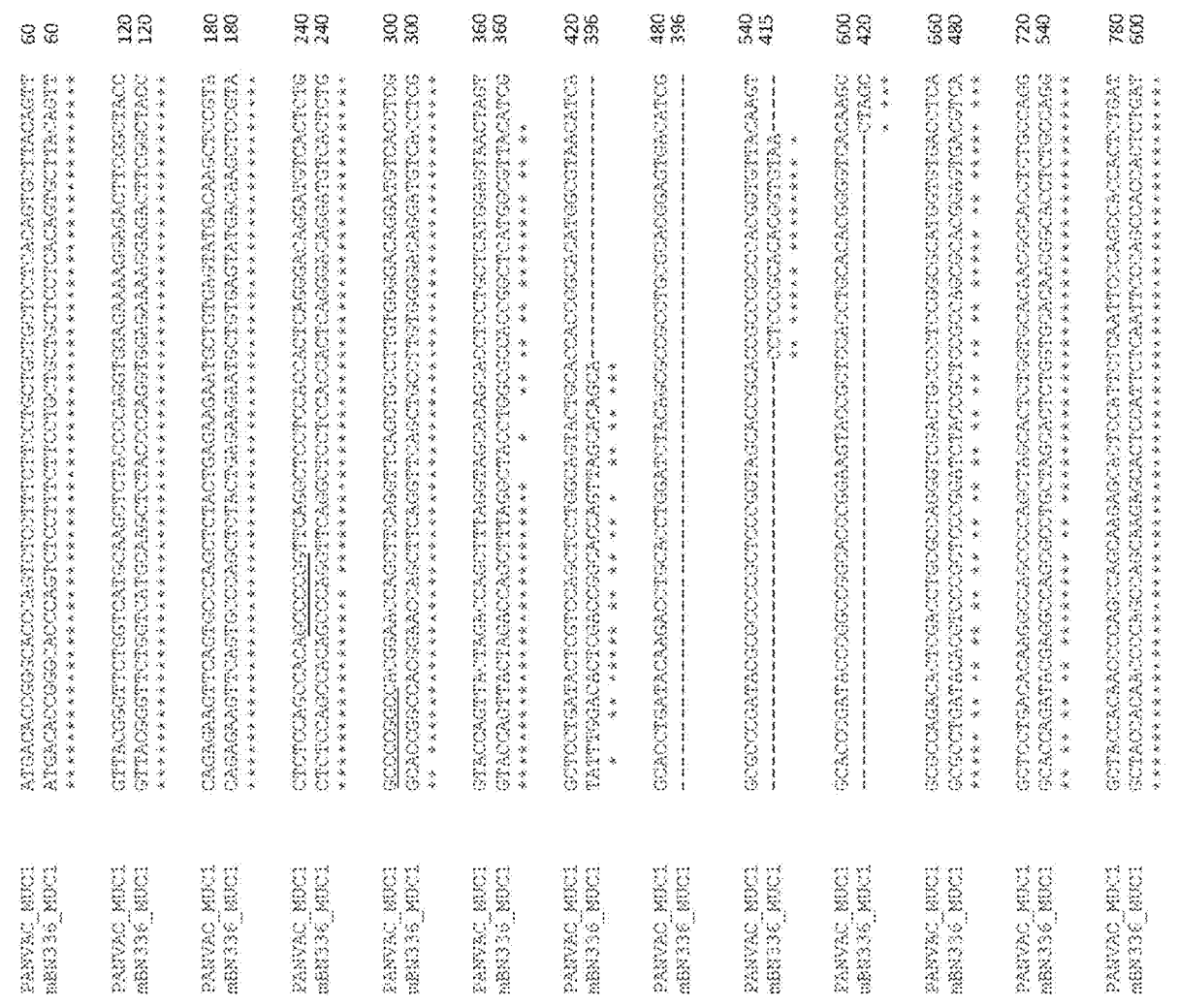
Figure 4B:
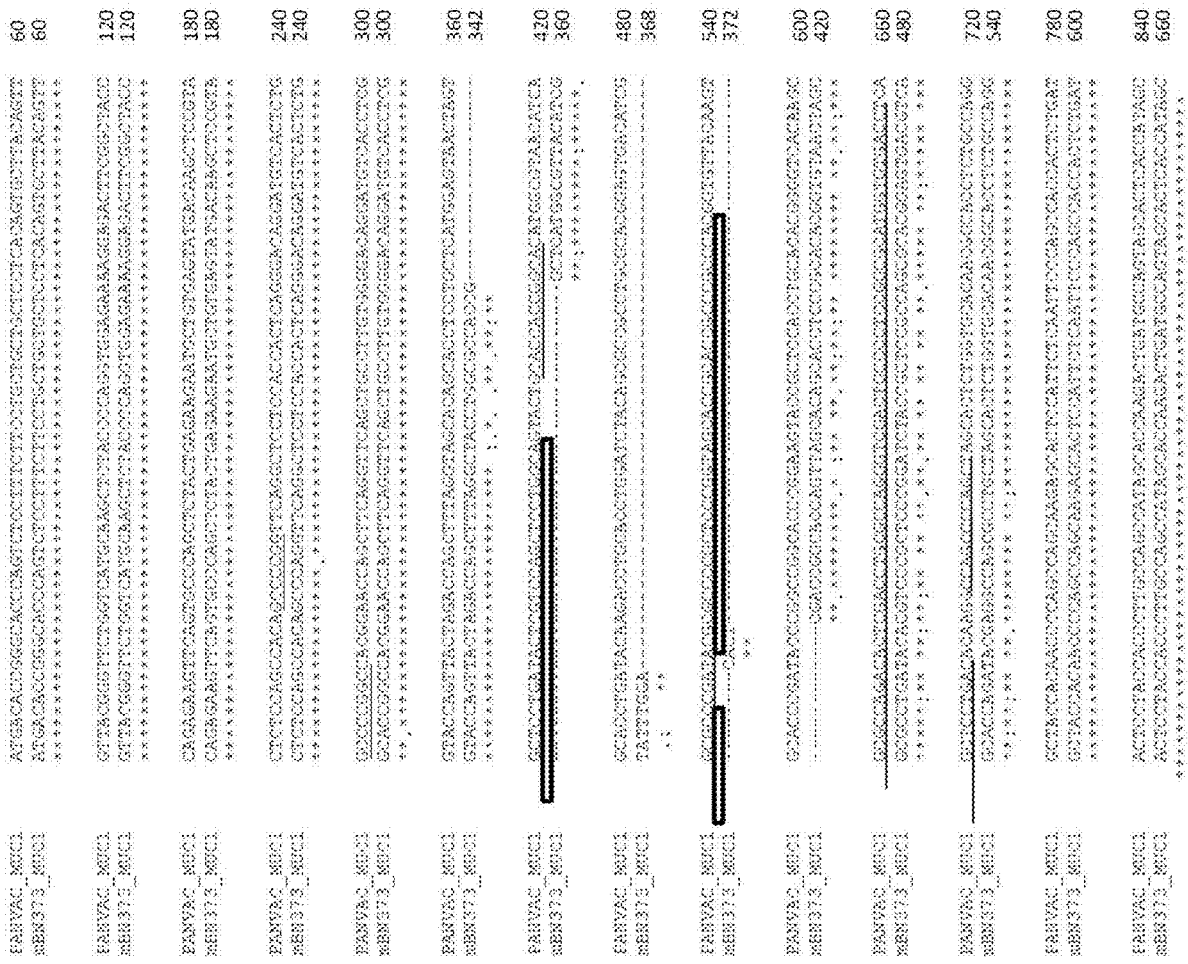
Figure 9:
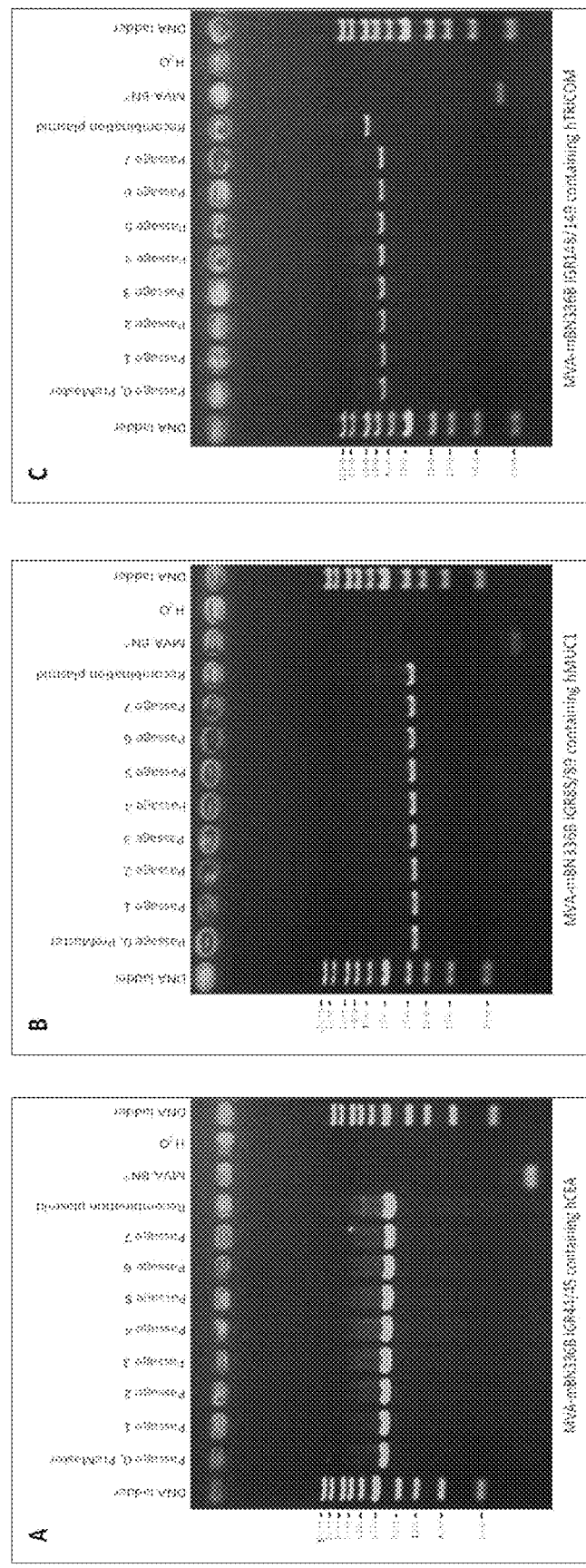
FIGS. 9A, 9B, and 9C illustrate experiments analyzing stability of a MUC1 transgene in mBN336.
Figure 10:
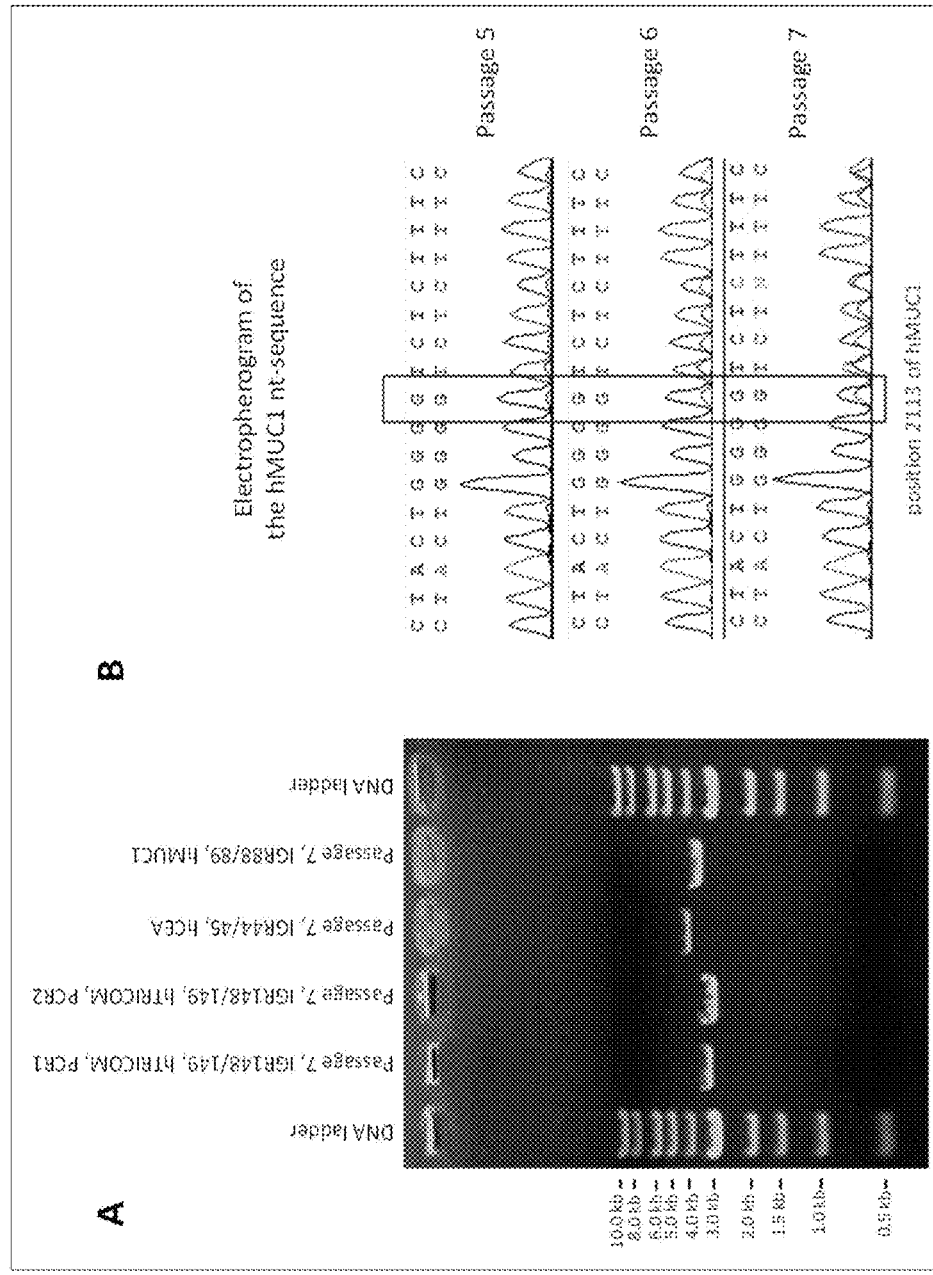
FIGS. 10A and 10B illustrate an analysis of Passages 5, 6, and 7 of mBN336.

Shown in FIGS. 9 and 10, the MUC1, CEA, and TRICOM combination in mBN336 demonstrated an improved and increased stability as compared to MUC1, CEA, and TRICOM transgenes in PANVAC-V and PANVAC-F (compare, e.g., FIG. 1 and Tables 1, and 2 with FIGS. 3 and 4). Starting at Passage 5, a frameshift mutation was detected within a minor population of the analyzed material.

The stability illustrated through passage 4 demonstrates the ability of the MVA-mBN336 to overcome the stability problems associated with PANVAC and other attempts to generate a stable poxvirus including MUC1. The stability of MVA-mBN336 is additionally advantageous, as manufacture and larger scale production of MVA-based vaccines are typically taken from MVAs at passage 3 or passage 4. Thus, because MVA-mBN336 is stable through passage 4, large scale production can begin and significant regulatory hurdles with regard to stability can be overcome.

Example 3: Improved Stability of FPV-mBN373

Genetic stability of FPV-mBN373B was evaluated over seven passages. Cultivation was performed in roller bottles (RB) as applied during large scale production used for manufacture of clinical trial material. Each passage was analyzed for virus titer by flow cytometry assay and the correct size of the transgene insert by PCR. In addition, the last passage (P7) was analyzed by sequencing of the transgenes.

Primary chicken embryo fibroblast (CEF) cells were prepared, seeded in RBs ($7\times10^7$ cells/RB) in VP-SFM medium and incubated for 3 days at 37° C. The VP-SFM medium was replaced by 100 ml RPMI medium and the cells were infected with a MOI of 0.1 referring to a cell number of $1\times10^8$/RB and cultivated for 4 days at 37° C. After incubation, virus samples were harvested by freezing the RB at −20° C. for at least 16 h, followed by thawing of the RB to collect the cell virus suspension. The exact volume of the cell suspension was determined, virus samples were sonicated, and subsequently aliquoted and stored at 80° C. The infectious virus titer was determined after each passage to monitor the virus titers and to enable the infection of the next passage with a defined MOI. This procedure was repeated six times resulting in seven passages.

Shown in FIG. 11A, PCR analysis of the inserted transgenes was performed for each passage after cultivation at 37° C. The recombination plasmid used for generation of FPV-mBN373B was used as positive control, FPV was used as negative control (empty vector backbone) and $H_2O$ was used as control for the PCR reaction.

Shown in FIG. 11B, sequencing of the seventh passage was performed after amplification of the BamHI J site containing the transgenes and at least 600 bp of each flanking region. The PCR amplicon of FPV-mBN373B analysed at passage seven (37° C.) resulted in the expected band size of 5566 bp (PCR1) and 5264 bp (PCR2), covering the inserted transgenes and at least 600 bp of each flanking region. The results showed a 100% identity of the assembled sequence compared to the theoretical sequence, confirming the genetic stability of FPV-mBN373B for 7 passages at 37° C.

In at least one aspect, the resulting stability of the MUC1 transgene, SEQ ID NO: 3, in mBN373 was surprising as both mBN373 and mBN336, include SEQ ID NO:3. Accordingly, while MUC1 of SEQ ID NO: 3 begins to show instability at Passage 5 in mBN336 (MVA virus), the same SEQ ID NO:3 is stable in mBN373 (fowlpox virus) at least until passage 7.

Example 4: Stability of MVA-mBN420

Genetic stability of MVA-mBN 420 was evaluated over seven passages. Cultivation was performed in roller bottles (RB) as applied during large scale production used for manufacture of clinical trial material. The study was performed at 30° C. and 34° C. using an MOI of approximately 0.05 to 0.1 and a virus incubation period of 4 days as these conditions are representative for a typical large scale production used for manufacture of clinical trial material. Each passage was analyzed for virus titer by flow cytometry assay and the correct size of the transgene insert by PCR.

Primary chicken embryo fibroblast (CEF) cells were prepared, seeded in RBs ($7 \times 10^7$ cells/RB) in VP-SFM medium and incubated for 3 days at 37° C. The VP-SFM medium was replaced by 100 ml RPMI medium and the cells were infected with a MOI of 0.05 to 0.1 referring to a cell number of $1 \times 10^8$/RB and cultivated for 4 days at 30° C. and 34° C. After incubation, virus samples were harvested by freezing the RB at −20° C. for at least 16 h, followed by thawing of the RB to collect the cell virus suspension. The virus samples were sonicated, and subsequently aliquoted and stored at 80° C. The infectious virus titer was determined after each passage to monitor the virus titers and to enable the infection of the next passage with a defined MOI. This procedure was repeated six times resulting in seven passages.

PCR analysis of the inserted transgenes was performed for each passage after cultivation at 30° C. 4. The results of passaging performed at 30° C. are shown in FIG. 12. The recombination plasmid used for generation of mBN420 was used as positive control, MVA-BN was used as negative control (empty vector backbone) and $H_2O$ was used as control for the PCR reaction.

Shown in FIG. 12, the stability of the MVA in mBN420 was decreased as compared to the MVA in mBN336 and the fowlpox virus in mBN373.

Example 5: Improved Stability of Additional Recombinant MVA and Recombinant Fowlpox Viruses Encoding MUC1 and CEA Generation of additional recombinant MVAs and recombinant fowlpox viruses of the present invention is conducted as described in Example 1. Nucleic acids encoding MUC1, CEA, and TRICOM transgenes comprising SEQ ID NOs: 31, 32, 33, or 34 (for MUC1) and SEQ ID NOs: 13 or 14 (for CEA) are inserted into MVA-BN as described in Example 1. Additionally, TRICOM is inserted into the MVA, the TRICOM sequences including SEQ ID NOs: 15 or 17 (for B7.1), SEQ ID NOs: 18 or 20 (for ICAM-1), and SEQ ID NOs: 21 or 23 (for LFA-3) are inserted into the MVA as described in Example 1.

Additionally, nucleic acids encoding MUC1 and CEA transgenes comprising SEQ ID NOs: 31, 32, 33, or 34 (for MUC1) and SEQ ID NOs: 13 or 14 (for CEA) are inserted into MVA-BN as described in Example 1. Additionally, TRICOM is inserted into the fowlpoxvirus, the TRICOM sequences including SEQ ID NOs: 15 or 17 (for B7.1), SEQ ID NOs: 18 or 20 (for ICAM-1), and SEQ ID NOs: 21 or 23 (for LFA-3) are inserted into the fowlpox as described in Example 1.

SEQ ID NOs: 31, 32, 33, or 34 each encode a MUC1 peptide comprising SEQ ID NO: 35.

The novel MUC1 nucleic acids of SEQ ID NOs: 31, 32, 33, and 34 each encode variations of the nucleic acids of the present invention without the agonist epitopes from WO 2013/103658. In several aspects, substitution and/or removal of the agonist epitopes do not affect stability of the recombinant poxviruses of the present invention, as the presence of the agonist epitopes function to enhance immunogenicity of the MUC1 rather than stability or instability.

Expression of the MUC1, CEA, and TRICOM proteins is demonstrated in cells inoculated with MVA-BN-MUC1-CEA-TRICOM in vitro as described in Example 1.

Improved genetic stability of transgenes in MVA and/or fowlpox viruses is evaluated over seven passages. Cultivation is performed in roller bottles (RB) as applied during large scale production used for manufacture of clinical trial material. The study is performed at 30° C., 34° C. or 37° C. (depending on the vector system used) using an MOI of approximately 00.05-00.1 and a virus incubation period of 2, 3, 4, 5, 6, or 7 days as these conditions are representative for a typical large scale production used for manufacture of clinical trial material. Each passage is analyzed for virus titer by flow cytometry assay and the correct size of the transgene insert by PCR. In addition, the last passage (P7) is analyzed by sequencing of the transgenes.

Primary chicken embryo fibroblast (CEF) cells are prepared, seeded in RBs ($7 \times 10^7$ cells/RB) in VP-SFM medium and incubated for 3 days at 37° C. The VP-SFM medium is replaced by 100 ml RPMI medium and the cells are infected with a MOI of 0.005 to 0.1 and cultivated for 4 days at 30° C., 34° C. or 37° C. (depending on the vector system used). After incubation, virus samples are harvested by freezing the RB at −20° C. for at least 16 h, followed by thawing of the RB to collect the cell virus suspension. The virus samples are sonicated, and subsequently aliquoted and stored at 80° C. The infectious virus titer is determined after each passage to monitor the virus titers and to enable the infection of the next passage with a defined MOI. This procedure is repeated six times resulting in seven passages.

PCR analysis of the inserted transgenes is performed for each passage after cultivation at 30° C., 34° C. or 37° C. (depending on the vector system). The recombination plasmid used for generation of each corresponding poxvirus (e.g., MVA-BN or fowlpox virus) is used as positive control, MVA-BN or fowlpoxvirus is used as negative control (empty vector backbone) and $H_2O$ is used as control for the PCR reaction.

Sequencing of the seventh passage is performed after amplification of the IGR site containing the transgenes and at least 600 bp of each flanking region. The PCR amplicon of each construct is analyzed at passage seven. Sequencing results of the MUC1, CEA and/or TRICOM nucleic acids are conducted to verify that the MVA and/or fowlpox virus is stable among the transgenes.

It will be apparent that the precise details of the methods or compositions described herein may be varied or modified without departing from the spirit of the described invention. We claim all such modifications and variations that fall within the scope and spirit of the claims below.

We claim:

1. A recombinant poxvirus which is stable through successive passaging of the recombinant poxvirus, the recombinant poxvirus comprising a nucleic acid encoding a MUC1 peptide having three Variable N-Terminal Repeat (VNTR) domains, wherein (a) the order of the nucleic acids encoding at least two VNTR domains of MUC1 is different from their order in PANVAC, and (b) the VNTR domains are codon optimized, wherein the recombinant poxvirus is stable through successive passaging of the recombinant poxvirus.

2. The recombinant poxvirus of claim 1, wherein said nucleic acid sequence comprises SEQ ID NO:2.

3. The recombinant poxvirus of claim 1, further comprising a nucleic acid encoding a carcinoembryonic antigen (CEA).

4. The recombinant poxvirus of claim 3, wherein the nucleic acid encoding a carcinoembryonic antigen (CEA) comprises at least one nucleotide substitution in at least one repetitive nucleotide region, wherein the at least one repetitive nucleotide region is defined as (a) three or more consecutively repeated G or C nucleotides and/or (b) three or more consecutively repeated T nucleotides.

5. The recombinant poxvirus of claim 4, wherein the nucleic acid encoding a carcinoembryonic antigen (CEA) comprises SEQ ID NO:13 or SEQ ID NO: 14.

6. The recombinant poxvirus of claim 1, wherein the recombinant poxvirus is selected from an orthopoxvirus and an avipoxvirus.

7. The recombinant poxvirus of claim 6, wherein the orthopoxvirus is a modified vaccinia virus Ankara (MVA) that is MVA-BN.

8. The recombinant poxvirus of claim 1, wherein the nucleic acid encoding a MUC1 peptide further comprises at least one nucleotide sequence encoding a peptide fragment selected from the group consisting of:

YLAPPAHGV, (SEQ ID NO: 24)

YLDTRPAPV, (SEQ ID NO: 25)

YLAIVYLIAL, (SEQ ID NO: 26)

YLIALAVCQV, (SEQ ID NO: 27)

YLSYTNPAV, (SEQ ID NO: 28)

and

SLFRSPYEK. (SEQ ID NO: 29)

9. The recombinant poxvirus of claim 1, wherein the poxvirus further comprises a nucleic acid encoding one or more co-stimulatory molecules selected from B7-1, ICAM-1, LFA-3, and combinations thereof.

10. A host cell comprising the recombinant poxvirus of claim 1.

11. A composition comprising the recombinant poxvirus of claim 1 that is suitable for administration as part of a homologous prime-boost regimen or a heterologous prime-boost regimen.

12. The recombinant poxvirus of claim 1 that comprises a nucleic acid encoding a MUC1 peptide in which the order of VNTR #2 and VNTR #1 is reversed.

13. The recombinant poxvirus of claim 1 that has stability through passage 7.

* * * * *

SEQUENCE LISTING

<160> NUMBER OF SEQ ID NOS: 35

<210> SEQ ID NO 1
<211> LENGTH: 1548
<212> TYPE: DNA
<213> ORGANISM: Artificial Sequence
<220> FEATURE:
<223> OTHER INFORMATION: MUC1 coding sequence from PANVAC

<400> SEQUENCE: 1

| | | | | |
|---|---|---|---|---|
| atgacaccgg | gcacccagtc | tcctttcttc | ctgctgctgc | tcctcacagt gcttacagtt | 60 |
| gttacgggtt | ctggtcatgc | aagctctacc | ccaggtggag | aaaaggagac ttcggctacc | 120 |
| cagagaagtt | cagtgcccag | ctctactgag | aagaatgctg | tgagtatgac aagctccgta | 180 |
| ctctccagcc | acagccccgg | ttcaggctcc | tccaccactc | agggacagga tgtcactctg | 240 |
| gccccggcca | cggaaccagc | ttcaggttca | gctgccttgt | ggggacagga tgtcaccctcg | 300 |
| gtaccagtta | ctagaccagc | tttaggtagc | acagcacctc | ctgctcatgg agtaactagt | 360 |
| gctcctgata | ctcgtccagc | tcctggcagt | actgcaccac | cggcacatgg cgtaacatca | 420 |
| gcacctgata | caagacctgc | acctggatct | acagcgccgc | ctgcgcacgg agtgacatcg | 480 |
| gcgcccgata | cgcgccccgc | tcccggtagc | accgcaccgc | ccgcccacgg tgttacaagt | 540 |
| gcacccgata | cccggccggc | acccggaagt | accgctccac | ctgcacacgg ggtcacaagc | 600 |
| gcgccagaca | ctcgacctgc | gccagggtcg | actgccccctc | cggcgcatgg tgtgacctca | 660 |
| gctcctgaca | caaggccagc | cccagctagc | actctggtgc | acaacggcac ctctgccagg | 720 |
| gctaccacaa | ccccagccag | caagagcact | ccattctcaa | ttcccagcca ccactctgat | 780 |
| actcctacca | cccttgccag | ccatagcacc | aagactgatg | ccagtagcac tcaccatagc | 840 |
| acggtacctc | ctctcacctc | ctccaatcac | agcacttctc | cccagttgtc tactggggtc | 900 |
| tctttctttt | tcctgtcttt | tcacatttca | aacctccagt | ttaattcctc tctggaagat | 960 |
| cccagcaccg | actactacca | agagctgcag | agagacattt | ctgaaatgtt tttgcagatt | 1020 |
| tataaacaag | ggggttttct | gggcctctcc | aatattaagt | tcaggccagg atctgtggtg | 1080 |
| gtacaattga | ctctggcctt | ccgagaaggt | accatcaatg | tccacgacgt ggagacacag | 1140 |
| ttcaatcagt | ataaaacgga | agcagcctct | cgatataacc | tgacgatctc agacgtcagc | 1200 |
| gtgagtgatg | tgccatttcc | tttctctgcc | cagtctgggg | ctggggtgcc aggctggggc | 1260 |
| atcgcgctgc | tggtgctggt | ctgtgttctg | gttgcgctgg | ccattgtcta tctcattgcc | 1320 |
| ttggctgtct | gtcagtgccg | ccgaaagaac | tacgggcagc | tggacatctt tccagcccgg | 1380 |
| gatacctacc | atcctatgag | cgagtacccc | acctaccaca | cccatgggcg ctatgtgccc | 1440 |
| cctagcagta | ccgatcgtag | cccctatgag | aaggtttctg | caggtaatgg tggcagcagc | 1500 |
| ctctcttaca | caaacccagc | agtggcagcc | acttctgcca | acttgtag | 1548 |

<210> SEQ ID NO 2
<211> LENGTH: 1365
<212> TYPE: DNA
<213> ORGANISM: Artificial Sequence
<220> FEATURE:
<223> OTHER INFORMATION: MUC1 coding sequence from mBN336

<400> SEQUENCE: 2

| | | | | |
|---|---|---|---|---|
| atgacaccgg | gcacccagtc | tcctttcttc | ctgctgctgc | tcctcacagt gcttacagtt | 60 |
| gttacgggtt | ctggtcatgc | aagctctacc | ccaggtggag | aaaaggagac ttcggctacc | 120 |
| cagagaagtt | cagtgcccag | ctctactgag | aagaatgctg | tgagtatgac aagctccgta | 180 |

-continued

```
ctctccagcc acagcccagg ttcaggctcc tccaccactc agggacagga tgtcactctg      240
gcaccggcca cggaaccagc ttcaggttca gctgccttgt ggggacagga tgtcacctcg      300
gtaccagtta ctagaccagc tttaggctac ctggcgccac cggctcatgg cgttacatcg      360
tatttggaca ctcgaccggc accagttagc acagcacctc ccgcacacgg tgtaactagc      420
gcgcctgata cacgtcccgc tcccggatct accgctccgc cagcgcacgg agtgacgtca      480
gcaccagata cgaggccagc gcctgctagc actctggtgc acaacggcac ctctgccagg      540
gctaccacaa ccccagccag caagagcact ccattctcaa ttcccagcca ccactctgat      600
actcctacca cccttgccag ccatagcacc aagactgatg ccagtagcac tcaccatagc      660
acggtacctc ctctcaccct ctccaatcac agcacttctc cccagttgtc tactggggtc      720
tctttctttt tcctgtcttt tcacatttca aacctccagt ttaattcctc tctgaagat       780 cccagcaccg actactacca agagctgcag agagacattt ctgaaatgtt tttgcagatt      840
tataaacaag ggggttttct ggcctctcc aatattaagt tcaggccagg atctgtggtg       900
gtacagttga ctctggcctt ccgagaaggt accatcaatg tccacgacgt ggagacacag      960
ttcaatcagt ataaaacgga agcagcctct cgatataacc tgacgatctc agacgtcagc     1020
gtgagtgatg tgccatttcc tttctctgcc cagtctgggg ctggggtgcc aggctggggc     1080
atcgcgctgc tggtgctggt ctgtgttctg gtttacctgg ccattgtcta tctcattgcc     1140
ttggctgtct gtcaggtccg ccgaaagaac tacgggcagc tggacatctt ccagcccgg     1200 gatacctacc atcctatgag cgagtacccc cctaccaca cccatgggcg ctatgtgccc      1260
cctagcagtc tgttccgtag cccctatgag aaggtttctg caggtaatgg tggcagctac     1320
ctctcttaca caaacccagc agtggcagcc acttctgcca acttg                     1365
```

<210> SEQ ID NO 3
<211> LENGTH: 1365
<212> TYPE: DNA
<213> ORGANISM: Artificial Sequence
<220> FEATURE:
<223> OTHER INFORMATION: MUC1 coding sequence from mBN373

<400> SEQUENCE: 3

```
atgacaccgg gcacccagtc tcctttcttc ctgctgctgc tcctcacagt gcttacagtt       60
gttacgggtt ctggtcatgc aagctctacc ccaggtggaa aaaggagac ttcggctacc       120 cagagaagtt cagtgcccag ctctactgag aagaatgctg tgagtatgac aagctccgta      180
ctctccagcc acagcccagg ttcaggctcc tccaccactc agggacagga tgtcactctg      240
gcaccggcca cggaaccagc ttcaggttca gctgccttgt ggggacagga tgtcacctcg      300
gtaccagtta ctagaccagc tttaggctac ctggcgccac cggctcatgg cgttacatcg      360
tatttggaca ctcgaccggc accagttagc acagcacctc ccgcacacgg tgtaactagc      420
gcgcctgata cacgtcccgc tcccggatct accgctccgc cagcgcacgg agtgacgtca      480
gcaccagata cgaggccagc gcctgctagc actctggtgc acaacggcac ctctgccagg      540
gctaccacaa ccccagccag caagagcact ccattctcaa ttcccagcca ccactctgat      600
actcctacca cccttgccag ccatagcacc aagactgatg ccagtagcac tcaccatagc      660
acggtacctc ctctcaccct ctccaatcac agcacttctc cccagttgtc tactggggtc      720
tctttctttt tcctgtcttt tcacatttca aacctccagt ttaattcctc tctgaagat       780 cccagcaccg actactacca agagctgcag agagacattt ctgaaatgtt tttgcagatt      840
```

```
tataaacaag ggggttttct gggcctctcc aatattaagt tcaggccagg atctgtggtg      900
gtacagttga ctctggcctt ccgagaaggt accatcaatg tccacgacgt ggagacacag      960
ttcaatcagt ataaaacgga agcagcctct cgatataacc tgacgatctc agacgtcagc     1020
gtgagtgatg tgccattttcc tttctctgcc cagtctgggg ctggggtgcc aggctggggc    1080
atcgcgctgc tggtgctggt ctgtgttctg gtttacctgg ccattgtcta tctcattgcc    1140
ttggctgtct gtcaggtccg ccgaaagaac tacgggcagc tggacatctt ccagcccgg     1200 gatacctacc atcctatgag cgagtacccc acctaccaca cccatgggcg ctatgtgccc    1260
cctagcagtc tgttccgtag cccctatgag aaggtttctg caggtaatgg tggcagctac    1320
ctctcttaca caaacccagc agtggcagcc acttctgcca acttg               1365
```

<210> SEQ ID NO 4
<211> LENGTH: 1365
<212> TYPE: DNA
<213> ORGANISM: Artificial Sequence
<220> FEATURE:
<223> OTHER INFORMATION: MUC1 coding sequence from mBN398 and mBN400

<400> SEQUENCE: 4

```
atgacacctg gcactcagtc accattcttc ctgctgttac tcttgacagt gcttacagtt       60
gttacaggtt ctggtcatgc aagctctacc ccaggtggag aaaaggagac ttcggctacc      120
cagcggagtt cagtgcctag ctctactgag aagaatgctg tgagtatgac aagctccgta      180
ctctccagcc acagcccagg ttcaggctcc agcaccactc aaggacagga tgtcactctg      240
gcaccggcca cggaaccagc ttcaggttca gctgccttgt ggggacagga tgtcacatcg      300
gtaccagtta ctagaccagc tttaggcagt actgcgccac cggctcatgg cgttacatcg      360
gcacctgaca ctcgaccggc accaggtagc acagcacctc ccgcacacgg tgtaactagc      420
gcgcctgata cacgtcccgc tcccggatct accgctccgc cagcgcacgg agtgacgtca      480
gcaccagata cgaggccagc gcctgctagc actctggtgc acaatggcac atctgccagg      540
gctaccacaa ctccagccag caagagcact ccattctcaa ttccaagcca tcactctgat      600
actcctacca cacttgccag ccatagcacc aagactgatg ccagtagcac tcaccatagc      660
acggtacctc cactcaccct atccaatcac agcacttctc ctcagttgtc tactggagtc      720
tccttctttt cctgtccctt tcacatttca aacttgcagt tcaattcttc cctgaaagat      780
cccagcaccg actactacca agagctgcag agagacattt ctgagatgtt cttgcagatt      840
tataaacaag gtggattcct tggcctctct aatattaagt tcaggccagg atctgtggtc      900
gtacagttga ctctggcctt cagagaaggt accatcaatg tccacgacgt ggagacacag      960
ttcaatcagt ataagacgga agcagcctca cgatataacc tgacgatctc agacgtcagc     1020
gttagtgatg tgccattttcc tttctctgcc cagtctggag ctggtgtgcc aggctggggc    1080
atcgcgctgc tcgtgttggt ctgtgttctg gttgcgctgg ccattgtcta tctcattgcc    1140
ttggctgttt gtcagtgcag acgcaagaac tacgacagc tggacatctt ccagctcgg      1200 gatacctacc atcctatgag cgagtaccct acctaccaca cacatggtcg ctatgtgcca    1260
cctagcagta ccgatcgtag tccctatgag aaagtttctg caggtaatgg tggcagcagc    1320
ctctcttaca caaacccagc agtggcagcc acttctgcca acttg               1365
```

<210> SEQ ID NO 5
<211> LENGTH: 1365
<212> TYPE: DNA
<213> ORGANISM: Artificial Sequence
<220> FEATURE:
<223> OTHER INFORMATION: MUC1 nucleic acid sequence from mBN420

<400> SEQUENCE: 5

```
atgacacctg gcactcagtc accattcttc ctgctgttac tcttgacagt gcttacagtt    60
gttacaggtt ctggtcatgc aagctctacc ccaggtggag aaaaggagac ttcggctacc   120
cagcggagtt cagtgcctag ctctactgag aagaatgctg tgagtatgac aagctccgta   180
ctctccagcc acagcccagg ttcaggctcc agcaccactc aaggacagga tgtcactctg   240
gcaccggcca cggaaccagc ttcaggttca gctgccttgt ggggacagga tgtcacatcg   300
gtaccagtta ctagaccagc tttaggctac ctggcgccac cggctcatgg cgttacatcg   360
tatttggaca ctcgaccggc accagttagc acagcacctc ccgcacacgg tgtaactagc   420
gcgcctgata cacgtcccgc tcccggatct accgctccgc cagcgcacgg agtgacgtca   480
gcaccagata cgaggccagc gcctgctagc actctggtgc acaatggcac atctgccagg   540
gctaccacaa ctccagccag caagagcact ccattctcaa ttccaagcca tcactctgat   600
actcctacca cacttgccag ccatagcacc aagactgatg ccagtagcac tcaccatagc   660
acggtacctc cactcacctc atccaatcac agcacttctc ctcagttgtc tactggagtc   720
tccttctttt tcctgtcctt tcacatttca aacttgcagt tcaattcttc cctggaagat   780
cccagcaccg actactacca agagctgcag agagacattt ctgagatgtt cttgcagatt   840
tataaacaag gtggattcct tggcctctct aatattaagt tcaggccagg atctgtggtc   900
gtacagttga ctctggcctt cagagaaggt accatcaatg tccacgacgt ggagacacag   960
ttcaatcagt ataagacgga agcagcctca cgatataacc tgacgatctc agacgtcagc  1020
gttagtgatg tgccatttcc tttctctgcc cagtctggag ctggtgtgcc aggctggggc  1080
atcgcgctgc tcgtgttggt ctgtgttctg gtttacctgg ccattgtcta tctcattgcc  1140
ttggctgttt gtcaggtcag acgcaagaac tacggacagc tggacatctt ccagctcgg   1200
gataccacc atcctatgag cgagtaccct acctaccaca cacatggtcg ctatgtgcca  1260
cctagcagtc tgttccgtag tccctatgag aaagtttctg caggtaatgg tggcagctac  1320
ctctcttaca caaacccagc agtggcagcc acttctgcca acttg             1365
```

<210> SEQ ID NO 6
<211> LENGTH: 515
<212> TYPE: PRT
<213> ORGANISM: Artificial Sequence
<220> FEATURE:
<223> OTHER INFORMATION: MUC 1 amino acid sequence as found in PANVAC

<400> SEQUENCE: 6

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95
```

```
Asp Val Thr Ser Val Pro Val Thr Arg Pro Ala Leu Gly Ser Thr Ala
            100                 105                 110

Pro Pro Ala His Gly Val Thr Ser Ala Pro Asp Thr Arg Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Ala Ser Thr Leu Val His Asn Gly Thr Ser Ala Arg
225                 230                 235                 240

Ala Thr Thr Thr Pro Ala Ser Lys Ser Thr Pro Phe Ser Ile Pro Ser
                245                 250                 255

His His Ser Asp Thr Pro Thr Thr Leu Ala Ser His Ser Thr Lys Thr
            260                 265                 270

Asp Ala Ser Ser Thr His His Ser Thr Val Pro Pro Leu Thr Ser Ser
            275                 280                 285

Asn His Ser Thr Ser Pro Gln Leu Ser Thr Gly Val Ser Phe Phe
        290                 295                 300

Leu Ser Phe His Ile Ser Asn Leu Gln Phe Asn Ser Ser Leu Glu Asp
305                 310                 315                 320

Pro Ser Thr Asp Tyr Tyr Gln Glu Leu Gln Arg Asp Ile Ser Glu Met
                325                 330                 335

Phe Leu Gln Ile Tyr Lys Gln Gly Gly Phe Leu Gly Leu Ser Asn Ile
            340                 345                 350

Lys Phe Arg Pro Gly Ser Val Val Gln Leu Thr Leu Ala Phe Arg
        355                 360                 365

Glu Gly Thr Ile Asn Val His Asp Val Glu Thr Gln Phe Asn Gln Tyr
    370                 375                 380

Lys Thr Glu Ala Ala Ser Arg Tyr Asn Leu Thr Ile Ser Asp Val Ser
385                 390                 395                 400

Val Ser Asp Val Pro Phe Pro Phe Ser Ala Gln Ser Gly Ala Gly Val
                405                 410                 415

Pro Gly Trp Gly Ile Ala Leu Leu Val Leu Val Cys Val Leu Val Ala
            420                 425                 430

Leu Ala Ile Val Tyr Leu Ile Ala Leu Ala Val Cys Gln Cys Arg Arg
            435                 440                 445

Lys Asn Tyr Gly Gln Leu Asp Ile Phe Pro Ala Arg Asp Thr Tyr His
    450                 455                 460

Pro Met Ser Glu Tyr Pro Thr Tyr His Thr His Gly Arg Tyr Val Pro
465                 470                 475                 480

Pro Ser Ser Thr Asp Arg Ser Pro Tyr Glu Lys Val Ser Ala Gly Asn
                485                 490                 495

Gly Gly Ser Ser Leu Ser Tyr Thr Asn Pro Ala Val Ala Ala Thr Ser
            500                 505                 510

Ala Asn Leu
```

```
<210> SEQ ID NO 7
<211> LENGTH: 60
<212> TYPE: DNA
<213> ORGANISM: Artificial Sequence
<220> FEATURE:
<223> OTHER INFORMATION: VNTR #2 coding sequence from PANVAC

<400> SEQUENCE: 7
ggcagtactg caccaccggc acatggcgta acatcagcac ctgatacaag acctgcacct      60

<210> SEQ ID NO 8
<211> LENGTH: 60
<212> TYPE: DNA
<213> ORGANISM: Artificial Sequence
<220> FEATURE:
<223> OTHER INFORMATION: VNTR #1 coding sequence from mBN420 and mBN336

<400> SEQUENCE: 8
ggctacctgg cgccaccggc tcatggcgtt acatcgtatt tggacactcg accggcacca      60

<210> SEQ ID NO 9
<211> LENGTH: 60
<212> TYPE: DNA
<213> ORGANISM: Artificial Sequence
<220> FEATURE:
<223> OTHER INFORMATION: VNTR #1 coding sequence from PANVAC

<400> SEQUENCE: 9
ggtagcacag cacctcctgc tcatggagta actagtgctc ctgatactcg tccagctcct      60

<210> SEQ ID NO 10
<211> LENGTH: 60
<212> TYPE: DNA
<213> ORGANISM: Artificial Sequence
<220> FEATURE:
<223> OTHER INFORMATION: VNTR #2 coding sequence from mBN420 and mBN336

<400> SEQUENCE: 10
gttagcacag cacctcccgc acacggtgta actagcgcgc ctgatacacg tcccgctccc      60

<210> SEQ ID NO 11
<211> LENGTH: 60
<212> TYPE: DNA
<213> ORGANISM: Artificial Sequence
<220> FEATURE:
<223> OTHER INFORMATION: VNTR #3 coding sequence from PANVAC

<400> SEQUENCE: 11
ggatctacag cgccgcctgc gcacggagtg acatcggcgc ccgatacgcg ccccgctccc      60

<210> SEQ ID NO 12
<211> LENGTH: 60
<212> TYPE: DNA
<213> ORGANISM: Artificial Sequence
<220> FEATURE:
<223> OTHER INFORMATION: VNTR #3 coding sequence from mBN420 and mBN336

<400> SEQUENCE: 12
ggatctaccg ctccgccagc gcacggagtg acgtcagcac cagatacgag gccagcgcct      60

<210> SEQ ID NO 13
<211> LENGTH: 2103
<212> TYPE: DNA
<213> ORGANISM: Artificial Sequence
```

<220> FEATURE:
<223> OTHER INFORMATION: CEA coding sequence from PANVAC

<400> SEQUENCE: 13

| | | | | | |
|---|---|---|---|---|---|
| atggagtctc | cctcggcccc | tccccacaga | tggtgcatcc | cctggcagag | gctcctgctc | 60 |
| acagcctcac | ttctaacctt | ctggaacccg | cccaccactg | ccaagctcac | tattgaatcc | 120 |
| acgccgttca | atgtcgcaga | ggggaaggag | gtgcttctac | ttgtccacaa | tctgccccag | 180 |
| catcttttttg | gctacagctg | gtacaaaggt | gaaagagtgg | atggcaaccg | tcaaattata | 240 |
| ggatatgtaa | taggaactca | acaagctacc | ccagggcccg | catacagtgg | tcgagagata | 300 |
| atataccccca | atgcatccct | gctgatccag | aacatcatcc | agaatgacac | aggattctac | 360 |
| accctacacg | tcataaagtc | agatcttgtg | aatgaagaag | caactggcca | gttccgggta | 420 |
| tacccggaac | tccctaagcc | ttctattagc | tccaataata | gtaagcctgt | cgaagacaaa | 480 |
| gatgccgtcg | cttttacatg | cgagcccgaa | actcaagacg | caacatatct | ctggtgggtg | 540 |
| aacaaccagt | ccctgcctgt | gtcccctaga | ctccaactca | gcaacggaaa | tagaactctg | 600 |
| accctgttta | acgtgaccag | gaacgacaca | gcaagctaca | aatgcgaaac | ccaaaatcca | 660 |
| gtcagcgcca | ggaggtctga | ttcagtgatt | ctcaacgtgc | tttacggacc | cgatgctcct | 720 |
| acaatcagcc | ctctaaacac | aagctataga | tcaggggaaa | atctgaatct | gagctgtcat | 780 |
| gccgctagca | atcctcccgc | ccaatacagc | tggtttgtca | atggcacttt | ccaacagtcc | 840 |
| acccaggaac | tgttcattcc | caatattacc | gtgaacaata | gtggatccta | cacgtgccaa | 900 |
| gctcacaata | gcgacaccgg | actcaaccgc | acaaccgtga | cgacgattac | cgtgtatgag | 960 |
| ccaccaaaac | cattcataac | tagtaacaat | tctaacccag | ttgaggatga | ggacgcagtt | 1020 |
| gcattaactt | gtgagccaga | gattcaaaat | accacttatt | tatggtgggt | caataaccaa | 1080 |
| agtttgccgg | ttagcccacg | cttgcagttg | tctaatgata | accgcacatt | gacactcctg | 1140 |
| tccgttactc | gcaatgatgt | aggacccttat | gagtgtggca | ttcagaatga | attatccgtt | 1200 |
| gatcactccg | accctgttat | ccttaatgtt | ttgtatggcc | cagacgaccc | aactatatct | 1260 |
| ccatcataca | cctactaccg | tcccggcgtg | aacttgagcc | tttcttgcca | tgcagcatcc | 1320 |
| aaccccccctg | cacagtactc | ctggctgatt | gatggaaaca | ttcagcagca | tactcaagag | 1380 |
| ttatttatatta | gcaacataac | tgagaagaac | agcggactct | atacttgcca | ggccaataac | 1440 |
| tcagccagtg | gtcacagcag | gactacagtt | aaaacaataa | ctgtttccgc | ggagctgccc | 1500 |
| aagccctcca | tctccagcaa | caactccaaa | cccgtggagg | acaaggatgc | tgtggccttc | 1560 |
| acctgtgaac | ctgaggctca | gaacacaacc | tacctgtggt | gggtaaatgg | tcagagcctc | 1620 |
| ccagtcagtc | ccaggctgca | gctgtccaat | ggcaacagga | ccctcactct | attcaatgtc | 1680 |
| acaagaaatg | acgcaagagc | ctatgtatgt | ggaatccaga | actcagtgag | tgcaaaccgc | 1740 |
| agtgacccag | tcaccctgga | tgtcctctat | gggccggaca | ccccccatcat | ttccccccca | 1800 |
| gactcgtctt | acctttcggg | agcggacctc | aacctctcct | gccactcggc | tctaacccca | 1860 |
| tccccgcagt | attcttggcg | tatcaatggg | ataccgcagc | aacacacaca | agttctctttt | 1920 |
| atcgccaaaa | tcacgccaaa | taataacggg | acctatgcct | gttttgtctc | taacttggct | 1980 |
| actggccgca | taattccat | agtcaagagc | atcagtgtct | ctgcatctgg | aacttctcct | 2040 |
| ggtctctcag | ctggggccac | tgtcggcatc | atgattggag | tgctggttgg | ggttgctctg | 2100 |
| ata | | | | | | 2103 |

<210> SEQ ID NO 14

<211> LENGTH: 2103
<212> TYPE: DNA
<213> ORGANISM: Artificial Sequence
<220> FEATURE:
<223> OTHER INFORMATION: CEA coding sequence from mBN373 and mBN420

<400> SEQUENCE: 14

| | | | | | |
|---|---|---|---|---|---|
| atggagtctc | cctcggctcc | tccacacaga | tggtgcatcc | cttggcagag | gctcctgctc | 60 |
| acagcctcac | ttctaacctt | ctggaacccg | cccaccactg | ccaagctcac | tattgaatcc | 120 |
| acgccgttca | atgtcgcaga | ggggaaggag | gtgcttctac | ttgtccacaa | tctgcctcag | 180 |
| catctctttg | gctacagctg | gtacaaaggt | gaaagagtgg | atggcaaccg | tcaaattata | 240 |
| ggatatgtaa | taggaactca | acaagctact | ccagggcccg | catacagtgg | tcgagagata | 300 |
| atatcccta | atgcatccct | gctgatccag | aacatcatcc | agaatgacac | aggattctac | 360 |
| accctacacg | tcataaagtc | agatcttgtg | aatgaagaag | caactggcca | gttccgggta | 420 |
| taccctgaac | tccctaagcc | ttctattagc | tccaataata | gtaagcctgt | cgaagacaaa | 480 |
| gatgccgtcg | ctttcacatg | cgagcccgaa | actcaagacg | caacatatct | ctggtgggtg | 540 |
| aacaaccagt | ccctgcctgt | gtctcctaga | ctccaactca | gcaacggaaa | tagaactctg | 600 |
| accctgttta | acgtgaccag | gaacgacaca | gcaagctaca | aatgcgaaac | ccaaaatcca | 660 |
| gtcagcgcca | ggaggtctga | ttcagtgatt | ctcaacgtgc | tttacggacc | cgatgctcct | 720 |
| acaatcagcc | ctcaaacac | aagctataga | tcaggagaaa | atctgaatct | gagctgtcat | 780 |
| gccgctagca | atcctccagc | tcaatacagc | tggtttgtca | atggcacttt | ccaacagtcc | 840 |
| acccaggaac | tgttcattcc | caatattacc | gtgaacaata | gtggatccta | cacgtgccaa | 900 |
| gctcacaata | gcgacaccgg | actcaaccgc | acaaccgtga | cgacgattac | cgtgtatgag | 960 |
| ccaccaaaac | cattcataac | tagtaacaat | tctaacccag | ttgaggatga | ggacgcagtt | 1020 |
| gcattaactt | gtgagccaga | gattcaaaat | accacttatt | tatggtgggt | caataaccaa | 1080 |
| agtttgccgg | ttagcccacg | cttgcagttg | tctaatgata | accgcacatt | gacactcctg | 1140 |
| tccgttactc | gcaatgatgt | aggaccttat | gagtgtggca | ttcagaatga | attatccgtt | 1200 |
| gatcactccg | accctgttat | ccttaatgtt | ttgtatggcc | cagacgaccc | aactatatct | 1260 |
| ccatcataca | cctactaccg | tccceggcgtg | aacttgagcc | tttcttgcca | tgcagcatct | 1320 |
| aatccacctg | cacagtactc | ctggctgatt | gatggaaaca | ttcagcagca | tactcaagag | 1380 |
| ttatttataa | gcaacataac | tgagaagaac | agcggactct | atacttgcca | ggccaataac | 1440 |
| tcagccagtg | gtcacagcag | gactacagtt | aaaacaataa | ctgtttccgc | ggagctgccc | 1500 |
| aagccctcca | tctccagcaa | caactccaaa | cccgtggagg | acaaggatgc | tgtggccttc | 1560 |
| acctgtgaac | ctgaggctca | gaacacaacc | tacctgtggt | gggtaaatgg | tcagagcctc | 1620 |
| ccagtcagtc | ccaggctgca | gctgtccaat | ggcaacagga | ccctcactct | attcaatgtc | 1680 |
| acaagaaatg | acgcaagagc | ctatgtatgt | ggaatccaga | actcagtgag | tgcaaaccgc | 1740 |
| agtgacccag | tcaccctgga | tgtcctctat | ggaccggaca | cacccatcat | ttcacctcca | 1800 |
| gactcgtctt | acctttcggg | agcggacctc | aacctctcct | gccactcggc | tctaacccca | 1860 |
| tctccgcagt | attcttggcg | tatcaatggg | ataccgcagc | aacacacaca | agttctcttt | 1920 |
| atcgccaaaa | tcacgccaaa | taataacggg | acctatgcct | gttttgtctc | taacttggct | 1980 |
| actggccgca | ataattccat | agtcaagagc | atcacagtct | ctgcatctgg | aacttctcct | 2040 |
| ggtctctcag | ctggagccac | tgtcggcatc | atgattggag | tgctggttgg | ggttgctctg | 2100 |
| ata | | | | | | 2103 |

<210> SEQ ID NO 15
<211> LENGTH: 864
<212> TYPE: DNA
<213> ORGANISM: Artificial Sequence
<220> FEATURE:
<223> OTHER INFORMATION: Optimized B7.1 coding sequence from mBN373 and mBN420

<400> SEQUENCE: 15

| | | | | | |
|---|---|---|---|---|---|
| atgggacaca | ccagaaggca | gggcacaagc | ccatccaagt | gtccctacct | gaacttcttt | 60 |
| cagctcctgg | tgctggctgg | cctgtcccac | ttctgctccg | gagtgatcca | cgtgaccaag | 120 |
| gaggtcaaag | aagtcgccac | actgagctgc | gggcacaatg | tgtccgtgga | ggaactggct | 180 |
| cagacacgga | tctactggca | gaaagagaag | aaaatggtgc | tgaccatgat | gtccggcgac | 240 |
| atgaacatct | ggcctgagta | caagaaccgc | accatcttcg | acatcaccaa | caatctgagc | 300 |
| atcgtgatcc | tcgctctgag | gcccctccgac | gagggaacat | acgagtgcgt | ggtgctgaag | 360 |
| tacgagaagg | acgccttcaa | cgcgagcac | ctggccgagg | tcaccctgtc | cgtgaaggca | 420 |
| gacttcccaa | cacccagcat | cagcgacttc | gagatcccta | ccagcaacat | ccggcggatt | 480 |
| atctgcagca | cctccggagg | cttcccagag | cctcacctga | gctggctcga | aacggcgaa | 540 |
| gagctcaacg | ccatcaacac | taccgtgtcc | caggaccctg | agacagagct | gtacgctgtg | 600 |
| agcagcaagc | tggacttcaa | catgaccaca | atcacagct | tatgtgcct | catcaagtac | 660 |
| ggccacctga | gagtgaatca | gaccttcaac | tggaatacaa | ccaagcagga | acacttccca | 720 |
| gacaatctcc | tgccctcctg | ggctatcaca | ctgattagcg | tgaatggcat | cttcgtgatc | 780 |
| tgctgtctga | cctactgctt | cgctcccaga | tgccgggagc | gcaggagaaa | cgagaggctg | 840 |
| agacgggaat | ccgtgaggcc | cgtg | | | | 864 |

<210> SEQ ID NO 16
<211> LENGTH: 864
<212> TYPE: DNA
<213> ORGANISM: Artificial Sequence
<220> FEATURE:
<223> OTHER INFORMATION: B7.1 coding sequence from PANVAC

<400> SEQUENCE: 16

| | | | | | |
|---|---|---|---|---|---|
| atgggccaca | cacggaggca | gggaacatca | ccatccaagt | gtccatacct | caatttcttt | 60 |
| cagctcttgg | tgctggctgg | tctttctcac | ttctgttcag | gtgttatcca | cgtgaccaag | 120 |
| gaagtgaaag | aagtggcaac | gctgtcctgt | ggtcacaatg | tttctgttga | agagctggca | 180 |
| caaactcgca | tctactggca | aaaggagaag | aaaatggtgc | tgactatgat | gtctggagac | 240 |
| atgaatatat | ggcccgagta | caagaaccgg | accatctttg | atatcactaa | taacctctcc | 300 |
| attgtgatcc | tggctctgcg | cccatctgac | gagggcacat | acgagtgtgt | tgttctgaag | 360 |
| tatgaaaaag | acgcttttca | gcgggaacac | ctggctgaag | tgacgttatc | agtcaaagct | 420 |
| gacttcccta | cacctagtat | atctgacttt | gaaattccaa | cttctaatat | tagaaggata | 480 |
| atttgctcaa | cctctggagg | ttttccagag | cctcacctct | cctggttgga | aaatggagaa | 540 |
| gaattaaatg | ccatcaacac | aacagtttcc | caagatcctg | aaactgagct | ctatgctgtt | 600 |
| agcagcaaac | tggatttcaa | tatgacaacc | aaccacagct | tcatgtgtct | catcaagtat | 660 |
| ggacatttaa | gagtgaatca | gaccttcaac | tggaatacaa | ccaagcaaga | gcattttcct | 720 |
| gataacctgc | tcccatcctg | ggccattacc | ttaatctcag | taaatggaat | tttcgtgata | 780 |
| tgctgcctga | cctactgctt | tgccccacgc | tgcagagaga | aaggaggaa | tgagagattg | 840 | agaagggaaa gtgtacgccc tgta                                            864

<210> SEQ ID NO 17
<211> LENGTH: 864
<212> TYPE: DNA
<213> ORGANISM: Artificial Sequence
<220> FEATURE:
<223> OTHER INFORMATION: Optimized B7.1 coding sequence from mBN336

<400> SEQUENCE: 17
atgggccaca ccagaaggca gggcaccagc ccctccaagt gcccctacct gaacttcttc     60
cagctcctgg tgctggccgg cctgtcccac ttctgctccg gcgtgatcca cgtgaccaaa    120
gaggtcaaag aagtcgccac actgagctgc ggccacaatg tgtccgtgga ggaactggct    180
cagacccgga tctactggca gaaagaaaag aaaatggtgc tgaccatgat gtccggcgac    240
atgaacatct ggcctgagta caagaaccgc accatcttcg acatcaccaa caacctgagc    300
atcgtgatcc tcgccctgag gcccctcgac gagggcacct acgagtgcgt ggtgctgaag    360
tacgagaagg acgccttcaa gcgcgagcac ctggccgagg tcaccctgtc cgtgaaggcc    420
gacttcccaa cccccagcat cagcgacttc gagatcccaa ccagcaacat ccggcggatc    480
atctgcagca cctccggcgg cttccccgag cctcacctga gctggctcga acggcgaa     540 gaactcaacg ccatcaacac taccgtgtcc caggaccccg agacagagct gtacgccgtg    600
agcagcaagc tggacttcaa catgaccaca accacagct ttatgtgcct catcaagtac     660
ggccacctga gtgaatca gaccttcaac tggaacacca ccaagcagga acacttcccc      720
gacaatctgc tgccctcctg ggctatcacc ctgattagcg tgaatggcat cttcgtgatc    780
tgctgtctga cctactgctt cgcccccaga tgccgggagc ggcggagaaa cgagcggctg    840
cggcgggaat ccgtgaggcc cgtg                                            864

<210> SEQ ID NO 18
<211> LENGTH: 1596
<212> TYPE: DNA
<213> ORGANISM: Artificial Sequence
<220> FEATURE:
<223> OTHER INFORMATION: Optimized ICAM-1 coding sequence from mBN373
        and mBN420

<400> SEQUENCE: 18
atggctccta gctcacctag accagctctg cctgccctgc tcgtgctgct cggagctctg     60
ttccctggac caggcaacgc ccagaccagc gtgtcaccta gcaaagtgat tctgccccaga   120 ggaggctccg tgctggtcac atgtagcacc agctgcgacc agcccaagct cctcgggatc    180
gagacacctc tgcccaagaa agagctgctg ctgccaggca caatcggaaa gtgtacgag    240 ctgtccaatg tgcaggaaga tagccagccc atgtgctact ccaactgtcc cgacggccag    300
agcaccgcca gaccctttct gaccgtgtac tggacacctg agcgggtgga actggctcca    360
ctgcccagct ggcagccagt gggcaagaat ctgacccctg cggtgcaggt ggaaggcgga    420
gctcccagag ccaacctgac agtggtgctc ctgagaggcg agaaagagct gaagcgggaa    480
cctgccgtgg gcgagccagc cgaagtgacc acaacccgtgc tcgtgcggag ggaccaccac    540
ggagccaact tcagctgcag aaccgagctg gacctcaggc cacagggcct ggaactgttc    600
gagaacacca cgctcccta ccagctccag accttcgtgc tcccagcaac accacctcag    660
ctggtgtcac tcgggtgct ggaagtggac acccagggca cagtcgtgtg cagcctggac    720
ggcctgtttc ccgtgtccga agctcaggtc cacctggctc tcggagacca gagactgaac    780

```
cctaccgtga cctacggcaa tgacagcttc agcgccaagg cctccgtgtc cgtgaccgcc    840
gaggatgaag gcacccagag gctgacatgc gccgtgattc tgggcaacca gagccaggaa    900
accctgcaga ccgtcaccat ctatagcttc cctgcaccta atgtgatcct gacaaagccc    960
gaggtgtccg agggcactga agtgaccgtg aaatgcgagg cccaccctag agccaaagtg   1020
accctgaacg gcgtgccagc ccagccactc ggaccaagag cacagctcct gctgaaagcc   1080
acacccgagg ataacggccg gtccttctcc tgcagcgcta ccctcgaagt ggccggacag   1140
ctgatccaca gaaccagac cagagagctg agagtgctgt acggccctag actggacgag   1200
agagactgcc caggcaactg gacctggccc gagaactccc agcagacacc catgtgccag   1260
gcttggggca acccactgcc agagctgaag tgcctgaagg acggcacctt ccctctgccc   1320
atcggcgagt ccgtgacagt gaccaggac ctggaaggca cctacctgtg cagagccaga   1380
tccacacagg gcgaagtgac acgggaggtc accgtgaatg tgctgtcacc tcgctacgag   1440
atcgtgatca tcaccgtggt cgctgcagct gtgatcatgg gcacagccgg actgagcaca   1500
tacctgtaca accggcagcg gaagatcaag aagtacaggc tgcagcaggc ccagaaaggc   1560
acacccatga agcccaacac ccaggccact cctccc                             1596

<210> SEQ ID NO 19
<211> LENGTH: 1596
<212> TYPE: DNA
<213> ORGANISM: Artificial Sequence
<220> FEATURE:
<223> OTHER INFORMATION: ICAM-1 coding sequence from PANVAC

<400> SEQUENCE: 19
atggctccca gcagccccg gcccgcgctg cccgcactcc tggtcctgct cggggctctg     60
ttcccaggac ctggcaatgc ccagacatct gtgtccccct caaaagtcat cctgccccgg    120
ggaggctccg tgctggtgac atgcagcacc tcctgtgacc agcccaagtt gttgggcata    180 gagacccct tgcctaaaaa ggagttgctc ctgcctggga caaccggaa ggtgtatgaa     240 ctgagcaatg tgcaagaaga tagccaacca atgtgctatt caaactgccc tgatgggcag    300
tcaacagcta aaaccttcct caccgtgtac tggactccag aacgggtgga actggcaccc    360
ctcccctctt ggcagccagt gggcaagaac cttaccctac gctgccaggt ggagggtggg    420
gcaccccggg ccaacctcac cgtggtgctg ctccgtgggg agaaggagct gaaacgggag    480
ccagctgtgg gggagcccgc tgaggtcacg accacggtgc tggtgaggag agatcaccat    540
ggagccaatt tctcgtgccg cactgaactg gacctgcggc ccaagggct ggagctgttt    600 gagaacacct cggccccta ccagctccag acctttgtcc tgccagcgac tccccacaa    660 cttgtcagcc ccgggtcct agaggtggac acgcagggga ccgtggtctg ttccctggac    720
gggctgttcc cagtctcgga ggcccaggtc cacctggcac tgggggacca gaggttgaac    780
cccacagtca cctatggcaa cgactccttc tcggccaagg cctcagtcag tgtgaccgca    840
gaggacgagg gcacccagcg gctgacgtgt gcagtaatac tggggaacca gagccaggag    900
acactgcaga cagtgaccat ctacagcttt ccggcgccca acgtgattct gacgaagcca    960
gaggtctcag aagggaccga ggtgacagtg aagtgtgagg cccacccag agccaaggtg   1020 acgctgaatg ggttccagc ccagccactg ggcccaggg ccagctcct gctgaaggcc     1080 acccagagg acaacggcg cagcttctcc tgctctgcaa ccctgaggt ggccggccag     1140 cttatacaca gaaccagac ccgggagctt cgtgtcctgt atggccccg actggacgag    1200
```

```
agggattgtc cgggaaactg dacgtggcca gaaaattccc agcagactcc aatgtgccag   1260
gcttggggga acccattgcc cgagctcaag tgtctaaagg atggcacttt cccactgccc   1320
atcggggaat cagtgactgt cactcgagat cttgagggca cctacctctg tcgggccagg   1380
agcactcaag gggaggtcac ccgcgaggtg accgtgaatg tgctctcccc ccggtatgag   1440
attgtcatca tcactgtggt agcagccgca gtcataatgg gcactgcagg cctcagcacg   1500
tacctctata accgccagcg gaagatcaag aaatacagac tacaacaggc ccaaaaaggg   1560 accccccatga aaccgaacac acaagccacg cctccc                           1596
```

<210> SEQ ID NO 20
<211> LENGTH: 1596
<212> TYPE: DNA
<213> ORGANISM: Artificial Sequence
<220> FEATURE:
<223> OTHER INFORMATION: Optimized ICAM-1 coding sequence from mBN336

<400> SEQUENCE: 20

```
atggcccta gcagccctag accagccctg cctgccctgc tggtgctgct gggcgctctg    60
ttccccggac ccggcaacgc ccagaccagc gtgtccccca gcaaagtgat tctgcccaga   120
ggcggctccg tgctggtcac atgtagcacc agctgcgacc agcccaagct cctcgggatc   180
gagacacccc tgcccaagaa agagctgctg ctgcccggca caaccggaaa gtgtacgag   240 ctgtccaatg tgcaggaaga tagccagccc atgtgctact ccaactgccc cgacggccag   300
agcaccgcca agacctttct gaccgtgtac tggacccccg agcgggtgga actggcccca   360
ctgcccagct ggcagcccgt gggcaagaat ctgaccctgc ggtgccaggt ggaaggcgga   420 gccccccagag ccaacctgac agtggtgctc ctgcggggcg aaaaagagct gaagcgggag   480
cctgccgtgg gcgagccagc cgaagtgacc acaaccgtgc tcgtgcggag ggaccaccac   540
ggcgccaact tcagctgcag aaccgagctg gacctcaggc cacagggcct ggaactgttc   600
gagaacacca cgcgcccccta ccagctccag accttcgtgc tcccagcaac ccccctcag   660 ctggtgtccc ctcgggtgct ggaagtggac acccagggca cagtcgtgtg cagcctggac   720
ggcctgtttc ccgtgtccga agctcaggtc cacctggctc tcggggacca gagactgaac   780
cctaccgtga cctacggcaa tgacagcttc agcgccaagg cctccgtgtc cgtgaccgcc   840
gaggatgagg gcacccagag gctgacatgc gccgtgattc tgggcaacca gagccaggaa   900
accctgcaga ccgtcaccat ctatagcttc cctgccccca atgtgatcct gacaaagccc   960
gaggtgtccg agggcactga agtgaccgtg aaatgcgagg cccaccccag gccaaagtg   1020 accctgaacg gcgtgccagc ccagccactc ggaccaagag cacagctcct gctgaaagcc   1080 accccgagg ataacggccg gtccttctcc tgcagcgcta ccctcgaagt ggccgggcag   1140
ctgatccaca gaaccagac ccgggagctg agagtgctgt acggcccag actggacgag   1200 agagactgcc ccggcaactg gacctggccc gagaactccc agcagacccc catgtgccag   1260
gcttggggca acccactgcc agagctgaag tgcctgaagg acggcacctt ccctctgccc   1320
atcggcgagt ccgtgacagt gacccgggac ctggaaggca cctacctgtg ccgggccaga   1380
tccacacagg gcgaagtgac acggaggtc accgtgaatg tgctgtcccc ccgctacgag   1440
atcgtgatca tcaccgtggt cgctgcagct gtgatcatgg gcacagccgg cctgagcaca   1500
tacctgtaca accggcagcg gaagatcaag aagtacaggc tgcagcaggc ccagaaaggc   1560 accccccatga agcccaacac ccaggccacc cctccc                           1596
```

<210> SEQ ID NO 21
<211> LENGTH: 750
<212> TYPE: DNA
<213> ORGANISM: Artificial Sequence
<220> FEATURE:
<223> OTHER INFORMATION: Optimized LFA-3 coding sequence from mBN373 and mBN420

<400> SEQUENCE: 21

```
atggtggctg gctctgatgc agggagagcc ctgggagtgc tgtctgtcgt gtgcctgctg      60
cactgcttcg gcttcatcag ctgcttcagc cagcagatct acggagtggt ctacggcaac     120
gtgaccttcc acgtgcccag caacgtgcct ctgaaagagg tgctctggaa gaaacagaag     180
gacaaggtcg cagagctgga gaacagcgag ttccgggcct cagcagcttc aagaaccgg      240 gtgtacctgg acaccgtgtc cggcagcctg accatctaca acctgaccag cagcgacgag     300
gacgagtacg agatggaaag ccctaacatc accgacacca tgaagttctt tctgtacgtg     360
ctggaaagcc tgcccagccc aacactgacc tgtgccctga ccaacggctc catcgaggtg     420
cagtgcatga ttcccgagca ctacaactcc acagaggcc  tgatcatgta ctcttgggac     480
tgccctatgg aacagtgcaa gcgcaacagc accagcatct acttcaagat ggagaacgac     540
ctccctcaga gatccagtg cacactgagc aatccactgt tcaacaccac atccagcatc      600
atcctgacaa cctgtattcc cagcagtggc cacagcagac acagatacgc cctgatccct     660
attccactgg ccgtgatcac cacatgcatc gtgctgtaca tgaacggcat cctgaagtgc     720
gaccggaagc ccgaccggac caacagcaac                                      750
```

<210> SEQ ID NO 22
<211> LENGTH: 750
<212> TYPE: DNA
<213> ORGANISM: Artificial Sequence
<220> FEATURE:
<223> OTHER INFORMATION: LFA-3 coding sequence from PANVAC

<400> SEQUENCE: 22

```
atggttgctg ggagcgacgc ggggcgggcc ctggggggtcc tcagcgtggt ctgcctgctg     60
cactgctttg gtttcatcag ctgtttttcc caacaaatat atggtgttgt gtatgggaat     120
gtaactttcc atgtaccaag caatgtgcct ttaaaagagg tcctatggaa aaaacaaaag     180
gataaagttg cagaactgga aaattctgaa ttcagagctt ctcatctttt aaaaatagg     240 gtttatttag acactgtgtc aggtagcctc actatctaca acttaacatc atcagatgaa     300
gatgagtatg aaatggaatc gccaaatatt actgatacca tgaagttctt tctttatgtg     360
cttgagtctc ttccatctcc cacactaact tgtgcattga ctaatggaag cattgaagtc     420
caatgcatga taccagagca ttacaacagc atcgaggac  ttataatgta ctcatgggat     480
tgtcctatgg agcaatgtaa acgtaactca accagtatat attttaagat ggaaaatgat     540
cttccacaaa aaatacagtg tactcttagc aatccattat taatacaac  atcatcaatc     600 attttgacaa cctgtatccc aagcagcggt cattcaagac acagatatgc acttataccc     660
ataccattag cagtaattac aacatgtatt gtgctgtata tgaatggtat tctgaaatgt     720
gacagaaaac cagacagaac caactccaat                                      750
```

<210> SEQ ID NO 23
<211> LENGTH: 750
<212> TYPE: DNA
<213> ORGANISM: Artificial Sequence
<220> FEATURE:
<223> OTHER INFORMATION: Optimized LFA-3 coding sequence from mBN336

<400> SEQUENCE: 23

```
atggtggctg gctctgatgc aggcagagcc ctgggcgtgc tgtctgtcgt gtgcctgctg      60
cactgcttcg gcttcatcag ctgcttcagc cagcagatct acggcgtggt gtacggcaac     120
gtgaccttcc acgtgcccag caacgtgcct ctgaaagagg tgctctggaa gaagcagaag     180
gacaaggtcg cagagctgga aaacagcgag ttccgggcct tcagcagctt caagaaccgg     240
gtgtacctgg acaccgtgtc cggcagcctg accatctaca acctgaccag cagcgacgag     300
gacgagtacg agatggaaag ccccaacatc accgacacca tgaagttctt tctgtacgtg     360
ctggaaagcc tgcccagccc caccctgacc tgtgccctga ccaacggctc catcgaggtg     420
cagtgcatga tcccgagca ctacaactcc caccggggcc tgatcatgta ctcttgggac     480
tgccctatgg aaacgtgcaa gcgcaacagc accagcatct acttcaagat ggaaaacgac     540
ctcccccaga aatccagtg caccctgagc aaccccctgt caacaccac ctccagcatc     600
atcctgacca cctgtatccc cagcagcggc acagcagac acagatacgc cctgatcccc     660
atcccctgg ccgtgatcac cacatgcatc gtgctgtaca tgaacggcat cctgaagtgc     720
gaccggaagc ccgaccggac caacagcaac                                       750
```

<210> SEQ ID NO 24
<211> LENGTH: 9
<212> TYPE: PRT
<213> ORGANISM: Artificial Sequence
<220> FEATURE:
<223> OTHER INFORMATION: MUC1 Agonist Epitope

<400> SEQUENCE: 24

Tyr Leu Ala Pro Pro Ala His Gly Val
1               5

<210> SEQ ID NO 25
<211> LENGTH: 9
<212> TYPE: PRT
<213> ORGANISM: Artificial Sequence
<220> FEATURE:
<223> OTHER INFORMATION: MUC1 agonist epitope

<400> SEQUENCE: 25

Tyr Leu Asp Thr Arg Pro Ala Pro Val
1               5

<210> SEQ ID NO 26
<211> LENGTH: 10
<212> TYPE: PRT
<213> ORGANISM: Artificial Sequence
<220> FEATURE:
<223> OTHER INFORMATION: MUC1 agonist epitope

<400> SEQUENCE: 26

Tyr Leu Ala Ile Val Tyr Leu Ile Ala Leu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: MUC1 agonist epitope

<400> SEQUENCE: 27

Tyr Leu Ile Ala Leu Ala Val Cys Gln Val

<210> SEQ ID NO 28
<211> LENGTH: 9
<212> TYPE: PRT
<213> ORGANISM: Artificial Sequence
<220> FEATURE:
<223> OTHER INFORMATION: MUC1 agonist epitope

<400> SEQUENCE: 28

```
Tyr Leu Ser Tyr Thr Asn Pro Ala Val
1               5
```

<210> SEQ ID NO 29
<211> LENGTH: 9
<212> TYPE: PRT
<213> ORGANISM: Artificial Sequence
<220> FEATURE:
<223> OTHER INFORMATION: MUC1 agonist epitope

<400> SEQUENCE: 29

```
Ser Leu Phe Arg Ser Pro Tyr Glu Lys
1               5
```

<210> SEQ ID NO 30
<211> LENGTH: 455
<212> TYPE: PRT
<213> ORGANISM: Artificial Sequence
<220> FEATURE:
<223> OTHER INFORMATION: MUC1 amino acid sequence as found in mBN336, mBN373, and mBN420

<400> SEQUENCE: 30

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
                35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95

Asp Val Thr Ser Val Pro Val Thr Arg Pro Ala Leu Gly Tyr Leu Ala
                100                 105                 110

Pro Pro Ala His Gly Val Thr Ser Tyr Leu Asp Thr Arg Pro Ala Pro
                115                 120                 125

Val Ser Thr Ala Pro Pro Ala His Gly Val Thr Ser Ala Pro Asp Thr
    130                 135                 140

Arg Pro Ala Pro Gly Ser Thr Ala Pro Ala His Gly Val Thr Ser
145                 150                 155                 160

Ala Pro Asp Thr Arg Pro Ala Pro Ala Ser Thr Leu Val His Asn Gly
                165                 170                 175

Thr Ser Ala Arg Ala Thr Thr Thr Pro Ala Ser Lys Ser Thr Pro Phe
                180                 185                 190

Ser Ile Pro Ser His His Ser Asp Thr Pro Thr Thr Leu Ala Ser His
                195                 200                 205

Ser Thr Lys Thr Asp Ala Ser Ser Thr His His Ser Thr Val Pro Pro
```

```
Leu Thr Ser Ser Asn His Ser Thr Ser Pro Gln Leu Ser Thr Gly Val
225                 230                 235                 240

Ser Phe Phe Phe Leu Ser Phe His Ile Ser Asn Leu Gln Phe Asn Ser
            245                 250                 255

Ser Leu Glu Asp Pro Ser Thr Asp Tyr Tyr Gln Glu Leu Gln Arg Asp
            260                 265                 270

Ile Ser Glu Met Phe Leu Gln Ile Tyr Lys Gln Gly Gly Phe Leu Gly
            275                 280                 285

Leu Ser Asn Ile Lys Phe Arg Pro Gly Ser Val Val Val Gln Leu Thr
    290                 295                 300

Leu Ala Phe Arg Glu Gly Thr Ile Asn Val His Asp Val Glu Thr Gln
305                 310                 315                 320

Phe Asn Gln Tyr Lys Thr Glu Ala Ala Ser Arg Tyr Asn Leu Thr Ile
                325                 330                 335

Ser Asp Val Ser Val Ser Asp Val Pro Phe Pro Phe Ser Ala Gln Ser
            340                 345                 350

Gly Ala Gly Val Pro Gly Trp Gly Ile Ala Leu Leu Val Leu Val Cys
            355                 360                 365

Val Leu Val Tyr Leu Ala Ile Val Tyr Leu Ile Ala Leu Ala Val Cys
    370                 375                 380

Gln Val Arg Arg Lys Asn Tyr Gly Gln Leu Asp Ile Phe Pro Ala Arg
385                 390                 395                 400

Asp Thr Tyr His Pro Met Ser Glu Tyr Pro Thr Tyr His Thr His Gly
                405                 410                 415

Arg Tyr Val Pro Pro Ser Ser Leu Phe Arg Ser Pro Tyr Glu Lys Val
            420                 425                 430

Ser Ala Gly Asn Gly Gly Ser Tyr Leu Ser Tyr Thr Asn Pro Ala Val
            435                 440                 445

Ala Ala Thr Ser Ala Asn Leu
    450                 455

<210> SEQ ID NO 31
<211> LENGTH: 1365
<212> TYPE: DNA
<213> ORGANISM: Artificial Sequence
<220> FEATURE:
<223> OTHER INFORMATION: MUC1 coding sequence for mBN336 w/o agonist
      epitopes from WO 2013/103658

<400> SEQUENCE: 31
atgacaccgg gcacccagtc tcctttcttc ctgctgctgc tcctcacagt gcttacagtt      60
gttacgggtt ctggtcatgc aagctctacc ccaggtggag aaaaggagac ttcggctacc     120
cagagaagtt cagtgcccag ctctactgag aagaatgctg tgagtatgac aagtccgta      180 ctctccagcc acagcccagg ttcaggctcc tccaccactc agggacagga tgtcactctg     240
gcaccggcca cggaaccagc ttcaggttca gctgccttgt ggggacagga tgtcacctcg     300
gtaccagtta ctagaccagc tttaggcagc acagcgccac cggctcatgg cgttacatcg     360
gctcctgaca ctcgaccggc accaggcagc acagcacctc ccgcacacgg tgtaactagc     420
gcgcctgata cacgtcccgc tcccggatct accgctccgc cagcgcacgg agtgacgtca     480
gcaccagata cgaggccagc gcctgctagc actctggtgc acaacggcac ctctgccagg     540
gctaccacaa ccccagccag caagagcact ccattctcaa ttcccagcca ccactctgat     600
actcctacca cccttgccag ccatagcacc aagactgatg ccagtagcac tcaccatagc     660
```

```
acggtacctc ctctcacctc ctccaatcac agcacttctc cccagttgtc tactggggtc    720
tctttctttt tcctgtcttt tcacatttca aacctccagt ttaattcctc tctggaagat    780
cccagcaccg actactacca agagctgcag agagacattt ctgaaatgtt tttgcagatt    840
tataaacaag ggggttttct gggcctctcc aatattaagt tcaggccagg atctgtggtg    900
gtacagttga ctctggcctt ccgagaaggt accatcaatg tccacgacgt ggagacacag    960
ttcaatcagt ataaaacgga agcagcctct cgatataacc tgacgatctc agacgtcagc   1020
gtgagtgatg tgccatttcc tttctctgcc cagtctgggg ctggggtgcc aggctggggc   1080
atcgcgctgc tggtgctggt ctgtgttctg gttgcactgg ccattgtcta tctcattgcc   1140
ttggctgtct gtcagtgccg ccgaaagaac tacgggcagc tggacatctt ccagcccgg   1200 gatacctacc atcctatgag cgagtacccc acctaccaca cccatgggcg ctatgtgccc   1260
cctagcagta ccgatcgtag cccctatgag aaggtttctg caggtaatgg tggcagcagt   1320
ctctcttaca caaacccagc agtggcagcc acttctgcca acttg                   1365
```

<210> SEQ ID NO 32
<211> LENGTH: 1365
<212> TYPE: DNA
<213> ORGANISM: Artificial Sequence
<220> FEATURE:
<223> OTHER INFORMATION: MUC1 coding sequence for mBN373 w/o agonist epitopes from WO 2013/103658

<400> SEQUENCE: 32

```
atgacaccgg gcacccagtc tcctttcttc ctgctgctgc tcctcacagt gcttacagtt     60
gttacgggtt ctggtcatgc aagctctacc ccaggtggag aaaaggagac ttcggctacc    120
cagagaagtt cagtgcccag ctctactgag aagaatgctg tgagtatgac aagctccgta    180
ctctccagcc acagcccagg ttcaggctcc tccaccactc agggacagga tgtcactctg    240
gcaccggcca cggaaccagc ttcaggttca gctgccttgt ggggacagga tgtcacctcg    300
gtaccagtta ctagaccagc tttaggcagc acagcgccac cggctcatgg cgttacatcg    360
gctcctgaca ctcgaccggc accaggcagc acagcacctc ccgcacacgg tgtaactagc    420
gcgcctgata cacgtcccgc tcccggatct accgctccgc cagcgcacgg agtgacgtca    480
gcaccagata cgaggccagc gcctgctagc actctggtgc acaacggcac ctctgccagg    540
gctaccacaa ccccagccag caagagcact ccattctcaa ttcccagcca ccactctgat    600
actcctacca cccttgccag ccatagcacc aagactgatg ccagtagcac tcaccatagc    660
acggtacctc ctctcacctc ctccaatcac agcacttctc cccagttgtc tactggggtc    720
tctttctttt tcctgtcttt tcacatttca aacctccagt ttaattcctc tctggaagat    780
cccagcaccg actactacca agagctgcag agagacattt ctgaaatgtt tttgcagatt    840
tataaacaag ggggttttct gggcctctcc aatattaagt tcaggccagg atctgtggtg    900
gtacagttga ctctggcctt ccgagaaggt accatcaatg tccacgacgt ggagacacag    960
ttcaatcagt ataaaacgga agcagcctct cgatataacc tgacgatctc agacgtcagc   1020
gtgagtgatg tgccatttcc tttctctgcc cagtctgggg ctggggtgcc aggctggggc   1080
atcgcgctgc tggtgctggt ctgtgttctg gttgcactgg ccattgtcta tctcattgcc   1140
ttggctgtct gtcagtgccg ccgaaagaac tacgggcagc tggacatctt ccagcccgg   1200 gatacctacc atcctatgag cgagtacccc acctaccaca cccatgggcg ctatgtgccc   1260
cctagcagta ccgatcgtag cccctatgag aaggtttctg caggtaatgg tggcagcagt   1320
```

```
ctctcttaca caaacccagc agtggcagcc acttctgcca acttg            1365
```

<210> SEQ ID NO 33
<211> LENGTH: 1365
<212> TYPE: DNA
<213> ORGANISM: Artificial Sequence
<220> FEATURE:
<223> OTHER INFORMATION: MUC1 coding sequence for mBN420 w/o agonist
      epitopes from WO 2013/103658

<400> SEQUENCE: 33

```
atgacacctg gcactcagtc accattcttc ctgctgttac tcttgacagt gcttacagtt    60
gttacaggtt ctggtcatgc aagctctacc ccaggtggag aaaaggagac ttcggctacc   120
cagcggagtt cagtgcctag ctctactgag aagaatgctg tgagtatgac aagctccgta   180
ctctccagcc acagcccagg ttcaggctcc agcaccactc aaggacagga tgtcactctg   240
gcaccggcca cggaaccagc ttcaggttca gctgccttgt ggggacagga tgtcacatcg   300
gtaccagtta ctagaccagc tttaggcagc acagcgccac cggctcatgg cgttacatcg   360
gctcctgaca ctcgaccggc accaggcagc acagcacctc cgcacacgg tgtaactagc   420
gcgcctgata cacgtcccgc tcccggatct accgctccgc cagcgcacgg agtgacgtca   480
gcaccagata cgaggccagc gcctgctagc actctggtgc acaatggcac atctgccagg   540
gctaccacaa ctccagccag caagagcact ccattctcaa ttccaagcca tcactctgat   600
actcctacca cacttgccag ccatagcacc aagactgatg ccagtagcac tcaccatagc   660
acggtacctc cactcaccctc atccaatcac agcacttctc ctcagttgtc tactggagtc   720
tccttcttt tcctgtccctt tcacatttca aacttgcagt tcaattcttc cctggaagat   780
cccagcaccg actactacca agagctgcag agagacattt ctgagatgtt cttgcagatt   840
tataaacaag gtggattcct tggcctctct aatattaagt tcaggccagg atctgtggtc   900
gtacagttga ctctggcctt cagagaaggt accatcaatg tccacgacgt ggagacacag   960
ttcaatcagt ataagacgga agcagcctca cgatataacc tgacgatctc agacgtcagc  1020
gttagtgatg tgccatttcc tttctctgcc cagtctggag ctggtgtgcc aggctggggc  1080
atcgcgctgc tcgtgttggt ctgtgttctg gttgcactgg ccattgtcta tctcattgcc  1140
ttggctgtttt gtcagtgcag acgcaagaac tacggacagc tggacatctt ccagctcgg  1200
gataccta atccatatgag cgagtaccct acctaccaca cacatggtcg ctatgtgcca  1260
cctagcagta ccgatcgtag tccctatgag aaagtttctg caggtaatgg tggcagcagt  1320
ctctcttaca caaacccagc agtggcagcc acttctgcca acttg            1365
```

<210> SEQ ID NO 34
<211> LENGTH: 1365
<212> TYPE: DNA
<213> ORGANISM: Artificial Sequence
<220> FEATURE:
<223> OTHER INFORMATION: MUC1 coding sequence for mBN optimized w/o
      agonist epitopes from WO 2013/103658

<400> SEQUENCE: 34

```
atgacacctg gcactcagtc accattcttc ctgctgttac tcttgacagt gcttacagtt    60
gttacaggtt ctggtcatgc aagctctacc ccaggtggag aaaaggagac ttcggctacc   120
cagcggagtt cagtgcctag ctctactgag aagaatgctg tgagtatgac aagctccgta   180
ctctccagcc acagcccagg ttcaggctcc agcaccactc aaggacagga cgtcactctg   240
```

-continued

```
gcaccggcca cggaaccagc ttcaggttca gctgccttgt ggggacagga tgtgacatcg    300
gtaccagtta ctagaccagc tttaggcagc acagcgccac cggctcatgg cgttacatcg    360
gctcctgaca ctcgaccggc accaggcagc acagcacctc ccgcacacgg tgtaactagc    420
gcgcctgata cacgtcccgc tcccggatct accgctccgc cagcgcacgg agtgacgtca    480
gcaccagata cgaggccagc gcctgctagc actctggtgc acaatggcac atctgccagg    540
gctaccacaa ctccagccag caagagcact ccattctcaa ttccaagcca tcactctgat    600
actcctacca cacttgccag ccatagcacc aagactgatg ccagtagcac tcaccatagc    660
acggtacctc cactcacctc atccaatcac agcacttctc ctcagttgtc tactggagtc    720
tccttctttt tcctgtcctt tcacatttca aacttgcagt tcaattcttc cctggaagat    780
cccagcaccg actactacca agagctgcag agagacattt ctgagatgtt cttgcagatt    840
tataaacaag gtggattcct tggcctctct aatattaagt tcaggccagg atctgtggtc    900
gtacagttga ctctggcctt cagagaaggt accatcaatg tccacgacgt ggagacacag    960
ttcaatcagt ataagacgga agcagcctca cgatataacc tgacgatctc agacgtcagc   1020
gttagtgatg tgccatttcc tttctctgcc cagtctggag ctggtgtgcc aggctggggc   1080
atcgcgctgc tcgtgttggt ctgtgttctg gttgcactgg ccattgtcta tctcattgcc   1140
ttggctgttt gtcagtgcag acgcaagaac tacggacagc tggacatctt ccagctcgg    1200
gataccta cc atcctatgag cgagtaccct acctaccaca catggtcg ctatgtgcca    1260
cctagcagta ccgatcgtag tccctatgag aaagtttctg caggtaatgg tggcagcagt   1320
ctctcttaca caaacccagc agtggcagcc acttctgcca acttg                  1365
```

<210> SEQ ID NO 35
<211> LENGTH: 455
<212> TYPE: PRT
<213> ORGANISM: Artificial Sequence
<220> FEATURE:
<223> OTHER INFORMATION: MUC1 amino acid from mBN336/mBN373/mBN420 w/o agonist epitopes from WO 2013/103658

<400> SEQUENCE: 35

```
Met Thr Pro Gly Thr Gln Ser Pro Phe Phe Leu Leu Leu Leu Thr
 1               5                  10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95

Asp Val Thr Ser Val Pro Val Thr Arg Pro Ala Leu Gly Ser Thr Ala
            100                 105                 110

Pro Pro Ala His Gly Val Thr Ser Ala Pro Asp Thr Arg Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160
```

```
Ala Pro Asp Thr Arg Pro Ala Pro Ala Ser Thr Leu Val His Asn Gly
            165                 170                 175
Thr Ser Ala Arg Ala Thr Thr Thr Pro Ala Ser Lys Ser Thr Pro Phe
            180                 185                 190
Ser Ile Pro Ser His His Ser Asp Thr Pro Thr Thr Leu Ala Ser His
            195                 200                 205
Ser Thr Lys Thr Asp Ala Ser Ser Thr His His Ser Thr Val Pro Pro
            210                 215                 220
Leu Thr Ser Ser Asn His Ser Thr Ser Pro Gln Leu Ser Thr Gly Val
225                 230                 235                 240
Ser Phe Phe Phe Leu Ser Phe His Ile Ser Asn Leu Gln Phe Asn Ser
            245                 250                 255
Ser Leu Glu Asp Pro Ser Thr Asp Tyr Tyr Gln Glu Leu Gln Arg Asp
            260                 265                 270
Ile Ser Glu Met Phe Leu Gln Ile Tyr Lys Gln Gly Gly Phe Leu Gly
            275                 280                 285
Leu Ser Asn Ile Lys Phe Arg Pro Gly Ser Val Val Val Gln Leu Thr
    290                 295                 300
Leu Ala Phe Arg Glu Gly Thr Ile Asn Val His Asp Val Glu Thr Gln
305                 310                 315                 320
Phe Asn Gln Tyr Lys Thr Glu Ala Ala Ser Arg Tyr Asn Leu Thr Ile
                325                 330                 335
Ser Asp Val Ser Val Ser Asp Val Pro Phe Pro Phe Ser Ala Gln Ser
            340                 345                 350
Gly Ala Gly Val Pro Gly Trp Gly Ile Ala Leu Leu Val Leu Val Cys
            355                 360                 365
Val Leu Val Ala Leu Ala Ile Val Tyr Leu Ile Ala Leu Ala Val Cys
    370                 375                 380
Gln Cys Arg Arg Lys Asn Tyr Gly Gln Leu Asp Ile Phe Pro Ala Arg
385                 390                 395                 400
Asp Thr Tyr His Pro Met Ser Glu Tyr Pro Thr Tyr His Thr His Gly
                405                 410                 415
Arg Tyr Val Pro Pro Ser Ser Thr Asp Arg Ser Pro Tyr Glu Lys Val
            420                 425                 430
Ser Ala Gly Asn Gly Gly Ser Ser Leu Ser Tyr Thr Asn Pro Ala Val
            435                 440                 445
Ala Ala Thr Ser Ala Asn Leu
    450                 455
```